(12) United States Patent
Ghosh

(10) Patent No.: US 8,501,961 B2
(45) Date of Patent: Aug. 6, 2013

(54) HIV PROTEASE INHIBITORS AND METHODS FOR USING

(75) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/002,916

(22) PCT Filed: Jul. 8, 2009

(86) PCT No.: PCT/US2009/049937
§ 371 (c)(1),
(2), (4) Date: Jan. 6, 2011

(87) PCT Pub. No.: WO2010/006050
PCT Pub. Date: Jan. 14, 2010

(65) Prior Publication Data
US 2011/0118330 A1    May 19, 2011

Related U.S. Application Data

(60) Provisional application No. 61/079,237, filed on Jul. 9, 2008.

(51) Int. Cl.
| | | |
|---|---|---|
| *C07D 487/02* | (2006.01) |
| *C07D 495/02* | (2006.01) |
| *C07D 311/94* | (2006.01) |
| *A61K 31/407* | (2006.01) |
| *A61K 31/4015* | (2006.01) |
| *A61K 31/38* | (2006.01) |
| *A61K 31/35* | (2006.01) |

(52) U.S. Cl.
USPC ............. 548/453; 549/50; 549/396; 514/412; 514/421; 514/443; 514/456

(58) Field of Classification Search
None
See application file for complete search history.

(56) References Cited

U.S. PATENT DOCUMENTS

| | | | |
|---|---|---|---|
| 5,723,490 A | 3/1998 | Tung et al. |
| 5,728,718 A | 3/1998 | Randad et al. |
| 6,313,345 B1 | 11/2001 | Vazquez et al. |
| 6,649,651 B1 | 11/2003 | Wigerinck et al. |
| 2004/0122000 A1 | 6/2004 | Hale et al. |
| 2005/0159469 A1 | 7/2005 | Randolph et al. |
| 2005/0214890 A1 | 9/2005 | Tan et al. |
| 2006/0293286 A1 | 12/2006 | Erickson et al. |
| 2007/0082883 A1 | 4/2007 | Ghosh et al. |
| 2007/0117793 A1 | 5/2007 | Ghosh et al. |
| 2008/0096942 A1 | 4/2008 | Tenbrink et al. |
| 2010/0113582 A1 | 5/2010 | Ghosh |

FOREIGN PATENT DOCUMENTS

| | | |
|---|---|---|
| WO | WO 96/22087 | 7/1996 |
| WO | WO 96/33187 | 10/1996 |
| WO | WO 99/67254 | 12/1999 |
| WO | WO 01/25240 | 4/2001 |
| WO | WO 2008/133734 | 11/2008 |
| WO | WO 2010/002994 | 1/2010 |
| WO | WO 2010/006050 | 1/2010 |

OTHER PUBLICATIONS

International Search Report for PCT/US2009/049937 completed Aug. 26, 2009.
Ghosh, Arun K., et al., "Nonpeptidal P2 Ligands for HIV Protease Inhibitors: Structure-Based Design, Synthesis, and Biological Evaluation", 1996, Journal Med. Chem., No. 39, pp. 3278-3290.
Ghosh, Arun K., et al., "Novel Cyclourethane-Derived HIV Protease Inhibitors: A Ring-Closing Olefin Metathesis Based Strategy", 2002, Bioorganic & Medicinal Chemistry Letters, No. 12, pp. 1993-1996.
Ghosh, Arun K., et al., "Structure-Based Design: Synthesis and Biological Evaluation of a Series of Novel Cycloamide-Derived HIV-1 Protease Inhibitors", 2005, Journal Med. Chem., No. 48, pp. 3576-3585.
Ghosh, Arun K., et al., "Design and Synthesis of Novel HIV-1 Protease Inhibitors Incorporating Oxyindoles as the P2-Ligands", 2006, Bioorganic & Medicinal Chemistry Letters, No. 16, pp. 1869-1873.
Nakamura Mariko, et al., "Inhibitory Effects of Polyethers on Human Immunodeficiency Virus Replication", Feb. 1992, Antimicrobial Agents and Chemotherapy, vol. 36, No. 2, pp. 492-494.
Ami et al., "Synthesis of Novel Amino Acids, L-Bis-Tetrahydrofuranylglycines," Tetrahedron Letters, vol. 43, 2931-2934 (2002).
Babe et al., "Synthetic "interface" Peptides Alter Dimeric Assembly of the HIV 1 and 2 Proteases," Protein Science, vol. 1, No. 10, 1244-1253 (1992).
Bannwarth et al., "Molecular Tongs Containing Amino Acid Mimetic Fragments: New Inhibitors of Wild-Type and Mutated HIV-1 Protease Dimerization," J. Med. Chem., vol. 49, No. 15, 4657-4664 (2006).
Bastiaens et al., "Imaging the Intracellular Trafficking and State of the $AB_5$ Quaternary Structure of Cholera Toxin," EMBO Journal, vol. 15, No. 16, 4246-4253 (1996).
Bowman et al., "Switching between Allosteric and Dimerization Inhibition of HIV-1 Protease," Chemistry & Biology, vol. 12, No. 4, 439-444 (2005).
Carr, "Toxicity of antiretroviral therapy and implications for drug development," Nature Reviews Drug Disc, vol. 2, 624-634 (2003).
Chen et al., "Syntheses of a New Cerebroside Isolated from Typhonium Giganteum Engl," Chinese Journal of Chemistry, vol. 21, 937-943 (2003).
Davis et al., "Inhibition of HIV-1 Replication by a Peptide Dimerization Inhibitor of HIV-1 Protease", Antiviral Research, vol. 72, No. 2, 89-99 (2006).
De Clercq, "Strategies in the design of antiviral drugs," Nature Reviews Drug Disc, vol. 1, 13-25 (2002).

(Continued)

*Primary Examiner* — Nyeemah A Grazier
(74) *Attorney, Agent, or Firm* — Barnes & Thornburg LLP

(57) ABSTRACT

Compounds that inhibit proteolytic enzymes of Human Immunodeficiency Virus (HIV) are described. Preparation of the inhibitors, pharmaceutical compositions containing them, and uses of the compounds or compositions for the treatment of HIV infections are also described.

12 Claims, No Drawings

OTHER PUBLICATIONS

De Meyer et al., "TMC114, a Novel Human Immunodeficiency Virus Type 1 Protease Inhibitor Active against Protease Inhibitor-Resistant Viruses, Including a Broad Range of Clinical Isolates," Antimicrobial Agents and Chemotherapy, vol. 49, No. 6, 2314-2321 (2005).

Fang et al., "PCR-Mediated Recombination: A General Method Applied to Construct Chimeric Infectious Molecular Clones of Plasma-Derived HIV-1 RNA," Nature Medicine, vol. 5, No. 2, 239-242 (1999).

Firulli et al., "Altered Twist1 and Hand2 Dimerization is Associated with Saethre-Chotzen Syndrome and Limb Abnormalities," Nature genetics, vol. 37, No. 4, 373-381 (2005).

Friesner et al., "Glide: a new approach for rapid, accurate docking and scoring. 1. Method and assessment of docking accuracy," J. Med. Chem., vol. 47, 1739-1749 (2004).

Frutos et al., "Disruption of the HIV-1 Protease Dimer with Interface Peptides: Structural Studies Using NMR Spectroscopy Combined with [2-$^{13}$C]-Trp Selective Labeling," Peptide Science, vol. 88, 164-173 (2007).

Fumero et al., "New patterns of HIV-1 resistance during HAART," European Society of Clinical Microbiology and Infectious Diseases, vol. 9, 1077-1084 (2003).

Gatanaga et al., "Amino Acid Substitutions in Gag Protein at Non-Cleavage Sites are Indispensable for the Development of a High Multitude of HIV-1 Resistance Against Protease Inhibitors," Journal of Biological Chemistry, vol. 277, No. 8, 5952-5961 (2002).

Ghosh et al., "Potent HIV protease inhibitors incorporating high-affinity P2-ligands and (R)-(hydroxyethylamino)sulfonamide isostere," Bioorganic & Medicinal Chemistry Letters, vol. 8, 687-690 (1998).

Ghosh et al., "Structure based design: novel spirocyclic ethers as nonpeptidal P2-ligands for HIV protease inhibitors," Bioorganic & Medicinal Chemistry Letters, vol. 8, 979-982 (1998).

Ghosh et al., "Structure-Based Design of Novel HIV-1 Protease Inhibitors to Combat Drug Resistance," J. Med. Chem., vol. 49, 5252-5261 (2006).

Grabar et al., "HIV infection in older patients in the HAART era," Journal of Antimicrobial Chemotherapy, vol. 57, 4-7 (2005).

Hirsch et al., "Immune reconstitution in HIV-infected patients," Clinical Infectious Diseases, 2004, 38:1159-66.

Hong et al., "Crystal structure of an in vivo HIV-1 protease mutant in complex with saquinavir: insights into the mechanisms of drug resistance," Protein Science, vol. 9, 1898-1904 (2000).

Ishima et al., "Solution Structure of the Mature HIV-1 Protease Monomer," J. Biol. Chem., vol. 278, No. 44, 43311-43319 (2003).

Ishima et al., "Folded Monomer of HIV-1 Protease," J. Biol. Chem., vol. 276, No. 52, 49110-49116 (2001).

Kaplan et al., "Selection of multiple human immunodeficiency virus type 1 variants that encode viral proteases with decreased sensitivity to an inhibitor of the viral protease," PNAS USA, vol. 91, 5597-5601 (1994).

Koh et al., "Novel bis tetrahydrofuranylurethane-containing nonpeptidic protease inhibitor (PI) UIC-94017 (TMC114) with potent activity against multi-PI-resistant human immunodeficiency virus in vitro," Antimicrobial Agents and Chemotherapy, vol. 47, No. 10, 3123-3129 (2003).

Konvalinka et al., "An Active-Site Mutation in the Human Immunodeficiency Virus Type 1 Proteinase (PR) Causes Reduced PR Activity and Loss of PR-Mediated Cytotoxicity without Apparent Effect on Virus Maturation and Infectivity," Journal of Virology, vol. 69, No. 11, 7180-7186 (1995).

Kovalevsky et al., "Effectiveness of nonpeptide clinical inhibitor TMC-114 on HIV-1 protease with highly drug resistant mutations D30N, I50V, and L90M," J. Med. Chem., vol. 49, 1379-1387 (2006).

Kovalevsky et al., "Ultra-High Resolution Crystal Structure of HIV-1 Protease Mutant Reveals Two Binding Sites for Clinical Inhibitor TMC114," J. Mol. Biol., vol. 363, No. 1, 161-173 (2006).

Lapatto et al., "X-Ray Analysis of HIV-1 Proteinase and 2.7 Å Resolution Confirms Structural Homology Among Retroviral Enzymes," Nature, vol. 342, 299-302 (1989).

Levy et al., "The Folding and Dimerization of HIV-1 Protease: Evidence for a Stable Monomer from Simulations," J. Mol. Biol., vol. 340, No. 1, 67-79 (2004).

Little et al., "Antiretroviral-drug resistance among patients recently infected with HIV," New England Journal of Medicine, vol. 347, No. 6, 385-394 (2002).

Louis et al., "Revisiting Monomeric HIV-1 Protease," J. Biol. Chem., vol. 278, No. 8, 6085-6092 (2003).

Maibaum et al., "Inhibition of Porcine Pepsin by Two Substrate Analogues Containing Statine. The Effect of Histidine at the P2 Subsite on the Inhibition of Aspartic Proteinases," J. Med. Chem., vol. 31, 625-629 (1988).

Miller et al., "Ultra-potent P1 modified arylsulfonamide HIV protease inhibitors: the discovery of GW0385," Bioorganic & Medicinal Chemistry Letters, vol. 16, 1788-1794 (2006).

Miyawaki et al., "Fluorescent Indicators for $Ca^{2+}$ Based on Green Fluorescent Proteins and Calmodulin," Nature, vol. 388, No. 6645, 882-887 (1997).

Patick et al., "Antiviral and Resistance Studies of AG1343, an Orally Bioavailable Inhibitor of Human Immunodeficiency Virus Protease," Antimicrobial Agents and Chemotherapy, vol. 40, No. 2, 292-297 (1996).

Poveda et al., "Successful rescue therapy with darunabir (TMC114) in HIV-infected patients who have failed several ritonavir-boosted protease inhibitors," AIDS, vol. 20, No. 11, 1558-1560 (2006).

Prabu-Jeyabalan et al., "Mechanism of Substrate Recognition by Drug-Resistant Human Immunodeficiency Virus Type 1 Protease Variants Revealed by a Novel Structural Intermediate," Journal of Virology. vol. 80, No. 7, 3607-3616 (2006).

Sekar et al., "Fluorescence Resonance Energy Transfer (FRET) Microscopy Imaging of Live Cell Protein Localizations," J. Cell Biology, vol. 160, No. 5, 629-633 (2003).

Sepkowitz, "AIDS—the first 20 years," New England Journal of Medicine, vol. 344, No. 23, 1764-1772 (2001).

Siegel et al., "Fas Preassociation Required for Apoptosis Signaling and Dominant Inhibition by Pathogenic Mutations", Science, 2354 (2000).

Siliciano et al., "A long-term latent reservoir for HIV-1: discovery and clinical implications," Journal of Antimicrobial Chemotherapy, vol. 54, 6-9 (2004).

Simon, et al., "HIV-1 dynamics in vivo: implications for therapy," Nature Reviews Microbiology, vol. 1, 181-190 (2003).

Staszewski et al., "Efavirenz plus zidovudine and lamivudine, efavirenz plus indinavir, and indinavir plus zidovudine and lamivudine in the treatment of HIV-1 infection in adults," New England Journal of Medicine, 1999, 341:1865-73.

Szczesna-Skorupa et al., "Fluorescence Resonance Energy Transfer Analysis of Cytochromes P450 2C2 and 2E1 Molecular Interactions in Living Cells," Journal of Biological Chemistry, vol. 278, 31269-31276 (2003).

Thaisrivongs et al., "Structure-Based Design of HIV Protease Inhibitors: Sulfonamide-Containing 5,6 Dihydro-4-hydroxy-2-pyrones as Non-Peptidic Inhibitors," J. Med. Chem., vol. 39, No. 22, 4349-4353 (1996).

Tie et al., "High resolution crystal structures of HIV-1 protease with a potent non-peptide inhibitor (UIC-94017) active against multi-drug-resistant clinical strains," J. Mol. Biol., vol. 338, 341-352 (2004).

Wainberg et al., "Public health implications of antiretroviral therapy and HIV drug resistance," J. Am. Med. Assoc., vol. 279, 1977-1983 (1998).

Wlodawer et al., "Conserved Folding in Retroviral Proteases: Crystal Structure of a Synthetic HIV-1 Protease," Science, vol. 245, 616-621 (1989).

Yoshimura et al., "JE-2147: a dipeptide protease inhibitor (PI) that potently inhibits multi-PI-resistant HIV-1," Proc. Natl. Acad. Sci. USA, vol. 96, 8675-8680 (1999).

Yoshimura et al., "A Potent Human Immunodeficiency Virus Type 1 Protease Inhibitor, UIC-94003 (TMC-126), and Selection of a Novel (A28S) Mutation in the Protease Active Site," Journal of Virology, vol. 76, No. 3, 1349-1358 (2002).

Youle et al., "Concomitant Use of an Active Boosted Protease Inhibitor with Enfuvirtide in Treatment-Experienced, HIV-Infected Individuals: Recent Data Consensus Recommendations," HIV Clin. Trials, vol. 7, No. 2, 86-96 (2006).

Ghosh et al., "Stereocontrolled Synthesis of HIV-1 Protease Inhibitors with C2-Axis of Symmetry," Tetrahedron Letters 1991, 32, 5729-33.

Ghosh et al., "An Efficient Synthesis of Hydroxyethylene Dipeptide Isosteres: The Core Unit of Potent HIV-1 Protease Inhibitors," J. Org. Chem. 1991, 56, 6500-03.

Ghosh et al., "HIV-1 Protease Inhibitors: Synthesis and biological Evalution of Glycopeptides," Drug Design and Discovery 1993, 10, 77-86.

Ghosh et al., "Potent HIV-1 Protease Inhibitors : Stereoselective Synthesis of a New Dipeptide Mimic," J. Org. Chem. 1993, 58, 1025-32.

W. J. Thompson et al., "3'-Tetrahydrofuranglycine as a Novel, Unnatural Amino Acid Surrogate for Asparagine in the Design of Inhibitors of the HIV Protease," J. Am. Chem. Soc. 1993, 115, 801-03.

Ghosh et al., "3-Tetrahydrofuran and pyranyl Urethanes as High Affinity P2-Ligands for HIV-1 Protease Inhibitors," J. Med. Chem. 1993, 36, 292-94.

Ghosh et al., "Cyclic sulfones as novel and High Affinity P2-Ligands for HIV Protease Inhibitors," J. Med. Chem. 1993, 36, 924-27.

Ghosh et al., "Potent HIV Protease Inhibitors: The Development of 3'-tetrahydrofuranglycine as P2-Ligands and substituted Pyrazine Derivatives as P3-Ligands," J. Med. Chem., 1993, 36, 2300-10.

Ghosh et al., "Structure Based Design of HIV-1 Protease Inhibitors: Replacements of Two Amides and a 10π Electron Aromatic System by a Fused Bis-tetrahydrofuran" J. Med. Chem. 1994, 37, 2506-08.

Ghosh et al., "The Development of Cyclic Sulfolanes as Novel and High Affinity P2-Ligands for HIV-1 Protease Inhibitors," J. Med. Chem. 1994, 37, 1177-88.

M. K. Holloway et al., "A Priori Prediction of Activity for HIV-1 Protease Inhibitors Employing Energy Minimization in the Active Site" J. Med. Chem., 1995, 38, 305-17.

Ghosh et al., "Synthesis and Optical Resolution of High Affinity P2-Ligands for HIV-1 Protease Inhibitors," Tetrahedron Letters, 1995, 36, 505-08.

Ghosh et al., "Cyclic Sulfone-3-Carboxamide as Novel P2-ligands for HIV-1 Protease Inhibitors," Bioorganic and Med. Chem. Letters, 1995, 5, 83-88.

Ghosh et al., "Chiral Auxiliary Mediated Conjugate reduction and Asymmetric Protonation: Synthesis of High Affinity Ligands for HIV Protease Inhibitors," J. Org. Chem. 1995, 60, 6198-6201.

Ghosh et al., "A Convenient Enzymatic Route to Optically Active 1-Aminoindan-2-ol: Versatile Ligands for HIV-1 Protease Inhibitors and Asymmetric Syntheses," Synthesis 1997, 541-44.

Ghosh et al., "Asymmetric Aldol Route to Hydroxyethylamine Isostere: Stereoselective Synthesis of the Core Unit of Saquinavir," J. Org. Chem. 1997, 62, 6080-82.

Ghosh et al., "Ring-Closing Metathesis Strategy to α,β-unsaturated γ- and δ-Lactones: Synthesis of Hydroxyethylamine Isosteres for HIV Protease Inhibitors," Tetrahedron Letters, 1998, 8, 4651-54.

Ghosh et al., "Transition-State Mimetics for HIV Protease Inhibitors: Stereocontrolled Synthesis of Hydroxyethylene and Hydroxyethylamine Isosteres by Ester Derived Titanium Enolate Syn- and Anti-aldol Reactions," J. Org. Chem. 1998, 63, 6146-52.

Ghosh et al., "Asymmetric dihydroxylation route to a dipeptide isostere of a protease inhibitor: enantioselective synthesis of the core unit of ritonavir," Chem. Commun. 1999, 1025-26.

Ghosh et al., "2,5-Anhydro Sugar Diacid and 2,5-Anhydro Sugar Diamine Based $C_2$-Symmetric Peptidomimetics as Potential HIV-1 Protease Inhibitors," Tetrahedron Letters 2001, 42, 10121-24.

Ghosh et al., "Structure-based Design of Nonpeptide HIV Protease Inhibitors," Farmaco 2001, 56, 29-32.

Ghosh et al., "Syntheses of FDA Approved HIV Protease Inhibitors," Synthesis, 2001, 2203-29.

Ghosh et al., "Antiviral Activity of UIC-PI, a Novel Inhibitor of the Human Immunodeficiency Virus Type 1 Protease," Antiviral Research, 2002, 54, 29-36.

Ghosh et al., "Stereoselective Photochemical 1,3-Dioxolane Addition to 5-Alkoxymethyl-2(5H)-furanone: Synthesis of Bis-tetrahydrofuranyl Ligand for HIV Protease Inhibitor UIC-94017 (TMC-114)," J. Org. Chem. 2004, 69, 7822-29.

H. Gatanaga et al., "Altered HIV-1 gag Protein Interactions with Cyclophilin A (CypA) on the Acquisitionof H219Qand H219P Substitutios in the CypA Binding Loop," J. Biol. Chem. 2006, 281, 1241.

Ghosh et al., "Bis-Tetrahydrofuran: A Privileged Ligand for Darunavir and a New Generation of HIV-Protease Inhibitors That Combat Drug-Resistance. Bis-Tetrahydrofuran," ChemMedChem 2006, 1, 939-950.

Ghosh et al., "A Stereoselective Anti-aldol Route to (3R,3aS,6aR)-Tetrahydro-2H-furo[2,3-b]furan-3-ol: A Key Ligand for a New Generation of HIV Protease Inhibitors," Synthesis 2006, 3015-3019.

Tie et al., "Atomic Resolution crystal Structures of HIV-1 Protease and MutantsV82A and I84V with Saquinavir," Proteins 2007, 67, 232-242.

Toth et al. "A Simple, Continuous Fluorometric Assay for HIV Protease," Int. J. Peptide Protein Res. 1990, 36, 544-550.

Wang et al., "Potent New Antiviral Compound Shows Similar inhibition and Structural Interactions with Drug Resistant Mutants and Wild Type HIV-1 Protease," J. Med. Chem. 2007, 50, 4509.

Koh et al., "Potent Inhibition of HIV-1 Replication by Novel Nonpeptidyl Small Molecule Inhibitors of Protease Dimerization," J. Biol. Chem. 2007, 282, 28709.

Ghosh et al., "Darunavir, a Conceptually New HIV-1 Protease Inhibitor for the Treatment of Drug-resistant HIV," Bioorg. Med. Chem. 2007, 15, 7576.

Mitsuya et al., "Development of Protease Inhibitors and the Fight with Drug-Resistant HIV-1 Variants," Advances in Pharmacology, 2007, 56, 169-197.

Ghosh et al., "Design of HIV Protease Inhibitors Targeting Protein Backbone: An Effective Strategy for Combating Drug Resistance," Acc. Chem. Res. 2008, 41, 78-86.

Ghosh et al., "Enantioselective Synthesis of Cyclopentyltetrahydrofuran (Cp-THF), an Important High-Affinity P2-Ligand for HIV-1 Protease Inhibitors," Tet. Lett. 2008, 49, 3409-2412.

Ghosh et al., "Potent HIV-1 Protease Inhibitors Incorporating meso-Bicyclic Urethanes as P2-ligands: Structure-Based Design, Synthesis, Biological Evaluation and Protein-Ligand X-Ray Studies," Org. Biomol. Chem., 2008, 6, 3703-3713.

Liu et al., "Effect of Flap Mutations on Structure of HIV-1 Protease and Inhibition by Saquinavir and Darunavir," J. Mol. Biol. 2008, 381, 102-115.

Ghosh et al., "Flexible Cyclic Ethers/Polyethers as Novel P2-Ligands for HIV-1 Protease Inhibitors: Design, Synthesis, Biological Evaluation and Protein-ligand X-ray Studies," J. Med. Chem. 2008, 51, 6021-33.

Kovalevsky et al., "Solution Kinetics Measurements Suggest HIV-1 Protease Has Two Binding Sites for Darunavir and Amprenavir," J. Med. Chem. 2008, 51, 6599-03.

Kovalevsky et al., "Structural Evidence for Effectiveness of Darunavir and Two Related Antiviral Inhibitors against HIV-2 Protease," J.Mol. Biol. 2008, 384, 178-192.

Ghosh et al., "Design and Synthesis of Stereochemically Defined Novel Spirocyclic P-2-Ligands for HIV-1 Protease Inhibitors," Org. Lett. 2008, 10, 5135-38.

Koh et al., "GRL-02031: A Novel Nonpeptide Protease Inhibitor (PI) Containing a Stereochemistry Defined Fused Cyclopentanyltetrahydrofuran (Cp-THF) Potent Against Multi-PI-Resistant HIV-1 In Vitro," Antimicrobial Agents Chemother. 2009, 53, 987-996.

Ghosh et al., "Harnessing Nature's Insight: Design of Aspartyl Protease Inhibitors from Treatment of Drug-Resistant HIV to Alzheimer's Disease," J. Med. Chem. 2009, 52(8), 2163-2176.

Ghosh et al., "Design of HIV-1 Protease Inhibitors with Pyrrolidinones and Oxazolidinones as Novel P1'-Ligands to Enhance Backbone-binding interactions with Protease: Synthesis, Biological Evaluation and Protein-ligand X-ray Studies," J. Med. Chem. 2009, 52, 3902-3914.

Ghosh et al., "Structure-Based Design, Synthesis, and Biological Evaluation of a Series of Novel and Reversible Inhibitors for the Severe Acute Respiratory Syndrome—Coronavirus Papain-Like Protease," J. Med. Chem. 2009, 52 (16), 5228-5240.

Ghosh et al., Design, Synthesis, Protein-Ligand X-ray Structure, and Biological Evaluation of a Series of Novel Macrocyclic Human Immunodeficiency Virus-1 Protease Inhibitors to Combat Drug Resistance J. Med. Chem. 2009, 52 (23), 7689-7705.

Das et al.,"Prediction of Potency of Protease Inhibitors Using Free Energy Simulations with Polarizable Quantum Mechanics-Based Ligand Charges and a Hybrid Water Model," J. Chem. Info. Model, 2009, 49, 2851-2862.

Ghosh et al.,"Synthesis and biological evaluation of novel allophenylnorstatine-based HIV-1 protease inhibitors incorporating high affinity P2-ligands," Bioorg. Med. Chem. Lett. 2010, 20, 1241-1246.

Clementz et al., "Deubiquitinating and Interferon Antagonism Activities of Coronavirus Papain-Like Proteases," J. Virol. 2010, 84, 4619-4629.

Tojo et al.,"Novel Protease Inhibitors (PIs) Containing Macrocyclic Components and 3(R),3a(S),6a(R)-bis-Tetrahydrofuranylurethane (bis-THF) That Are Potent Against Multi-PI-Resistant HIV-1 Variants In Vitro," Antimicrobial Agents and Chemotherapy, 2010, 54, 3460-3470.

Ghosh et al., "Severe Acute Respiratory Syndrome Coronavirus Papain-like Novel Protease Inhibitors: Design, Synthesis, Protein-Ligand X-ray Structure and Biological Evaluation," J. Med. Chem. 2010, 53, 4968-4979.

Ghosh et al., "Darunavir (Prezista): A HIV-1 Protease Inhibitor for Treatment of Multidrug-Resistant HIV," Modern Drug Synthesis, Wiley, Edited by J. J. Li and D. S. Johnson, 2010, 29-44.

Ghosh et al., "Probing Multidrug-Resistance and Protein-Ligand Interactions with Oxatricyclic Designed Ligands in HIV-1 Protease Inhibitors,"ChemMedChem, n/a. doi: 10.1002/cmdc.201000318.

Amano et al., "A Novel Bis-Tetrahydrofuranylurethane-containing Nonpeptidic Protease Inhibitor (PI), GRL-98065, is Potent against Multiple-PI-Resistant Human Immunodeficiency Virus In Vitro," Antimicrobial Agents and Chemotherapy, vol. 51, No. 6, 2143-2155 (2007).

Ghosh et al., "TiCl4 Promoted Multicomponent Reaction: A New Entry to the Functionalized α-Amino Acids," Organic Letters, vol. 7, 2005, p. 7-10.

C.B. Hicks et al., "Durable efficacy of tipranavir-ritonavir in combination with an optimised background regimen of antiretroviral drugs for treatment-experienced HIV-1-infected patients at 48 weeks in the Randomized Evaluation of Strategic Intervention in multi-drug reSistant patients with Tipranavir (RESIST) studies: an analysis of combined data from two randomised open-label trials," The Lancet, 2006, 368, 466-475.

HIV PROTEASE INHIBITORS AND METHODS FOR USING

CROSS-REFERENCE TO RELATED APPLICATIONS

This application is a U.S. national application under 35 U.S.C. §371(b) of International Application Serial No. PCT/US2009/049937 filed Jul. 8, 2009, which claims priority to U.S. Provisional Patent Application Ser. No. 61/079,237, filed Jul. 9, 2008. The disclosure of both of which are incorporated herein by reference in their entirety.

GOVERNMENT RIGHTS

This invention was made with government support under GM053386 awarded by the NIH. The government has rights in this invention.

TECHNICAL FIELD

This invention relates to inhibitors of HIV proteolytic enzymes and their use in treating HIV, HIV/AIDS, and HIV-related infections. In particular, this invention relates to inhibitors of HIV proteolytic enzymes that include functional groups capable of adapted interactions with the enzymes.

BACKGROUND AND SUMMARY OF THE INVENTION

The introduction of protease inhibitors (PIs) into highly active antiretroviral therapy (HAART), a combination therapy based on co-administration of PIs with reverse-transcriptase inhibitors, has marked the beginning of a new era in HIV/AIDS chemotherapy. HAART treatment regimens have led to a significant decline in the number of deaths due to HIV infection in the developed World. Unfortunately there are a number of factors that severely limit current HAART treatment regimens. High frequency of dosing, heavy pill burden and issues of tolerability and toxicity can lead to poor adherence to treatment. The need for more potent, less toxic drug regimens is quite apparent.

It is the rapid emergence of drug resistance however, that is proving to be the most formidable problem. Mutations causing drug resistance are thought to occur spontaneously, through the recombination of mixed viral populations, and also due to drug pressure, particularly when administered at sub-standard doses. There is ample evidence that these viral strains can be transmitted. Thus, the development of new antiretroviral agents, including those able to maintain potency against resistant HIV strains has become an urgent priority.

The proteolytic enzyme, HIV-1 protease has been reported to be essential for viral assembly and maturation. As a consequence, design of specific inhibitors for HIV-1 protease has become the subject of widespread interest. In 1996, protease inhibitors (PIs) were introduced in combination with reverse transcriptase inhibitors to become highly active antiretroviral therapy (HAART). This treatment regimen significantly increased life expectancy, improved quality of life and decreased mortality and morbidity among HIV/AIDS patients. Despite these notable advances, the emergence of drug-resistant HIV-1 variants is severely limiting the efficacy of HAART treatment regimens. Therefore, development of new broad spectrum antiretroviral drugs that produce minimal adverse effects remains an important therapeutic objective for the treatment of HIV/AIDS (Wainberg, M. A.; 1998; Grabar, S.; et al., AIDS, 2000, 14, 141; Hertogs, K., 2000; the disclosure of the foregoing is incorporated herein in its entirety by reference). The entirety of the disclosures of each of the documents cited herein are also incorporated herein by reference. The structure-based design and development of a series of novel HIV-1 protease inhibitors including Darunavir, TMC-126, and GRL-06579A (compound 101) has recently been described (Surleraux, D. L. N. G.; et al., J. Med. Chem., 2005, 48, 1813; Koh, Y.; et al., Antimicrob. Agents Chemother., 2003, 47, 3123; Ghosh, A. K.; et al., Antiviral Res., 2002, 54, 29; Ghosh, A. K.; et al., Bioorg. Med. Chem. Lett., 1998, 8, 687; Yoshimura, K.; et al., J. Virol., 2002, 76, 1349). These inhibitors exhibited marked potency in enzyme inhibitory and cell culture assays. Furthermore, these inhibitors have shown activity against a broad spectrum of HIV isolates including a variety of multi-PI resistant clinical strains. Darunavir has been recently approved for the therapy of HIV/AIDS patients who are harboring drug-resistant HIV and do not respond to other antiretroviral drugs. Nevertheless, additional options are needed for the treating physician to use instead of, or in conjunction with currently known therapies.

In one embodiment, a compound of the formula

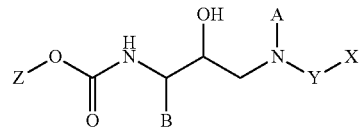

or a pharmaceutically acceptable salt thereof is described; wherein

A and B are each independently selected from alkyl, heteroalkyl, cycloalkyl, heterocyclyl, optionally substituted amino alkyl, arylalkyl, heteroarylalkyl, and arylthioalkyl, each of which is optionally substituted;

X is optionally substituted alkyl, optionally substituted cycloalkyl, optionally substituted heterocycle, optionally substituted aryl, or optionally substituted heteroaryl;

Y is C(O), SO$_2$, or an optionally substituted alkylene;

Z is an optionally substituted C$_{7-16}$ cycloalkyl, an optionally substituted C$_{7-16}$ heterocycle, or a radical of the formula

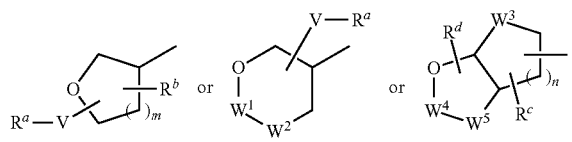

where n is 0, 1, or 2;
m is 0, 1, 2, 3, or 4;
V is oxygen, optionally substituted nitrogen, or SO$_2$;
R$^a$ and R$^b$ are each independently selected from the group consisting of hydrogen, optionally substituted alkyl, optionally substituted heteroalkyl, and optionally substituted arylalkyl;
or R$^a$ and R$^b$ are taken together to form an optionally substituted heterocycle;
providing that V—R$^a$ and the ring oxygen are not attached to the same atom;
R$^c$ and R$^d$ are each independently selected from the group consisting of hydrogen, optionally substituted alkyl, optionally substituted arylalkyl, hydroxyl, optionally substituted alkoxy, optionally substituted arylalkoxy, and optionally substituted amino;

W¹ is a bond, an optionally substituted alkylene, or an optionally substituted nitrogen;

W² is selected from the group of divalent radicals consisting of optionally substituted alkylene, oxygen, sulfur, optionally substituted nitrogen, SO₂, and an optionally substituted heterocycle, and combinations thereof;

providing that W² does not include —O—O— or —O—S—;

W³ is optionally substituted alkylene or oxygen;

W⁴ is a bond, an optionally substituted alkylene, or an optionally substituted nitrogen;

W⁵ is selected from the group of divalent radicals consisting of optionally substituted alkylene, oxygen, sulfur, optionally substituted nitrogen, SO₂, and optionally substituted fused heterocycle;

providing that W⁵ does not include —O—O— or —O—S—; and providing that if all of W³, W⁴, and W⁵ are optionally substituted alkylene, at least one of $R^c$ or $R^d$ is hydroxyl, alkoxy, or optionally substituted amino.

In another embodiment pharmaceutical compositions are described, where the compositions include one or more of the compounds described herein in a therapeutically effective amount for treating an HIV infection, AIDS, or an AIDS-related disease. In another embodiment, the pharmaceutical compositions described herein also include one or more carriers, diluents, or excipients, or a combination thereof. In another embodiment, methods for treating a patient in need of relief from an HIV infection is described, where the methods include the step of administering to the patient a therapeutically effective amount of one or more of the compounds or pharmaceutical compositions described herein.

DETAILED DESCRIPTION

In another embodiment of the invention, compound of formula I is described

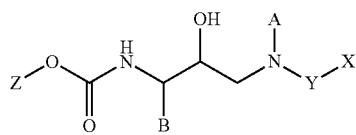

I or a pharmaceutically acceptable salt thereof;
wherein

A is alkyl, heteroalkyl, cycloalkyl, heterocyclyl, optionally substituted amino alkyl, arylalkyl, heteroarylalkyl, or arylthioalkyl, each of which is optionally substituted;

B is alkyl, heteroalkyl, cycloalkyl, heterocyclyl, haloalkyl, optionally substituted amino alkyl, arylalkyl, heteroarylalkyl, or arylthioalkyl, each of which is optionally substituted;

X is optionally substituted alkyl, optionally substituted cycloalkyl, optionally substituted heterocycle, optionally substituted aryl, or optionally substituted heteroaryl;

Y is C(O), SO₂, or an optionally substituted alkylene;

Z is an optionally substituted $C_{7-16}$ cycloalkyl, an optionally substituted $C_{7-16}$ heterocycle, or a radical of the formula

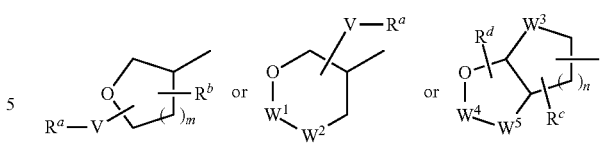

n is 0, 1, or 2;
m is 0, 1, 2, 3, or 4;
V is oxygen, optionally substituted nitrogen, or SO₂;
$R^a$ and $R^b$ are each independently selected from the group consisting of hydrogen, optionally substituted alkyl, and optionally substituted arylalkyl;

or $R^a$ and $R^b$ are taken together to form an optionally substituted heterocycle;

providing that V—$R^a$ and the ring oxygen are not attached to the same atom;

$R^c$ and $R^d$ are each independently selected from the group consisting of hydrogen, optionally substituted alkyl, optionally substituted arylalkyl, hydroxyl, optionally substituted alkoxy, optionally substituted arylalkoxy, and optionally substituted amino;

W¹ is a bond, an optionally substituted alkylene, or an optionally substituted nitrogen;

W² is selected from the group of divalent radicals consisting of optionally substituted alkylene, oxygen, sulfur, optionally substituted nitrogen, SO₂, and an optionally substituted heterocycle, and combinations thereof;

providing that W² does not include —O—O— or —O—S—;

W³ is optionally substituted alkylene or oxygen;

W⁴ is a bond, an optionally substituted alkylene, or an optionally substituted nitrogen;

W⁵ is selected from the group of divalent radicals consisting of optionally substituted alkylene, oxygen, sulfur, optionally substituted nitrogen, SO₂, and optionally substituted fused heterocycle;

providing that W⁵ does not include —O—O— or —O—S—; and providing that if all of W³, W⁴, and W⁵ are optionally substituted alkylene, at least one of $R^c$ or $R^d$ is hydroxyl, alkoxy, or optionally substituted amino.

In another embodiment compounds of formula I are described

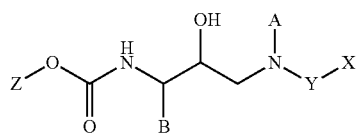

I wherein

A is alkyl, heterocyclylalkyl, haloalkyl, substituted amino alkyl, optionally substituted arylalkyl, or optionally substituted arylthioalkyl; and B is alkyl, haloalkyl, substituted amino alkyl, heterocyclylalkyl, optionally substituted arylalkyl, or optionally substituted arylthioalkyl;

or B and X are taken together to form an optionally substituted heterocycle;

X is optionally substituted cycloalkyl, optionally substituted heterocycle, optionally substituted aryl;

Y is C(O), SO₂, or an optionally substituted alkylene;

Z is an optionally substituted $C_{7-16}$ cycloalkyl, an optionally substituted $C_{7-16}$ heterocycle, or a radical of the formula

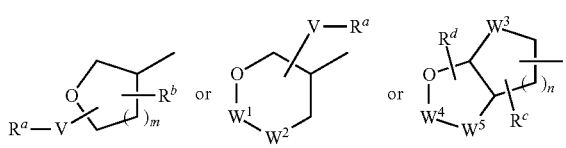

n is 0, 1, or 2;
m is 0, 1, 2, 3, or 4;
V is oxygen, optionally substituted nitrogen, or $SO_2$;
$R^a$ and $R^b$ are each independently selected from the group consisting of hydrogen, optionally substituted alkyl, and optionally substituted arylalkyl;
or $R^a$ and $R^b$ are taken together to form an optionally substituted heterocycle;
providing that V—$R^a$ is not geminal to the ring oxygen;
$R^c$ and $R^d$ are each independently selected from the group consisting of hydrogen, optionally substituted alkyl, optionally substituted arylalkyl, hydroxyl, optionally substituted alkoxy, optionally substituted arylalkoxy, and optionally substituted amino;
$W^1$ is optionally substituted alkylene or optionally substituted nitrogen;
$W^2$ is selected from the group of divalent radicals consisting of optionally substituted alkylene, oxygen, sulfur, optionally substituted nitrogen, $SO_2$, and an optionally substituted heterocycle, and combinations thereof;
providing that $W^2$ does not include —O—O— or —O—S—;
$W^3$ is optionally substituted alkylene or oxygen;
$W^4$ is optionally substituted alkylene or optionally substituted nitrogen;
$W^5$ is selected from the group of divalent radicals consisting of optionally substituted alkylene, oxygen, sulfur, optionally substituted nitrogen, $SO_2$, and optionally substituted fused heterocycle;
providing that $W^5$ does not include —O—O— or —O—S—; and providing that if all of $W^3$, $W^4$, and $W^5$ are optionally substituted alkylene, at least one of $R^c$ or $R^d$ is hydroxyl, alkoxy, or optionally substituted amino.

In another embodiment, A is haloalkyl. In another embodiment, B is haloalkyl.

In another embodiment, $R^a$ and $R^b$ are each independently selected from the group consisting of hydrogen, optionally substituted alkyl, and optionally substituted arylalkyl; or $R^a$ and $R^b$ are taken together to form an optionally substituted heterocycle;

In another embodiment compound of formula I is described wherein V is a nitrogen substituted with alkyl or arylalkyl.

In another embodiment a compound of formula I is described wherein $W^1$ is methylene and $W^2$ is oxygen, alkylene or polyether.

In another embodiment a compound of formula I is described wherein $W^2$ represents between 1 and 11 divalent radicals each independently selected from the group consisting of optionally substituted alkylene, oxygen, sulfur, optionally substituted nitrogen, and $SO_2$.

In another embodiment a compound of formula I is described wherein $W^1$ and $W^2$ and the attached atoms form an optionally substituted 5- to 14-membered heterocycle.

In another embodiment a compound of formula I is described wherein $W^2$ is an optionally substituted heterocycle.

In another embodiment a compound of formula I is described wherein $W^5$ represents between 1 and 11 divalent radicals each independently selected from the group consisting of optionally substituted alkylene, oxygen, sulfur, optionally substituted nitrogen, and $SO_2$;

In another embodiment a compound of formula I is described wherein $W^4$ and $W^5$ and the attached atoms form an optionally substituted 5- to 14-membered heterocycle.

In another embodiment a compound of formula I is described wherein $W^5$ represents an optionally substituted heterocycle.

In another embodiment a compound of formula I is described wherein $W^3$ is methylene and $W^4$ is oxygen.

In another embodiment a compound of formula I is described wherein $R^a$ and $R^b$ are taken together to form an optionally substituted nitrogen-containing or oxygen-containing heterocycle.

In another embodiment a compound of formula I is described wherein $R^a$ and $R^b$ are taken together to form an optionally substituted heterocycle containing $SO_2$.

In another embodiment a compound of formula I is described wherein $R^a$ and $R^b$ are taken together to form an optionally substituted heterocycle containing C(O)O, $SO_2$NH, S, C(O)NH, or NH—O.

In another embodiment a compound of formula I is described wherein $R^a$ and $R^b$ are taken together to form an optionally substituted ring containing C(O), CHF—C(O), or $CF_2$—C(O).

In another embodiment a compound of formula I is described wherein $R^a$ and $R^b$ are taken together to form a divalent fragment of the formula

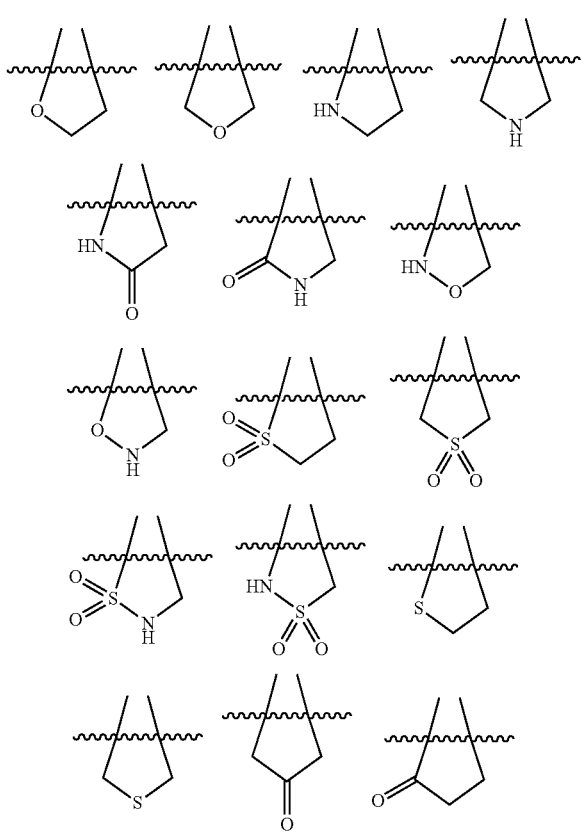

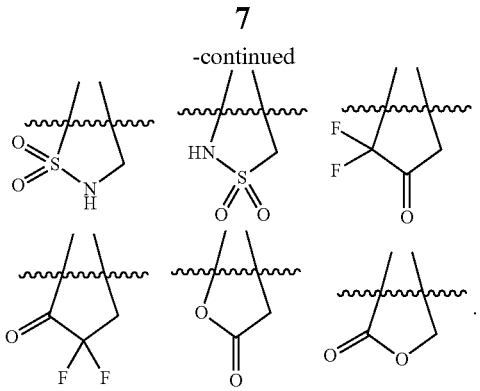

In another embodiment a compound of formula I is described wherein $W^3$ and $W^4$ are methylene, and $R^c$ is oxygen.

In another embodiment a compound of formula I is described wherein $W^3$ and $W^4$ are methylene, and $R^d$ is oxygen.

In another embodiment a compound of formula I is described wherein A is branched alkyl or optionally substituted arylalkyl.

In another embodiment a compound of formula I is described wherein B is branched alkyl or optionally substituted arylalkyl.

In another embodiment a compound of formula I is described wherein A is heterocyclylalkyl, where the heterocycle is an optionally substituted furan, pyran, or lactam.

In another embodiment a compound of formula I is described wherein B is heterocyclylalkyl, where the heterocycle is an optionally substituted furan, pyran, or lactam.

In another embodiment Y is $SO_2$.

In another embodiment a compound of formula I is described wherein Y is alkylene.

In another embodiment a compound of formula I is described wherein Y is branched alkylene.

In another embodiment a compound of formula I is described wherein Y is methylene.

In another embodiment a compound of formula I is described wherein Y is alkylene substituted with aryl.

In another embodiment, X is an aryl group. In another embodiment, X is a phenyl group substituted with one or more electron donating groups. In another embodiment X is a phenyl group substituted with a methoxy group.

In another embodiment a compound of formula I is described wherein X is alkyl, cycloalkyl, heterocycle, or aryl, each of which is optionally substituted.

In another embodiment a compound of formula I is described wherein X is fluoroakyl or fluoroaryl.

In another embodiment a compound of formula I is described wherein X is heterocycle fused aryl.

In another embodiment a compound of formula I is described wherein B and Z are taken together to form a optionally substituted heterocycle fused aryl.

In another embodiment a method of treating a patient in need of relief from infection by HIV is described, the method comprising providing the patient with a composition comprising a therapeutically effective amount of a compound of formula I

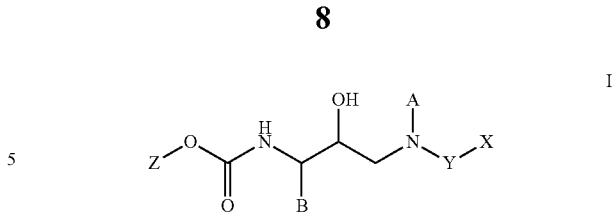

wherein

A is alkyl, heterocyclylalkyl, haloalkyl, substituted amino alkyl, optionally substituted arylalkyl, or optionally substituted arylthioalkyl; and B is alkyl, haloalkyl, substituted amino alkyl, heterocyclylalkyl, optionally substituted arylalkyl, or optionally substituted arylthioalkyl;

or B and X are taken together to form an optionally substituted heterocycle;

X is optionally substituted cycloalkyl, optionally substituted heterocycle, optionally substituted aryl;

Y is C(O), $SO_2$, or an optionally substituted alkylene;

Z is an optionally substituted $C_{7-16}$ cycloalkyl, an optionally substituted $C_{7-16}$ heterocycle, or a radical of the formula

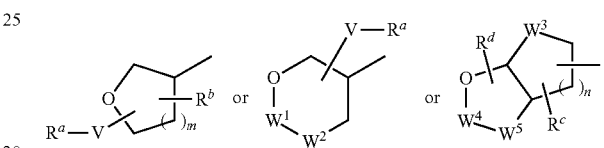

n is 0, 1, or 2;

m is 0, 1, 2, 3, or 4;

V is oxygen, optionally substituted nitrogen, or $SO_2$;

$R^a$ and $R^b$ are each independently selected from the group consisting of hydrogen, optionally substituted alkyl, and optionally substituted arylalkyl;

or $R^a$ and $R^b$ are taken together to form an optionally substituted heterocycle;

providing that V—$R^a$ is not geminal to the ring oxygen;

$R^c$ and $R^d$ are each independently selected from the group consisting of hydrogen, optionally substituted alkyl, optionally substituted arylalkyl, hydroxyl, optionally substituted alkoxy, optionally substituted arylalkoxy, and optionally substituted amino;

$W^1$ is optionally substituted alkylene or optionally substituted nitrogen;

$W^2$ is selected from the group of divalent radicals consisting of optionally substituted alkylene, oxygen, sulfur, optionally substituted nitrogen, $SO_2$, and an optionally substituted heterocycle, and combinations thereof;

providing that $W^2$ does not include —O—O— or —O—S—;

$W^3$ is optionally substituted alkylene or oxygen;

$W^4$ is optionally substituted alkylene or optionally substituted nitrogen;

$W^5$ is selected from the group of divalent radicals consisting of optionally substituted alkylene, oxygen, sulfur, optionally substituted nitrogen, $SO_2$, and optionally substituted fused heterocycle;

providing that $W^5$ does not include —O—O— or —O—S—; and providing that if all of $W^3$, $W^4$, and $W^5$ are optionally substituted alkylene, at least one of $R^c$ or $R^d$ is hydroxyl, alkoxy, or optionally substituted amino.

In this and other embodiments described herein, it is understood that the compounds may be neutral or may be one or more pharmaceutically acceptable salts, crystalline forms, non crystalline forms, hydrates, or solvates, or a combination of the foregoing. Accordingly, all references to the compounds described herein may refer to the neutral molecule, and/or those additional forms thereof collectively and individually from the context.

The phrase "optionally substituted amino" as used herein includes unsubstituted amino, alkylamino, dialkylamino, heteroalkylamino, di(heteroalkyl)amino, alkyl(cycloalkyl)amino, cycloalkylamino, di(cycloalkyl)amino, heteroalkyl(alkyl)amino, arylalkylamino, arylamino, aryl(alkyl)amino, heteroarylamino, heteroaryl(alkyl)amino, heterocyclylamino, alkyl(heterocyclyl)amino, and the like.

The term "cycloalkyl" as used herein includes molecular fragments or radicals comprising a bivalent chain of carbon atoms, at least a portion of which forms a ring. It is to be understood that the term cycloalkyl as used herein includes fragments and radicals attached at either ring atoms or non-ring atoms, such as, such as cyclopropyl, cyclohexyl, 3-ethylcyclopent-1-yl, cyclopropylethyl, cyclohexylmethyl, and the like.

The term "cycloalkenyl" as used herein refers to a monovalent chain of carbon atoms containing one or more unsaturated bonds, at least a portion of which forms a ring.

The term "cycloalkylene" as used herein includes molecular fragments or radicals comprising a bivalent chain of carbon atoms, at least a portion of which forms a ring. It is to be understood that the term cycloalkyl as used herein includes fragments and radicals attached at either ring atoms or non-ring atoms, such as cycloprop-1,1-diyl, cycloprop-1,2-diyl, cyclohex-1,4-diyl, 3-ethylcyclopent-1,2-diyl, 1-methylenecyclohex-4-yl, and the like.

The terms "heteroalkyl" and "heteroalkylene" as used herein includes molecular fragments or radicals comprising monovalent and divalent, respectively, groups that are formed from a linear or branched chain of carbon atoms and heteroatoms, wherein the heteroatoms are selected from nitrogen, oxygen, and sulfur, such as alkoxyalkyl, alkyleneoxyalkyl, aminoalkyl, alkylaminoalkyl, alkyleneaminoalkyl, alkylthioalkyl, alkylenethioalkyl, alkoxyalkylaminoalkyl, alkylaminoalkoxyalkyl, alkyleneoxyalkylaminoalkyl, and the like. It is to be understood that neither heteroalkyl nor heteroalkylene includes oxygen-oxygen fragments. It is also to be understood that neither heteroalkyl nor heteroalkylene includes oxygen-sulfur fragments, unless the sulfur is oxidized as S(O) or $S(O)_2$.

As used herein, the term "haloalkyl" includes an alkyl group wherein one or more hydrogen atoms is replaced with a halogen atom, independently selected in each instance from the group consisting of fluorine, chlorine, bromine and iodine. Non-limiting, illustrative examples include, difluoromethlyl, 2,2,2-trifluoroethyl, 2-chlorobutyl, 2-chloro-2-propyl, trifluoromethyl, bromodifluoromethyl, and the like.

The term "heterocyclyl" as used herein includes molecular fragments or radicals comprising a monovalent chain of carbon atoms and heteroatoms, wherein the heteroatoms are selected from nitrogen, oxygen, and sulfur, at least a portion of which, including at least one heteroatom, form a ring, such as aziridine, pyrrolidine, oxazolidine, 3-methoxypyrrolidine, 3-methylpiperazine, and the like, and wherein the fragment or radical may contain one or more unstaturated bonds. Accordingly, as used herein, heterocyclyl includes alkylheterocyclyl, heteroalkylheterocyclyl, heterocyclylalkyl, heterocyclylheteroalkyl, and the like. It is to be understood that the term heterocyclyl as used herein includes fragments and radicals attached at either ring atoms or non-ring atoms, such as tetrahydrofuran-2-yl, piperidin-1-yl, piperidin-4-yl, piperazin-1-yl, morpholin-1-yl, tetrahydrofuran-2-ylmethyl, piperidin-1-ylethyl, piperidin-4-ylmethyl, piperazin-1-ylpropyl, morpholin-1-ylethyl, and the like. It is also understood that The term "aryl" as used herein includes molecular fragments or radicals comprising an aromatic mono or polycyclic ring of carbon atoms, such as phenyl, naphthyl, and the like.

The term "heteroaryl" as used herein includes molecular fragments or radicals comprising an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein includes molecular fragments or radicals comprising aryl or heteroaryl substituted with one or more substituents, such as alkyl, heteroalkyl, halo, hydroxy, amino, alkyl or dialkylamino, alkoxy, alkylsulfonyl, aminosulfonyl, carboxylate, alkoxycarbonyl, aminocarbonyl, cyano, nitro, and the like. It is to be understood that the alkyl groups in such substituents may be optionally substituted with halo.

The compounds described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The compounds described herein may be capable of existing as geometric isomers. Accordingly, it is to be understood that the present invention includes pure geometric isomers or mixtures of geometric isomers.

It is also appreciated that the compounds described herein may exist in unsolvated forms as well as solvated forms, including hydrated forms. In general, the solvated forms are equivalent to unsolvated forms and are encompassed within the scope of the present invention. The compounds described herein may exist in multiple crystalline or amorphous forms. In general, all physical forms are equivalent for the uses contemplated by the present invention and are intended to be within the scope of the present invention.

Darunavir (TMC-114, compound 1) is a new nonpeptidic PI that has been recently approved by the FDA for the treatment of antiretroviral therapy-experienced patients.

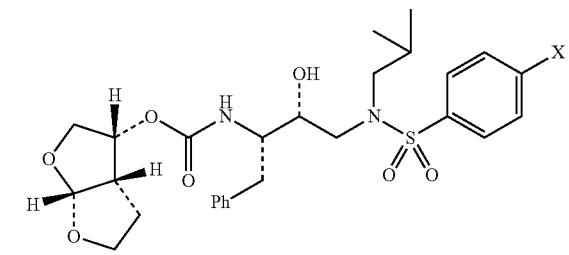

1 (darunavir, X = $NH_2$)
($K_i$ = 16 pM; $ID_{50}$ = 1.6 nM)
2 (TMC-126, X = OMe)
($K_i$ = 14 pM; $ID_{50}$ = 1.2 nM)

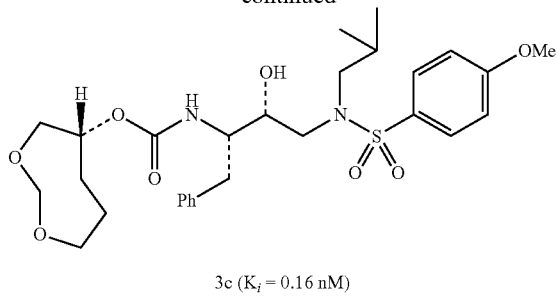

3c ($K_i$ = 0.16 nM)

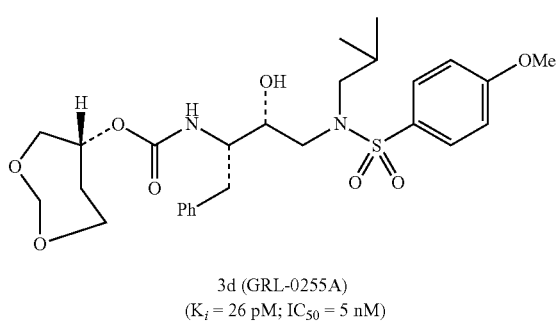

3d (GRL-0255A)
($K_i$ = 26 pM; $IC_{50}$ = 5 nM)

Inhibitor 1, and its related analogue 2 (TMC-126), are active against both wild-type and multi-drug resistant HIV strains. Both PIs demonstrated potent in vitro activity against viral isolates resistant to currently licensed PIs (Ghosh, A. K.; 1998; Koh, Y.; 2003; Surleraux, D. L. N. G.; 2005). Without being bound by theory, it is believed herein that maximizing active site interactions between the active site and the inhibitor, particularly hydrogen bonding interactions with the protein backbone may give rise to potent inhibitors retaining activity against mutant strains (see, for example, Yoshimura, K.; 2002; Koh, Y.; 2003; Ghosh, A. K.; 2002). Further, and without being bound by theory, it is believed herein that side chain amino acid mutations cannot easily disrupt inhibitor-backbone interactions, because the active site backbone conformation of mutant proteases is only minimally distorted compared to the wild-type HIV-1 protease (see, for example, Tie, Y.; et al., High-resolution crystal structures of HIV-1 protease with a potent non-peptide inhibitor (UIC-94017) active against multi-drug-resistant clinical strains. *J. Mol. Biol.* 2004, 338, 341-352; Hong, L.; et al., Crystal structure of an in vivo HIV-1 protease mutant in complex with saquinavir: Insights into the mechanisms of drug resistance. *Protein Sci.* 2000, 9, 1989-1904; Laco, G. S.; et al., Crystal Structures of the Inactive D30N Mutant of Feline Immunodeficiency Virus Protease Complexed with a Substrate and an Inhibitor. *Biochemistry* 1997, 36, 10696-10708). In this context, but without being bound by theory, it has been discovered herein that the fused bis-tetrahydrofuran (bis-THF) urethane of compounds 1 and 2 may be able to engage in a number of hydrogen bonding interactions with the backbone atoms of amino acids at the protease S2-site.

In another embodiment, the following compounds are described herein:

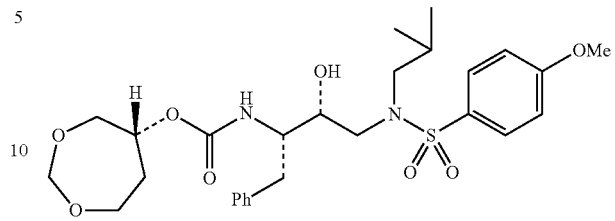

$K_i$ = 26 pM
Antiviral $IC_{50}$ = 4.5 nM

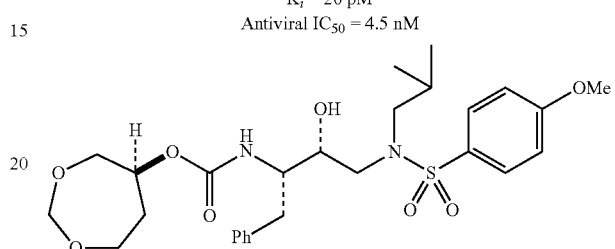

$K_i$ = 0.16 pM
Antiviral $IC_{50}$ = 29 nM

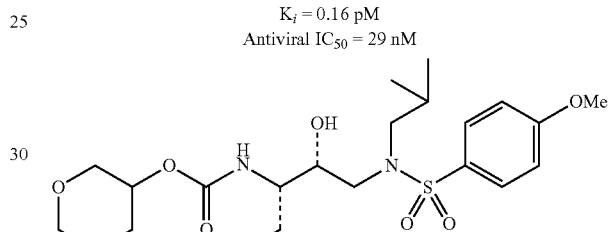

$K_i$ = 40 pM
Antiviral $IC_{50}$ = 4.1 nM

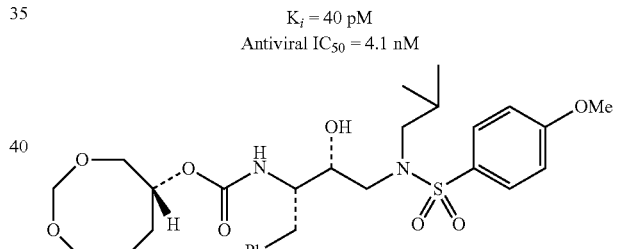

$K_i$ = 1.4M

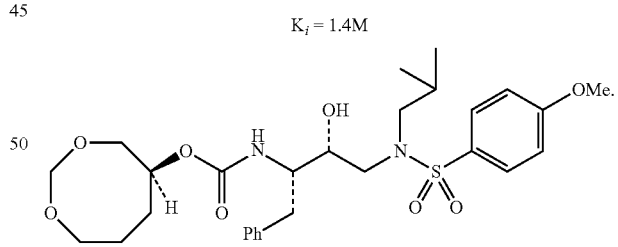

$K_i$ = 1.5M

Without being bound by theory, it is believed herein that an inhibitor interacting strongly with the protein backbone, while being able to accommodate amino acid side chain variations by means of repacking with a flexible ring, would maintain significant affinity against both wild-type and mutant enzymes. In another embodiment, a series of PIs is described that is based on the (R)-(hydroxyethylamino)sulfonamide isostere and bearing flexible cyclic ethers and polyethers as P2-ligands (compounds 3a-m, Table 1). For example, it is appreciated that compound 3c, incorporating a (1R)-3,5-dioxacyclooctan-1-yl urethane, may be considered as the flexible counterpart of the bis-THF moiety. In another embodiment, a series of structural variants of this inhibitor a described. Without being bound by theory, it is believed that those inhibitors contain polyether-based P2-ligands ranging from 6- to 13-membered rings coupled to a p-methoxyphenylsulfonamide as the P2'-ligand. The structure-based design, synthesis, and preliminary biological evaluation of inhibitors 3a-m is also described herein. It has been observed that among these inhibitors, 3d is the most potent with high enzyme inhibitory and antiviral activity ($K_i$=26 pM, $IC_{50}$=4.9 nM). In another embodiment, a protein-ligand X-ray structure of 3d-bound HIV-1 protease is described herein.

In another embodiment, the following substituted cyclic ethers are described:

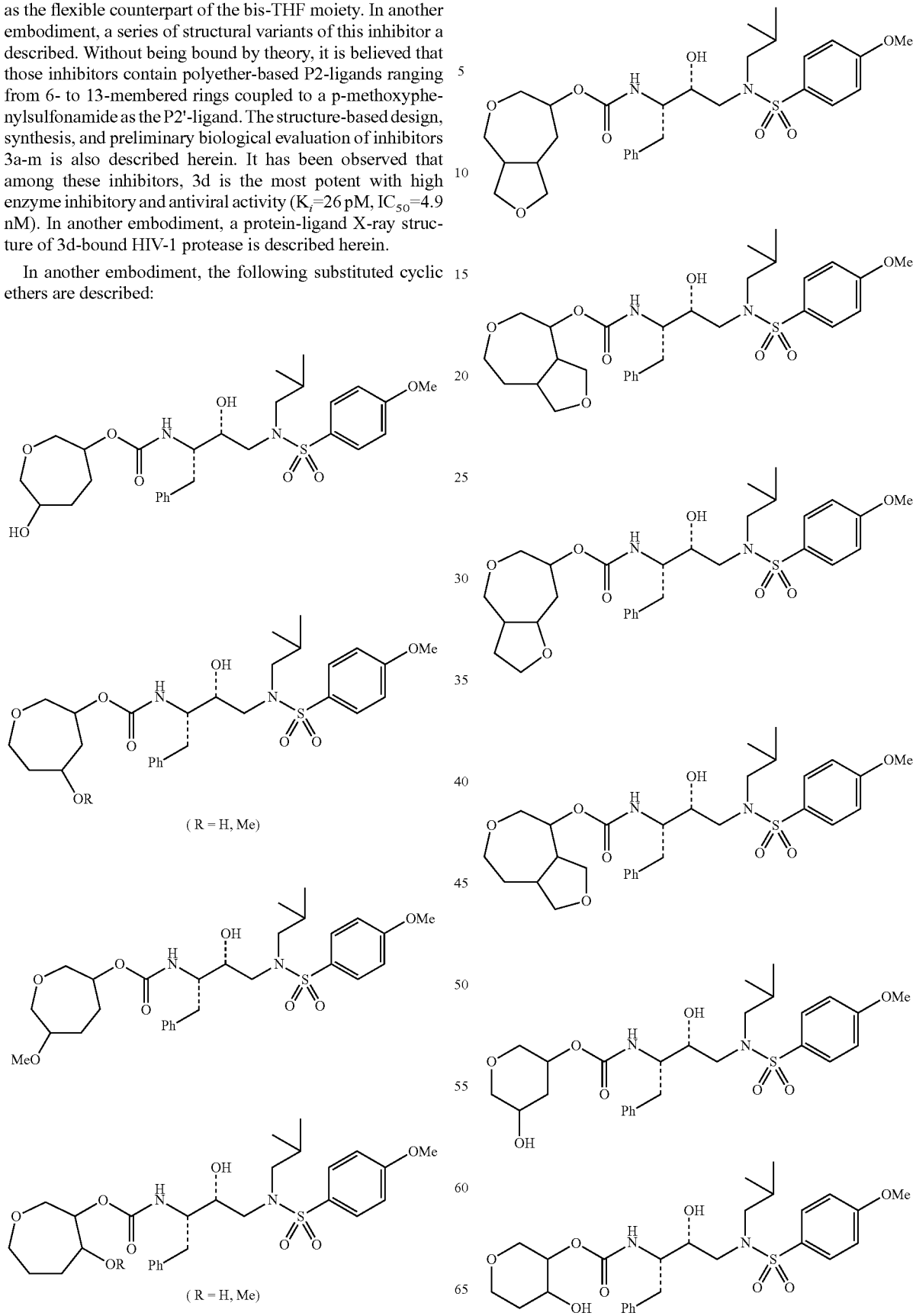

-continued

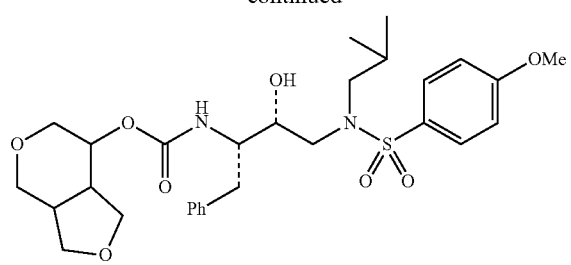

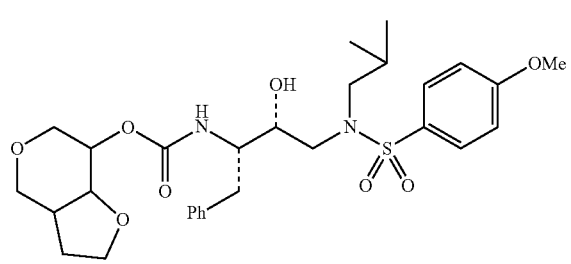

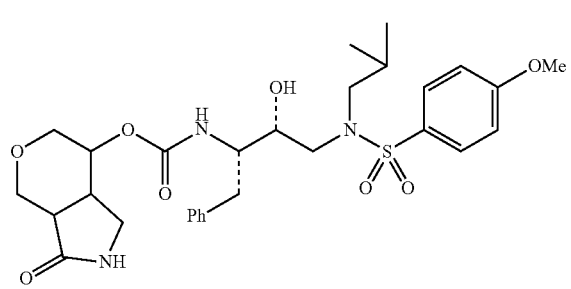

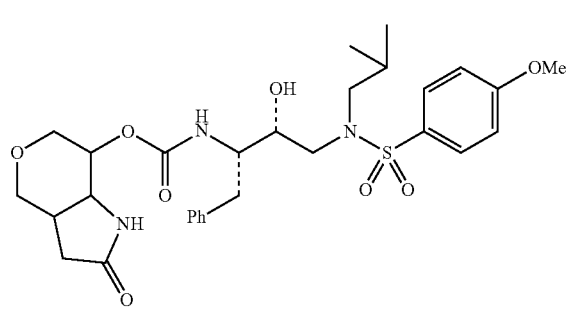

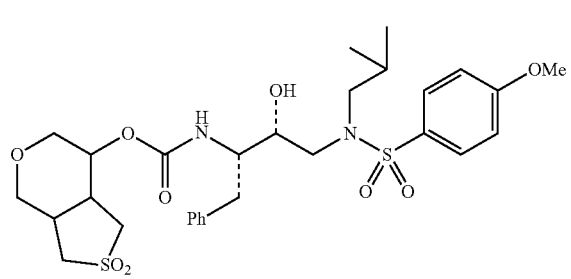

-continued

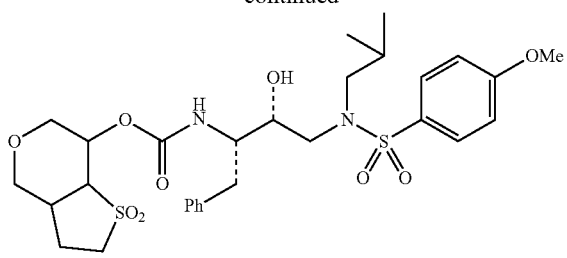

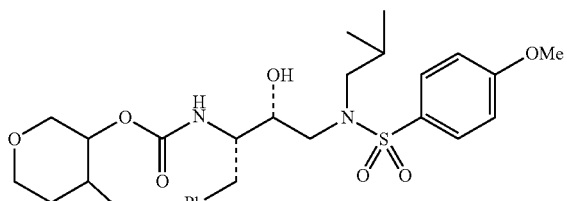

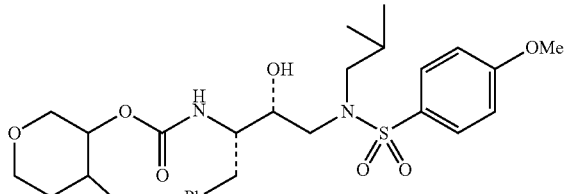

In another embodiment, inhibitors described herein contain a (R)-hydroxyethylamine sulfonamide isostere with a p-methoxysulfonamide as the P2'-ligand and various designed cyclic ethers and polyethers as the P2-ligands. In another embodiment, assays are described herein for evaluating compounds. Illustrative inhibitors described herein are initially evaluated in an enzyme inhibitory assay utilizing a protocol described by Toth and Marshall (Toth, M. V.; Marshall, G. R. A simple, continuous fluorometric assay for HIV protease. *Int. J. Pep. Protein Res.* 1990, 36, 544-550). Compounds that show potent enzymatic $K_i$ values may be further evaluated in an antiviral assay. The results for illustrative and representative compounds are shown in Table 1. The $K_i$-values denote the mean values of at least four determinations.

TABLE 1

Enzyme Inhibitory and Antiviral Activity of Inhibitors 3a-m

| Entry | Inhibitor | $K_i$ (nM) | $IC_{50}$ (nM)[a] |
|---|---|---|---|
| 1 | 3a | 0.15 ± 0.019 | nd[b] |
| 2 | 3b | 0.16 ± 0.04 | 30 ± 1 |
| 3 | 3c | 0.16 ± 0.011 | nd |
| 4 | 3d | 0.026 ± 0.012 | 4.9 + 0.3 |
| 5 | 3e | 0.81 ± 0.12 | nd |

TABLE 1-continued
Enzyme Inhibitory and Antiviral Activity of Inhibitors 3a-m
| Entry | Inhibitor | $K_i$ (nM) | $IC_{50}$ (nM)[a] |
|---|---|---|---|
| 6 | 3f | 0.74 ± 0.15 | nd |
| 7 | 3g | 27 ± 0.81 | nd |
| 8 | 3h | 0.041 ± 0.002 | 3.4 ± 0.7 |
| 9 | 3i | 16 ± 2.2 | nd |
| 10 | 3j | 33 ± 1.9 | nd |
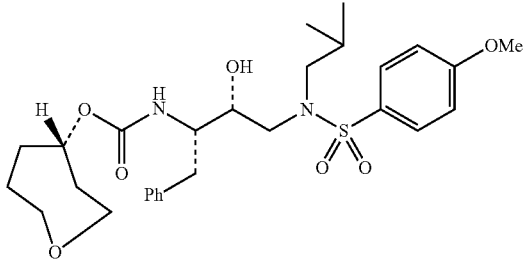
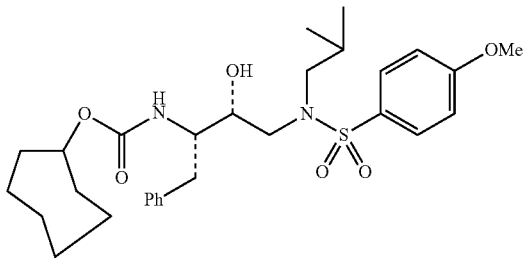 [SMILES: COc1ccc(S(=O)(=O)N(CC(C)C)C[C@@H](O)[C@H](Cc2ccccc2)NC(=O)OC2CCCCCC2)cc1]
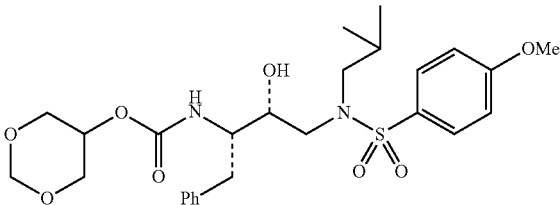 [SMILES: COc1ccc(S(=O)(=O)N(CC(C)C)C[C@@H](O)[C@H](Cc2ccccc2)NC(=O)OC2COCOC2)cc1]
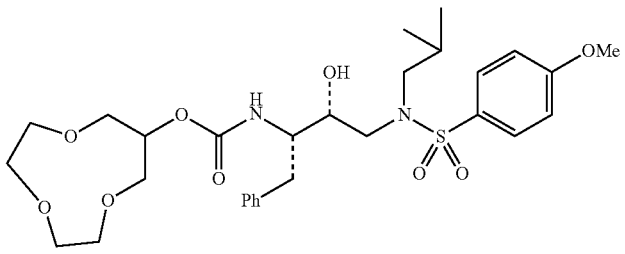 [SMILES: COc1ccc(S(=O)(=O)N(CC(C)C)C[C@@H](O)[C@H](Cc2ccccc2)NC(=O)OC2COCCOCCOC2)cc1]
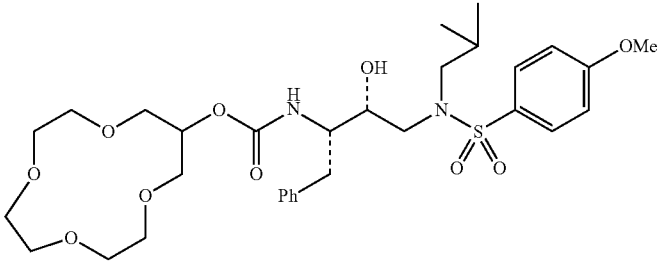 [SMILES: COc1ccc(S(=O)(=O)N(CC(C)C)C[C@@H](O)[C@H](Cc2ccccc2)NC(=O)OC2COCCOCCOCCOC2)cc1]

TABLE 1-continued

Enzyme Inhibitory and Antiviral Activity of Inhibitors 3a-m

| Entry | Inhibitor | $K_i$ (nM) | $IC_{50}$ (nM)[a] |
|---|---|---|---|
| 11 | 3k | 6.3 ± 0.57 | >1000 |
| 12 | 3l | 1.9 ± 0.2 | >1000 |
| 13 | 3m | 19 ± 0.76 | >1000 |
| SQV[c] | — | — | 16 ± 3 |
| APV[d] | — | — | 27 ± 6 |

[a]MT-2 human T-lymphoid cells exposed to HIV-1-LAI;
[b]nd = not determined;
cSQV = saquinavir;
[d]APV = amprenavir.

In another embodiment, sub-nanomolar inhibitors are described that result from the introduction of the 8-membered (S)- or (R)-1,3-dioxacyclooctan-5-yl urethanes as P2-ligands (inhibitors 3a and 3c). It has been observed herein that these inhibitors are less potent than inhibitor 2 that contains the bis-THF ligand. Incorporation of a (5R)-1,3-dioxacycloheptan-5-yl urethane as the P2-ligand resulted in the most potent inhibitor 3d in this series with a $K_i$ value of 26 pM. Without being bound by theory, it is believed that the 7-membered 1,3-dioxepanyl-ligand with R-configuration may bind to residues in the S2-site similar to bis-THF ligand of inhibitor 2. Inhibitor 3d exhibited more than 6-fold potency increase relative to epimeric (5S)-1,3-dioxacycloheptan-5-yl urethane 3b. Without being bound by theory, it is believed that there is an important role for the ring stereochemistry. Inhibitors 3e-g were prepared to assess the role played by both oxygen atoms of 3d on the binding mode of this latter compound. As shown in Table 1, a decrease in enzymatic inhibitory activity is observed when the cycloheptanol is introduced as the P2-ligand (3g). Moreover, but without being bound by theory, a nearly 30-fold reduction in enzymatic inhibitory potency of both 3e and 3f with respect to 3d demonstrated that both oxygen atoms may be important for the interaction with the enzyme at the S2-subsite. It is appreciated that both oxygen atoms engage in strong hydrogen bonding which, though without being bound by theory, it is believed contributes to the binding affinity for the enzyme. This result was further confirmed by the determination of the X-ray crystal structure of 3d-bound HIV-1 protease.

In another embodiment of the compounds described herein, reduction of the ring size of the P2-ligand resulted in inhibitor 3h, bearing a 6-membered 1,3-dioxan-5-yl urethane. This inhibitor showed an enzymatic $K_i$ value of 41 pM. Without being bound by theory, it is believed that the 1,3-dioxane ring can be accommodated by the S2-site. It is appreciated that both oxygens may be involved in specific interactions with the amino acid residues in this region.

In another embodiment, compounds 3l-m, presenting larger polyether rings are described. These compounds showed $K_i$ values in the high nM range ($K_i$s ranging from 6.3 to 33 nM), suggesting that large rings may not be easily accommodated at the S2-site.

Without being bound by theory, it is believed that subtle differences in the activity among these compounds suggest that not only the ring size, but also the position of the oxygen atoms within the polyether structure, could be important for inhibitory activity. In one embodiment compound 3k, presenting a 12-membered ring bearing a methylenedioxy unit instead of the ethylenedioxy of 3j, exhibited 5-fold potency enhancement compared to inhibitor 3j. It is also more than 2-fold more potent compared to 3i, which contains a smaller 10-membered ring. Substitution of a ring oxygen in 3i by a N-Me group provided inhibitor 3m with no change in inhibitory activity. However, replacement of ring oxygen with a $SO_2$ moiety provided inhibitor 3l with a 9-fold improvement in potency. Without being bound by theory, it is believed that the sulfone oxygens may be involved in specific interactions with the amino acid residues at the S2 site.

In MT-2 human T-lymphoid cells exposed to HIV-1-LAI, inhibitors 3d and 3h have shown antiviral $IC_{50}$ values of 4.9 nM and 3.4 nM, respectively (Table 1). Consistent with its enzymatic potency, compound 3b showed an antiviral activity of 30 nM in the same assay system, while compounds 3k-m did not exhibit appreciable antiviral properties at doses up to 1 µM. Two selected compounds, 3d, and 3h, were examined for their activity against HIV-1 using a human $CD_4$+ T-cell line (MT-2 cells) and human peripheral blood mononuclear cells (PBMCs) as target cells. Two endpoints for the activity against HIV-1 were employed: (i) the inhibition of the HIV-1-elicited cytopathic effect for MT-2 cells and (ii) the inhibition of HIV-1 p24 production for PBMCs. As examined in MT-2 cells as target cells, the two compounds, 3d and 3h exerted potent antiviral activity against an X4-HIV-lisolate (HIV-1-LAI) with $IC_{50}$ values of 4.9 and 3.4 nM, respectively (Table 1). Such anti-HIV-1 potency was generally parallel to the potency in enzymatic inhibition of the compounds. The two compounds were further examined in PBMCs against a clinical wild-type X4-HIV-1 isolate (HIV-1ERS104pre) along with various multi-drug-resistant clinical X4- and R5-HIV-1 isolates (Table 2). The activity of 3d and 3h against HIV-1(ERS104pre) was more potent or at least comparable as compared to those of currently available protease inhibitors, APV, IDV, and RTV. It is appreciated that the values of 3d were greater than those with MT-2 cells by factors of about 4. With regard to this difference, considering that 3d was potent when examined in human T cells (MT-2 cells) but its activity was slightly less in PBMCs, without being bound by theory, it is possible that relatively higher concentrations of 3d are required to suppress HIV-1 production in chronically infected macrophages. Two currently available protease inhibitors (IDV and RTV) were not capable of efficiently suppressing the replication of most of the multi-drug-resistant clinical isolates examined (HIV-1-MDR-B, HIV-1-MDR-G, HIV-1-MDR-TM, HIV-1-MDR-JSL, and HIV-1-MDR-MM) with $IC_{50}$ values of >1.0 µM. Although the two selected compounds were also less potent against the multi-drug-resistant clinical isolates examined, their $IC_{50}$ values were quite low with 0.22-0.54 µM (Table 2). During testing of the anti-HIV-1 activity of compounds 3b, 3d, 3h, and 3k-m, 4 concentrations were examined (1, 0.1, 0.01, and 0.001 µM) in the antiretroviral assay, conducted on three independent occasions (each assay was performed in duplicate). As noted, no cytotoxicity was observed for any of the compounds examined. Thus, it was deemed that the $IC_{50}$ values were greater than the highest concentration, 1 µM.

TABLE 2

Antiviral activity ($IC_{50}$) of inhibitors 3d and 3h against clinical HIV-1 isolates in PBMC cells (nM).

| Virus | $IC_{50}$ (nM) values[a] | | | | | |
|---|---|---|---|---|---|---|
| | 3d | 3h | DRV | RTV | APV | IDV |
| ERS104pre (wild-type) | 20 | 6 | 3.5 | 34 | 33 | 26 |
| MDR/TM | 220 (11) | 64 (10) | 4 (1) | >1000 (>29) | 290 (9) | >1000 (>38) |
| MDR/MM | 250 (13) | 110 (5) | 17 (5) | >1000 (>29) | 300 (9) | >1000 (>38) |
| MDR/JSL | 500 (25) | 330 (55) | 26 (7) | >1000 (>29) | 430 (13) | >1000 (>38) |
| MDR/B | 340 (17) | 230 (38) | 26 (7) | >1000 (>29) | 320 (10) | >1000 (>38) |
| MDR/C | 210 (11) | 160 (27) | 7 (2) | >1000 (>29) | 230 (7) | >1000 (>38) |
| MDR/G | 360 (18) | 300 (50) | 7 (2) | >1000 (>29) | 340 (10) | 290 (11) |
| MDR/A | 20 (1) | 13 (2) | 3 (1) | >1000 (>29) | 100 (3) | >1000 (>38) |

[a]Amino acid substitutions identified in the protease-encoding region compared to the consensus type B sequence cited from the Los Alamos database include L63P in HIV-1(ERS104pre); L10I, K14R, L33I, M36I, M46I, F53I, K55R, I62V, L63P, A71V, G73S, V82A, L90M, and I93L in HIV-1(MDR-B); L10I, V11I, T12E, I15V, L19I, R41K, M46L, L63P, A71T, V82A, and L90M in HIV-1(MDR-G); L10I, K14R, R41K, M46L, I54V, L63P, A71V, V82A, L90M, I93L in HIV-1(MDR-TM); L10I, L24I, I33F, E35D, M36I, N37S, M46L, I54V, R57K, I62V, L63P, A71V, G73S, and V82A in HIV-1(MDR-JSL); and L10I, K43T, M46L, I54V, L63P, A71V, V82A, L90M, and Q92K in HIV-1(MDR-MM). HIV-1(ERS104) preserved as a source of wild-type HIV-1. The $IC_{50}$ values were determined by employing PHA-PBMC (phytohemaglutinin-activated peripheral blood mononuclear cells) as target cells and the inhibition of p24Gag protein production as the endpoint. All values were determined in triplicate. DRV (Darunavir), SQV (Saquinavir), APV (Amprenavir), IDV (Indinavir).

The mode of binding of the inhibitor was evaluated by analyzing the atomic resolution crystal structure of HIV-1 protease with 3d. The crystal structure was solved and refined to an R factor of 14.9% at 1.00 Å resolution. It was observed herein that the inhibitor binds with extensive interactions from P2 to P2' to the protease atoms, and notably, the favorable polar interactions include hydrogen bonds, weaker C—H . . . O and C—H . . . pi interactions. The central hydroxyl group forms hydrogen bonds to the side chain carboxylate oxygen atoms of the catalytic Asp25 and Asp25' residues. The inhibitor hydrogen bonds with protease main chain atoms of the amide of Asp29, the carbonyl oxygen of Gly27, and the water-mediated interactions with the amides of Ile50 and Ile50' which are conserved in the majority of protease complexes with inhibitors and substrate analogs. Inhibitor 3d has retained the water-mediated interaction with the pi system of the P2' aromatic ring which was observed for darunavir (1) and GRL-98065. The P2' methoxy group forms a hydrogen bond with the amide of Asp30'. It is appreciated that the P2 group forms a water-mediated interaction with the amide of Gly48, similar to the interactions described for several peptide substrate analogs (Tie, Y.; 2005).

Herein are described a series potent HIV-1 protease inhibitors. The inhibitors incorporate a variety of flexible cyclic ethers/polyethers as the P2-ligand. Inhibitors containing small size 1,3-dioxacycloakanes have shown potent inhibitory properties. Inhibitors 3d and 3h, one embodiment of the compounds described herein, have shown enzyme inhibitory and antiviral potency. Inhibitors incorporating medium-size cyclic polyethers or polyethers containing a sulfone or amine functionality were less potent in antiviral assays. In one illustrative example, the preparation of inhibitor 3d, was carried out incorporating an optically active synthesis of (R)-1,3-dioxepan-5-ol, using (S)-malic acid as the starting material. Herein are described syntheses of various cyclic ethers and cylic polyethers. Inhibitor 3d has shown activity against multi-PI-resistant variants compared to other FDA approved inhibitors. Described herein is a protein-ligand X-ray structure of 3d-bound HIV-1 protease determined at 1.0 Å resolution. It is appreciated that one of the oxygens of the 1,3-dioxepane ligand is involved in hydrogen bonding with Asp29 and Asp30 NH's. It is further appreciated that the other oxygen is involved in a unique interaction with Gly-48 NH through a water molecule. Without being bound by theory, it is believed that design of inhibitors using the concept of maximizing 'backbone binding' yields PIs characterized by high potency against both wild-type and multi-drug-resistant HIV-1 strains.

Without being bound by theory, it is believed that one method to combat drug resistance is to maximize ligand-binding site interactions in the active site and particularly to promote extensive hydrogen bonding with the active site protein backbone. Indeed, inhibitor 101 incorporates a stereochemically defined bicyclic cyclopentanyltetrahydrofuran (Cp-THF) as the P2-ligand in the hydroxylethylsulfonamide isostere. It is appreciated herein that the cyclic ether oxygen may be involved in hydrogen bonding with the backbone NH of Asp-29. Without being bound by theory, it is believed that the presence of this oxygen in the compounds described herein is important for antiviral properties against drug resistant HIV strains. Without being bound by theory, it has been discovered herein that a simplified meso-hexahydrocyclopenta-1,3-dioxolane ligand may maintain similar interactions with respect to the Cp-THF ligand in inhibitor 101. It is appreciated that one of the oxygens of this meso ligand can hydrogen bond with Asp-29 NH. Since the Cp-THF ligand in inhibitor 1 contains three chiral centers, incorporation of a meso ligand as shown in inhibitor 102 would simplify the synthesis compared to the bicyclic Cp-THF ligand. Furthermore, it is appreciated that the second oxygen atom in the meso-P2-ligand could engage in further interactions at the S2-sub site. Herein are described a series of protease inhibitors that incorporate structure-based designed symmetric meso-bicyclic 1,3-dioxolane and 1,3-dioxane derivatives as the P2-ligands. Inhibitors (102 and 103) incorporating these ligands have shown potent enzyme inhibitory potency as well as antiviral activity. The drug resistance profile of inhibitor 102 against multi-drug-resistant clinical isolates is described herein. The protein-ligand X-ray structure of one illustrative embodiment of the compounds described herein, 103, bound to HIV-1 protease has been determined.

In one embodiment, the cyclic ethers shown below are described.

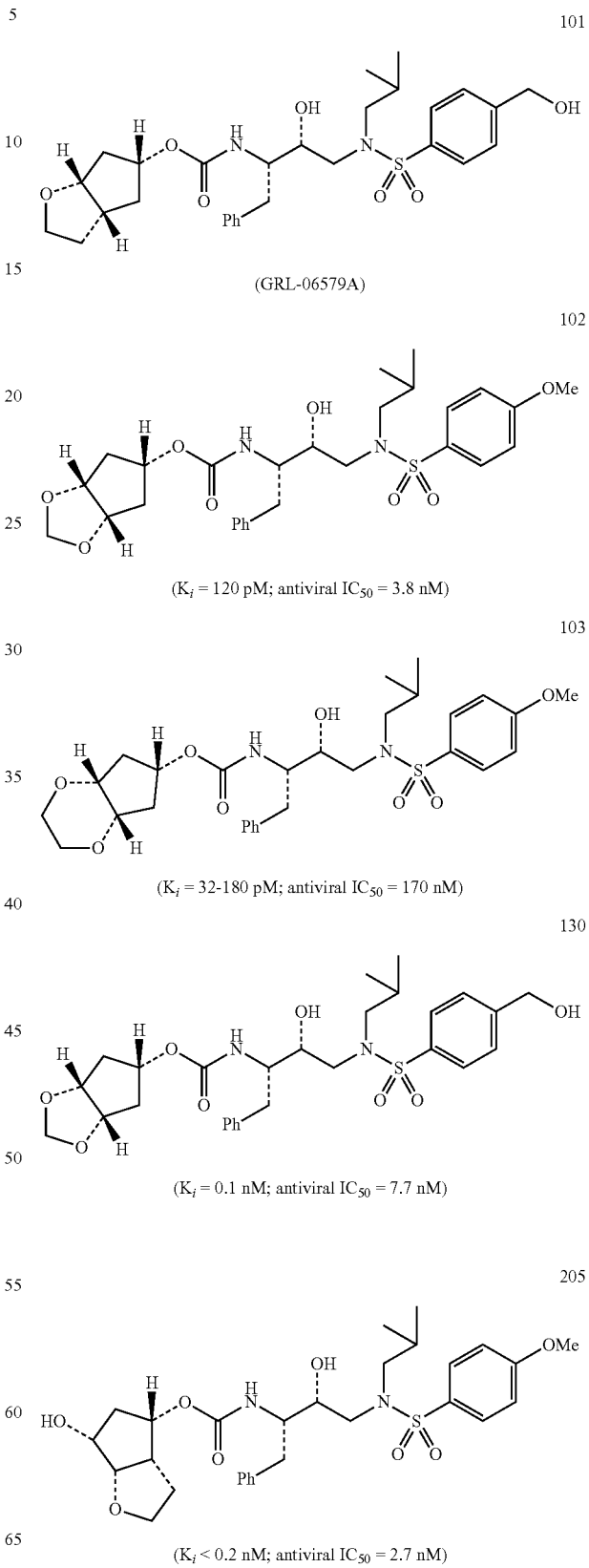

101

(GRL-06579A)

102

($K_i$ = 120 pM; antiviral $IC_{50}$ = 3.8 nM)

103

($K_i$ = 32-180 pM; antiviral $IC_{50}$ = 170 nM)

130

($K_i$ = 0.1 nM; antiviral $IC_{50}$ = 7.7 nM)

205

($K_i$ < 0.2 nM; antiviral $IC_{50}$ = 2.7 nM)

27
-continued

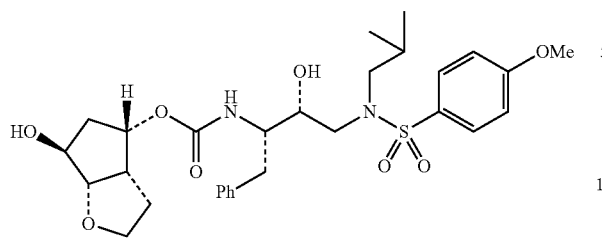

206

($K_i < 0.2$ nM; antiviral $IC_{50} = 4$ nM)

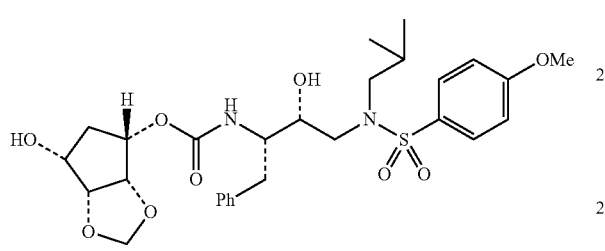

207

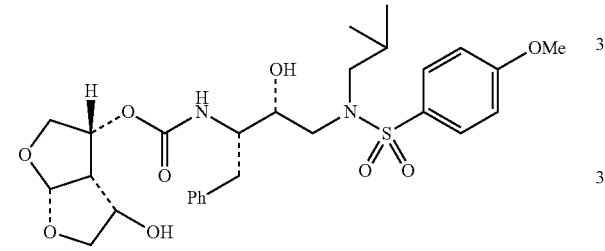

208

($K_i < 0.2$ nM; antiviral $IC_{50} = 8.6$ nM)

28
-continued

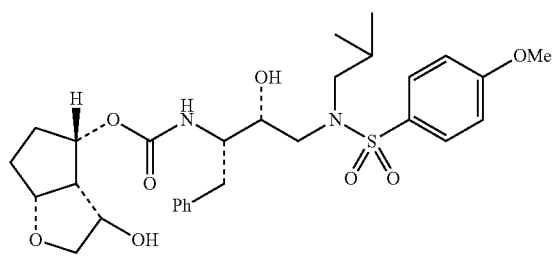

209

The inhibitory potencies of synthetic inhibitors may be evaluated using the assay protocol of Toth and Marshall (Toth, M. V.; Marshall, G. R.; Int. J. Pept. Protein Res., 1990, 36, 544) and the results are shown in Table 3. Inhibitor 102 has shown an enzyme inhibitory potency of 0.12 nM. Without being bound by theory, it appears that the bicyclic 1,3-dioxolan ring can be accommodated by the S2-subsite of HIV-1 protease. Inhibitor 126 with a meso ligand containing a trans bicyclic-1,3-dioxolan ring is 3.5-fold less potent than the syn isomer 102. In another embodiment the effect of both syn and anti 10 trioxepane ring as P2-ligands in inhibitors 127 and 128 was examined. The syn-isomer 128 is more potent (Ki=0.5 nM) over the anti-isomer 127. Without being bound by theory, is believed that the 1,4-dioxane ring may not only fill in the hydrophobic S2-site, but also that the oxygens on the dioxane ring may interact with backbone atoms or residues in the active site. In one embodiment the meso ligand in inhibitor 103, with a syn-bicyclic-1,4-dioxane ring, has shown high enzyme inhibitory potency with a Ki value of 32 pM. In another embodiment the corresponding anti-isomer 128 is less potent which, without being bound by theory, is consistent with previous results. In another embodiment, the P2-ligand Cp-THF ligand with a P2'-hydroxymethyl sulfonamide (inhibitor 1) is more potent than the corresponding P2'-methoxybenzene sulfonamide derivative. In another embodiment, the inhibitory potency of inhibitor 130, with a P2'-hydroxymethyl benzene sulfonamide derivative, was compared with inhibitor 102. However, inhibitor 130 did not exhibit any potency enhancing effect.

TABLE 3

| Entry | Inhibitor | $K_i$ (nM)[a] | $IC_{50}$ (μM)[b] |
|---|---|---|---|
| 1 | 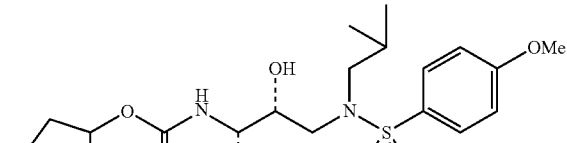 102 | 0.11 – 0.12 | 0.0038 ± 0.0001 |
| 2 | 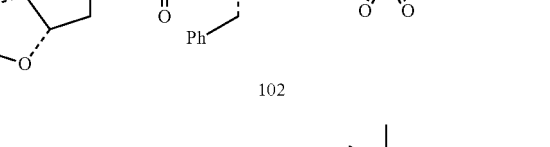 126 | 0.40 ± 0.04 | nd |

TABLE 3-continued

| Entry | Inhibitor | $K_i$ (nM)[a] | $IC_{50}$ (μM)[b] |
|---|---|---|---|
| 3 | 127 | 5.4 ± 0.22 | >1 |
| 4 | 128 | 0.51 ± 0.01 | 0.38 ± 0.02 |
| 5 | 103 | 0.18 ± 0.03; 0.032 | 0.17; 0.21 ± 0.04 |
| 6 | 129 | 0.50 ± 0.04 | nd |
| 7 | 130 | 0.34 ± 0.07 | 0.0077 ± 0.003 |

[a]Values are means of at least two experiments.
[b]MT-2 human T-lymphoid cells exposed to HIV-1$_{LAI}$; Antiviral activity of amprenavir (APV), saquinavir (SQV) and indinavir (IDV) were 0.03 μM, 0.02 μM and 0.03 μM respectively in this assay.
nd: not determined.

In another embodiment compounds are described that show activity against HIV-1 using a human CD4+ T-cell line (MT-2 cells). Illustratively, selected compounds are examined for their activity against HIV-1 using a human CD4+ T-cell line (MT-2 cells). For example, the activity of inhibitor 102 against a variety of multi-drug resistant HIV-1 variants was also examined in detail using human peripheral blood mononuclear cells (PBMCs) as target cells. Two endpoints for the activity against HIV-1 were employed: (i) the inhibition of the HIV-1-elicited cytopathic effect for MT-2 cells and (ii) the inhibition of HIV-1 p24 production for PBMCs.

When examined in MT-2 cells as target cells, inhibitor 103, characterized by a potent enzymatic inhibitory activity, showed an antiviral $IC_{50}$ value in the high nanomolar range ($IC_{50}$=170 nM, Table 3), while inhibitor 102, although it had a lower enzymatic inhibitory potency compared to 103, displayed potent antiviral activity ($IC_{50}$=3.8 nM) against an X4-HIV-1 isolate (HIV-1LAI) (Table 3). Inhibitor 102 was examined for its activity against a clinical wildtype X4-HIV-1 isolate (HIV-1ERS104pre) along with various multi-drug-resistant clinical X4- and R5-HIV-1 isolates (Table 4) using PBMCs as target cells. The activity of inhibitor 102 against HIV-1ERS104pre ($IC_{50}$ of 29 nM) was comparable to those of currently available protease inhibitors, SQV, APV, and IDV with which display $IC_{50}$ values of 12, 33, and 26 nM, respectively. The $IC_{50}$ value of inhibitor 102 in PBMCs cells ($IC_{50}$=29 nM) was nearly 8-fold greater than the $IC_{50}$ value in MT-2 cells ($IC_{50}$=3.8 nM). With regard to this difference, considering that 102 is highly potent as examined in human T cells (MT-2 cells) but its activity is slightly less in PBMCs, though without being bound by theory, it is possible that relatively higher concentrations of 102 are required to suppress HIV-1 production in chronically infected macrophages. IDV was not capable of efficiently suppressing the replication of most of the multi-drug-resistant clinical isolates examined (HIV-1MDR/MM, HIV-1MDR/JSL, HIV-1MDR/C, and HIV-1MDR/A) with $IC_{50}$ values of >1.0 μM. The potency of inhibitor 2 against most of the multi-drug resistant variants was generally comparable to that of SQV and APV, although DRV was found the most potent among those tested including inhibitor 2 against HIV-1ERS104pre as well as all the multi-drug-resistant variants.

TABLE 4

Antiviral activity of inhibitor 2 against clinical HIV-1 isolates in PBMC cells, $IC_{50}$ (nM).

| virus | $ICB_{50}$ values[a] (nM) | | | | |
|---|---|---|---|---|---|
|  | 2 | DRV[b] | SQV[c] | APV[d] | IDV[e] |
| HIV-1B$_{ERS104pre}$ (wild-type: X4) | 29 | 3.5 | 12 | 33 | 26 |
| HIV-1B$_{MDR/MM}$ (R5) | 150 (5) | 1 (5) | 190 (16) | 300 (9) | >1000 (>38) |
| HIV-1B$_{MDR/JSL}$ (R5) | 550 (19) | 26 (7) | 330 (28) | 430 (13) | >1000 (>38) |
| HIV-1B$_{MDR/C}$ (X4) | 300 (10) | 7 (2) | 36 (3) | 230 (7) | >1000 (>38) |
| HIV-1B$_{MDR/G}$ (X4) | 340 (12) | 7 (2) | 29 (2) | 340 (10) | 290 (11) |
| HIV-1B$_{MDR/A}$ (X4) | 21 (1) | 3 (1) | 81 (7) | 100 (3) | >1000 (>38) |

[a] Amino acid substitutions identified in the protease-encoding region compared to the consensus type B sequence cited from the Los Alamos database include L63P in HIV-1ERS104pre; L10I, K14R, L33I, M36I, M46I, F53I, K55R, I62V, L63P, A71V, G73S, V82A, L90M, and I93L in HIV-1MDR-B; L10I, V11I, T12E, I15V, L19I, R41K, M46L, L63P, A71T, V82A, and L90M in HIV-1MDR-G; L10I, K14R, R41K, M46L, I54V, L63P, A71V, V82A, L90M, I93L in HIV-1MDR-TM; L10I, L24I, I33F,E35D, M36I, N37S, M46L, I54V, R57K, I62V, L63P, A71V, G73S, and V82A in HIV-1MDR-JSL; and L10I, K43T, M46L, I54V, L63P, A71V, V82A, L90M, and Q92K in HIV-1MDR-MM. HIV-1ERS104pre served as a source of wild-type HIV-1. The $IC_{50}$ values were determined by employing PHA-PBMC (phytohemaglutinin-activated peripheral blood mononuclear cells) as target cells and the inhibition of p24Gag protein production as the endpoint. All values were determined in triplicate.
[b] DRV (Darunavir),
[c] SQV (Saquinavir),
[d] APV (Amprenavir),
IDV (Indinavir).
X4 denotes CXCR4-tropic HIV-1 while R5 CCR5-tropic HIV-1.

X-Ray Crystallography

To obtain molecular insights into the ligand-binding site interactions responsible for impressive enzyme inhibitory potency of compound 103, the X-ray structure of 103-bound HIV-1 protease is described. The crystal structure was solved and refined to an R factor of 15.2% at 1.07 Å resolution. The inhibitor binds with extensive interactions from P2 to P2' with protease atoms, and most notably the favorable polar interactions including hydrogen bonds. The transition-state hydroxyl group forms hydrogen bonds to the side chain carboxylate oxygen atoms of the catalytic Asp25 and Asp25'. It is appreciated that the meso-bicyclic 1,4-dioxane ligand may be involved in hydrogen bonding interactions with the backbone atoms and residues at the S2-site. One of the dioxane oxygens forms hydrogen bonds with the backbone NH of Asp29. The other oxygen makes a water mediated hydrogen bond with the carbonyl oxygen of Gly48. These interactions have been described for several peptide substrate analogs). However, design of high affinity ligands incorporating this interaction with Gly48 has not been previously demonstrated. The inhibitor also hydrogen bonds with protease main chain amide carbonyl oxygen of Gly27, and the water-mediated interactions with the amides of Ile50 and Ile50' that are conserved in the majority of protease complexes with inhibitors and substrate analogs. It has been previously found that the weaker polar interactions such as C—H . . . O and water-pi interactions can be analyzed in atomic resolution structures. Inhibitor 103 also shows a water-mediated interaction of the pi system of the P2' aromatic ring with the amide of Asp29, which was also observed for darunavir and inhibitor 1. Furthermore, the P2' methoxy group forms a hydrogen bond to the backbone NH of Asp30'. Importantly, the P2 group forms a hydrogen bond interaction with the carbonyl oxygen of Gly48 and a water-mediated interaction with the amide of Gly48, similar to the interactions described for several peptide substrate analogs. Without being bound by theory, it is believed that these interactions of the P2 group confirm the design strategy of incorporating new polar interactions with conserved backbone regions of the protease. To study the binding interactions of the corresponding meso-1,3-dioxolane ligand in the S2-subsite, an active model of inhibitor 102 based upon the X-ray structure of 103-bound HIV-1 protease has been created. Without being bound by theory, it is believed that the model shows that both dioxolane oxygens may interact with active site residues Asp-29 and Asp-30 as well as Gly-48 through the structural water molecule similarly to the 1,4-dioxane ligand of inhibitor 103.

In another embodiment, described herein is a series of HW-1 protease inhibitors, designed and synthesized by incorporating bicyclic meso-1,3-dioxolane and 1,4-dioxane derivative as the P2-ligands. The inhibitors have been observed herein to possess high enzyme inhibitory and antiviral potency, similar to inhibitor 101 with stereochemically defined Cp-THF ligand. The design of meso-1,3-dioxolane and 1,4-dioxane P2-ligands as exemplified in inhibitors 102 and 103, respectively. It is appreciated that such embodiments have less stereochemical complexity as well as a simpler chemical synthesis over the Cp-THF ligand in inhibitor 101. In another embodiment, efficient synthetic routes to these ligands are described. Inhibitor 102 shows potent antiviral activity in both MT-2 and PBMCS cell lines. Inhibitor 102 was profiled against a series of multi-drug-resistant clinical isolates. While inhibitor 102 is less potent than darunavir, it is more potent than IND and comparable to APV and SQV in suppressing the replication of multi-drug-resistant isolates, MDRMM and MDRJSL. Without being bound by theory, it is believed that a protein-ligand X-ray structure of compound 103-bound to HIV-1 protease revealed extensive interaction of the inhibitor in the active site of HIV-1 protease. It is appreciated that both oxygens of the meso-P2-ligand may be involved in hydrogen bonding interactions with the protein backbone atoms. In particular, a water-mediated hydrogen bond to Gly48 carbonyl is very unique.

In another embodiment, processes for preparing the inhibitors are described herein. Illustratively, the inhibitors are prepared as shown in the following scheme.

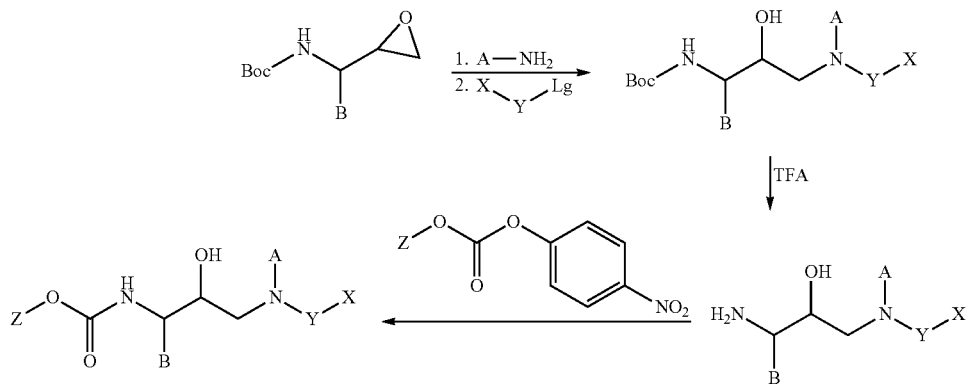

In another embodiment, pharmaceutical dosage forms of and methods of administration of the compounds are described herein. The compounds described herein can be prepared and administered in a wide variety of oral, parenteral and topical dosage forms, utilizing art-recognized products. See generally, Remington: The Science and Practice of Pharmacy, ($21^{st}$ ed., 2005). Thus, the compounds described herein can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds described herein can be administered transdermally. It is also envisioned that multiple routes of administration (e.g., intramuscular, oral, transdermal) can be used to administer the compounds described herein. Accordingly, pharmaceutical compositions comprising a pharmaceutically acceptable carrier or excipient and one or more compounds described herein are described.

Liquid dosage forms for oral administration may include pharmaceutically acceptable emulsions, microemulsions, solutions, suspensions, and syrups containing inert diluents commonly used in the art, such as water. Such compositions may also comprise adjuvants such as wetting agents, emulsifying and suspending agents, sweetening, and flavoring agents. Injectable preparations of the compounds described herein can be formulated utilizing art-recognized products by dispersing or dissolving an effective dose of the compound in a parenterally acceptable diluent such as water, or more preferably isotonic sodium chloride solution. The parenteral formulations can be sterilized using art-recognized microfiltration techniques.

The compounds describe herein can also be formulated as solid dosage forms for oral administration such as capsules, tablets, powders, pills and the like. Typically the active compound is admixed with an inert diluent or carrier such as sugar or starch and other excipients appropriate for the dosage form. Thus, tableting formulations will include acceptable lubricants, binders and/or disintegrants. Optionally powder compositions comprising an active compound described herein and, for example, a starch or sugar carrier can be filled into gelatin capsules for oral administration. Other dosage forms of the compounds described herein can be formulated using art-recognized techniques in forms adapted for the specific mode of administration.

In another embodiment, processes for preparing the compounds are described herein. Illustratively, the syntheses of seven and eight membered 1,3-dioxacycloalkanes 8a-d for the corresponding inhibitors 3a-d, are shown in Scheme 1.

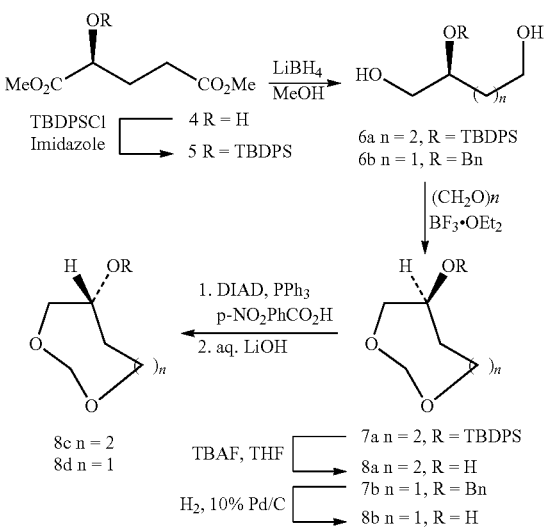

Protected diol 6a is prepared by a two step procedure starting from (S)-hydroxyglutaric acid 4, which may be obtained by following a published protocol (Winitz, M.; et al., Studies on Diastereoisomeric α-Amino Acids and Corresponding α-Hydroxy Acids. VII. Influence of β-Configuration on Enzymic Susceptibility. *J. Am. Chem. Soc.* 1956, 78, 2423-2430). The hydroxyl group of 4 is protected as a tert-butyldiphenylsilylether 5 in quantitative yield. $LiBH_4$ reduction of both ester groups provides 6a in good yield. Additional details of the synthesis are described in Soai, K.; Ookawa, A. Mixed solvents containing methanol as useful reaction media for unique chemoselective reductions with lithium borohydride. *J. Org. Chem.* 1986, 51, 4000-4005).

Compounds 6a and 6b (Gmeiner, P.; Junge, D. Regioselective transformation of malic acid: a practical method for the construction of enantiomerically pure indolizidines. *J. Org. Chem.* 1995, 60, 3910-3915.) are converted to cyclic derivatives by exposure to paraformaldehyde and BF$_3$.OEt$_2$ to afford cyclic ethers 7a and 7b in 51% and 82% yield, respectively (Le Merrer, Y.; et al. Synthesis of C$_2$-symmetric guanidino-sugars as potent inhibitors of glycosidases. *Bioorg. Med. Chem.* 2000, 8, 307-320). Deprotection of compounds 7a to 8a was carried out by using n-Bu$_4$N$^+$F$^-$ in THF. Benzylether of 7b was removed by a catalytic hydrogenation over 10% Pd—C to furnish 8b. Mitsunobu inversion of the secondary hydroxyl groups of 8a,b was accomplished by using p-nitrobenzoic acid, triphenylphosphine and diisopropylazodicarboxylate in benzene at 23° C. Saponification of the resulting esters provided 8c and 8d.

For the synthesis of compounds 8e and 8f, which represent the monoxygenated analogues of 8d, a synthetic strategy based on a ring-closing metathesis reaction as the key step is described (Schemes 2 and 3). Accordingly, secondary alcohol 9 (Pospíšil, J.; Markó, I. E. Total synthesis of (R)-(+)-goniothalamin and (R)-(+)-goniothalamin oxide: first application of the sulfoxide-modified Julia olefination in total synthesis. *Tetrahedron Lett.* 2007, 47, 5933-5937) (Scheme 2) was protected as the corresponding methoxyethoxymethyl (MEM)-ether 10 in 90% yield using an excess of MEM-Cl in the presence of DIPEA in CH$_2$Cl$_2$ Scheme 2. Synthesis of cyclic ether 8e

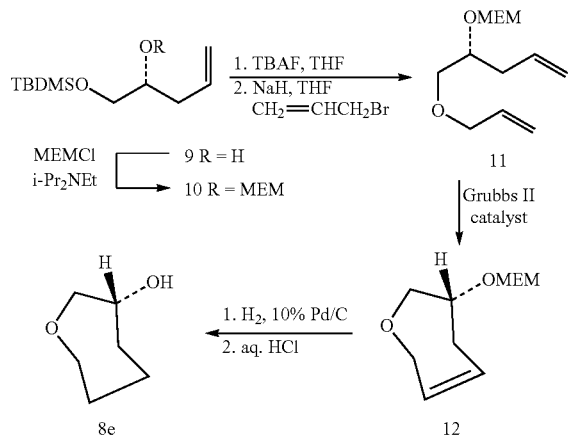

Subsequent n-Bu$_4$N$^+$F$^-$-promoted deprotection of the TBDMS-group afforded the corresponding primary alcohol which was treated with sodium hydride and alkylated with allyl bromide in the presence of a catalytic amount of n-Bu$_4$N$^+$I$^-$ to afford olefin 11 in 78% yield (2 steps). A 0.01 M solution of 11 in CH$_2$Cl$_2$ was then treated with a catalytic amount (5 mol %) of 2nd generation Grubbs catalyst and heated to 45° C. to afford the cyclooxepane 12 in 94% yield. The double bond of 12 was reduced by catalytic hydrogenation using 10% Pd—C as the catalyst and the MEM-ether was removed by acidic hydrolysis in a 1:1 THF/H$_2$O mixture to obtain the target alcohol 8e in good overall yield.

For the synthesis of alcohol 8f (Scheme 3), compound 13 was used as the starting material. It was in turn prepared following a described procedure starting from acrolein and tert-butylacetate (Lu, C.-D.; Zakarian, A. Studies toward the synthesis of pinnatoxins: The B,C,D-dispiroketal fragment. *Org. Lett.* 2007, 9, 3161-3163).

Scheme 3. Synthesis of cyclic ether 8f

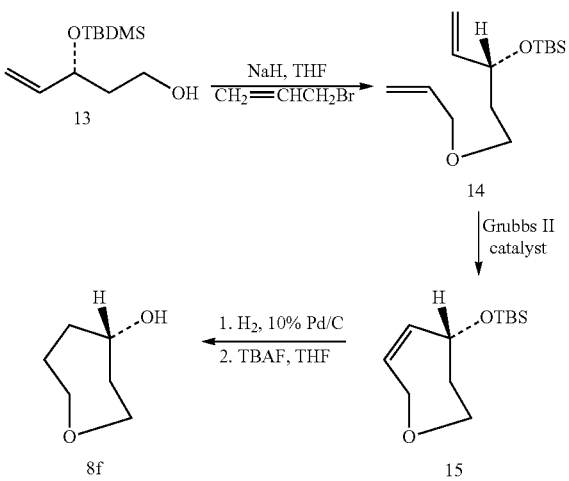

Alkylation of the primary hydroxyl group of 13 with allyl bromide and n-Bu$_4$N$^+$I$^-$ using sodium hydride as the base furnished the ring closing metathesis precursor 14. The cyclization reaction was performed by using 2nd generation Grubbs catalyst (5 mol %) in CH$_2$Cl$_2$ and afforded olefin 15 in good yield. Subsequent hydrogenation of the double bond and n-Bu$_4$N$^+$F$^-$-mediated removal of TBDMS-ether afforded the target alcohol 8f.

Alcohols 8h-j used in the preparation of inhibitors 3h-j were synthesized starting from the common intermediate 2-benzyloxypropane-1,3-diol 17 as shown in Scheme 4.

Scheme 4. Synthesis of polyethers 8h-j

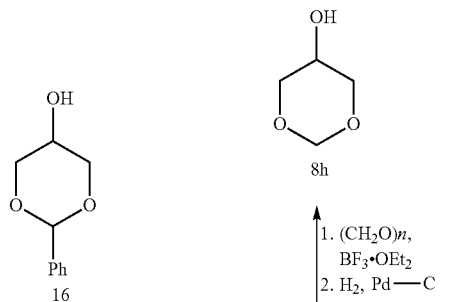

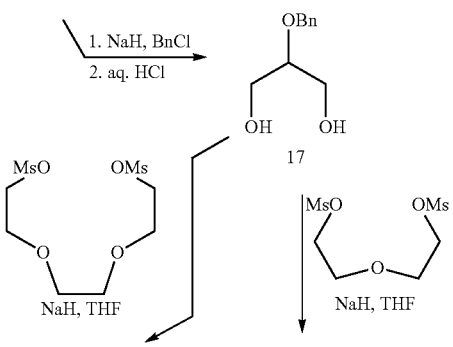

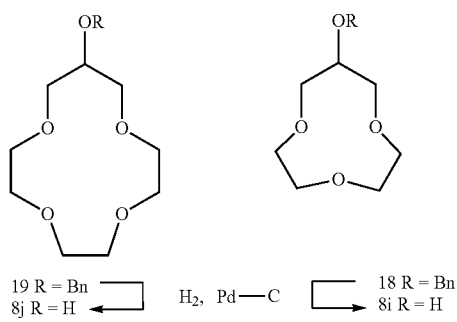

19 R = Bn
8j R = H
H₂, Pd—C
18 R = Bn
8i R = H

Compound 17 was prepared by alkylation of commercially available benzylidene acetal 16 with benzyl chloride in the presence of sodium hydride and a catalytic amount of n-Bu₄N⁺I⁻ in THF at 23° C. The benzylidene group was subsequently removed by hydrolysis with 6 N HCl in a mixture (1:1) of THF and water to give 2-benzyloxy-1,3-propanediol 17 in quantitative yield. Treatment of 17 with paraformaldehyde and BF₃.OEt₂ as described above, followed by hydrogenolysis of the resulting O-benzylether afforded 8h in 78% overall yield.

Treatment of diol 17 with an excess of sodium hydride in refluxing THF followed by addition of di(ethyleneglycol)dimesylate or tri(ethyleneglycol)dimesylate afforded macrocycles 18 and 19 in 19% and 29% yield, respectively. Dilution of the reaction mixture to assist the intramolecular cyclization reaction did not result in a significant improvement of the reaction yields. No attempts were made to improve the cyclization yield for the preparation of these 10- and 13-membered polyether rings. Compounds 18 and 19 were subsequently deprotected by hydrogenolysis to obtain alcohols 8i and 8j.

In another embodiment, the synthesis of compounds 8k, 8l and 24 from known diols 20 is described, and shown in Scheme 5 (Kasireddy, K.; et al., Synthesis of novel cationic cardiolipin analogues for the optimal delivery of therapeutic agents. *Tetrahedron Lett.* 2004, 45, 2743-2746).

Scheme 5. Synthesis of alcohols 8k, l and 24

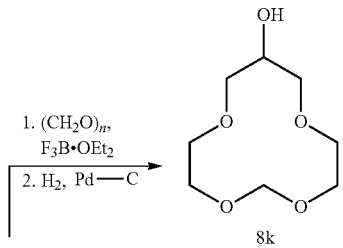

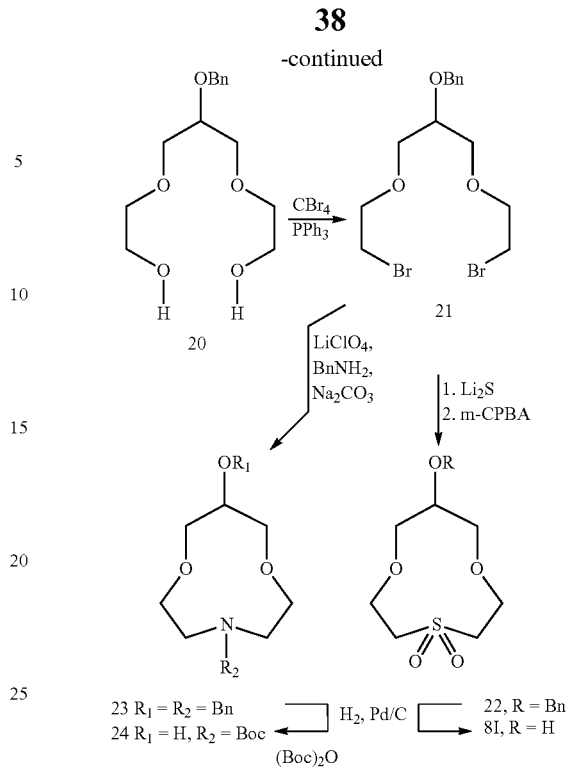

Exposure of 20 to paraformaldehyde in the presence of BF₃.OEt₂ furnished the corresponding cyclic polyether product, which, upon hydrogenolysis, gave alcohol 8k. Bromination of 20 using carbon tetrabromide and triphenylphosphine afforded dibromide 21. This dibromide was used for the synthesis of sulfone 8l and protected amine 24. Thus, compound 21 was reacted with one equivalent of benzylamine in refluxing MeCN in the presence of sodium carbonate, as reported by Calverley and Dale to provide 23 in 24% yield (Calverley, M. J.; Dale, J. 1,4,7-Trioxa-10-azacyclododecane and some N-substituted derivatives; synthesis and cation complexing. *Acta Chem. Scand.* 1982, B36, 241-247). Dimerization is the main side product in this reaction and one can reduce such dimerization by using an excess of LiClO₄ (Sakamoto, H.; et al., Lipophilic bis(monoaza crown ether) derivatives: synthesis and cation-complexing properties. *J. Org. Chem.* 1986, 51, 4974-4979). Benzylamine 23 was hydrogenated over 10% Pd—C in the presence of di-t-butyl dicarbonate to provide N-Boc protected alcohol 24. Sulfone 22 was obtained by cyclization of 21 with lithium sulfide followed by oxidation of the corresponding sulfide with an excess of m-CPBA in CH₂Cl₂ at 23° C. Benzyl derivative 22 was converted to 8l by a catalytic hydrogenation over 10% Pd—C.

In another embodiment, processes for preparing active carbonate intermediates are described herein. Illustratively, Scheme 6 depicts the conversion of various P2-ligands to the corresponding active carbonates for urethane formation.

Scheme 6. Synthesis of various active carbonates

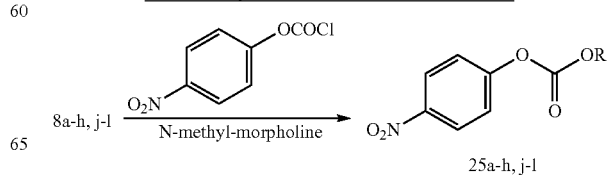

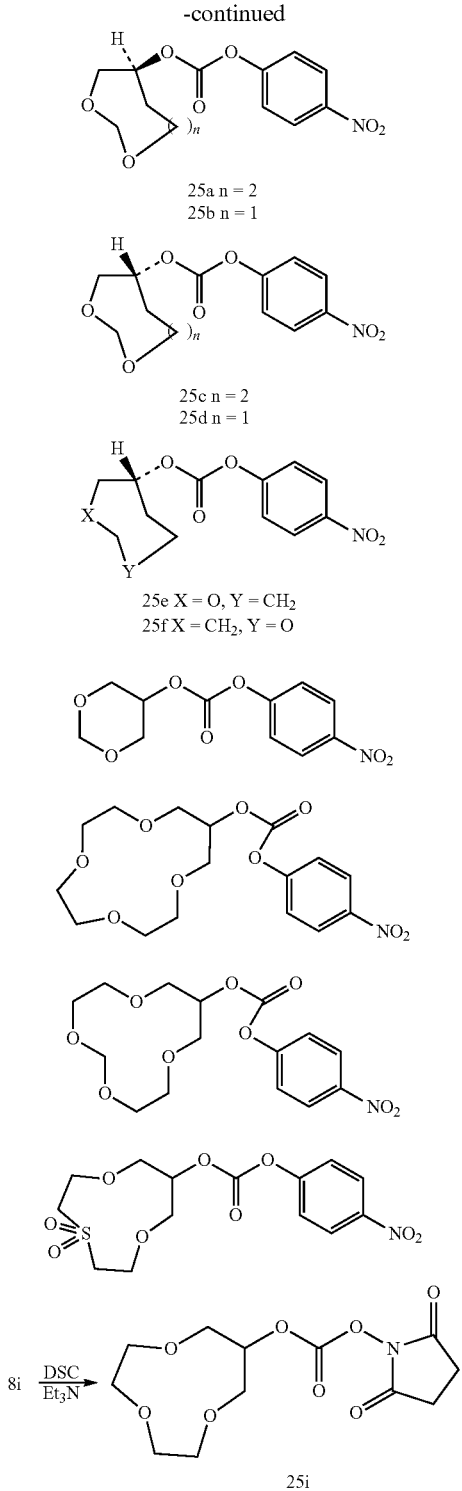

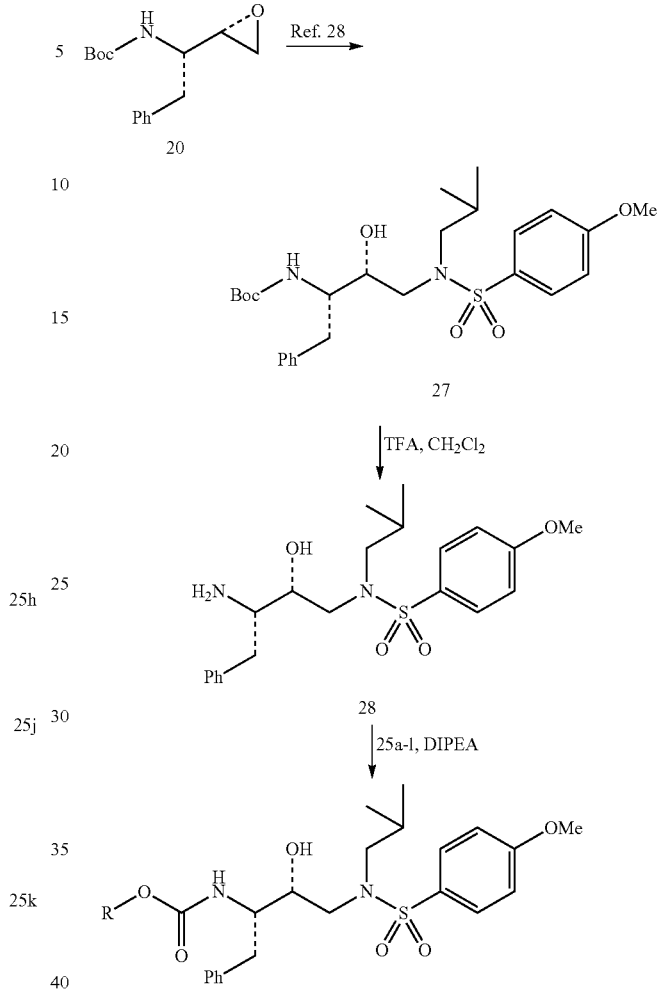

Accordingly, alcohols 8a-h,j-l were reacted with p-nitrophenylchloroformate and N-methylmorpholine in THF at 23° C. to provide corresponding carbonates 25a-h,j-l in 67-89% yields. Alcohol 8l was converted to succinimidylcarbamate 25i by treatment with N,N'-succinimidylcarbonate in the presence of Et₃N in MeCN in 37% isolated yield.

In another embodiment, the synthesis of inhibitors 3a-l is described, and shown in Scheme 7.

Methoxysulfonamide derivative 27 was prepared from commercially available epoxide 26 as described previously (Ghosh, A. K.; Fidanze, S. Transition-state mimetics for HIV protease inhibitors: stereo-controlled synthesis of hydroxyethylene and hydroxyethylamine isosteres by ester-derived titanium enolate syn and anti-aldol reactions. *J. Org. Chem.* 1998, 63, 6146-6152). The Boc group in 27 was removed by exposure to a 30% solution of TFA in $CH_2Cl_2$ at 23° C. The resulting amine 28 was reacted with the suitable mixed activated carbonates 25a-l in THF at 23° C. for 2 to 4 days to furnish inhibitors 3a-l in 36-89% yield.

In another embodiment, the synthesis of inhibitor 3m is described, and shown in Scheme 8.

Scheme 8. Synthesis of inhibitor 3m

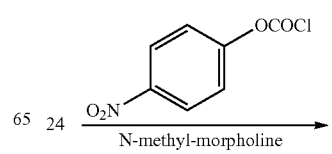

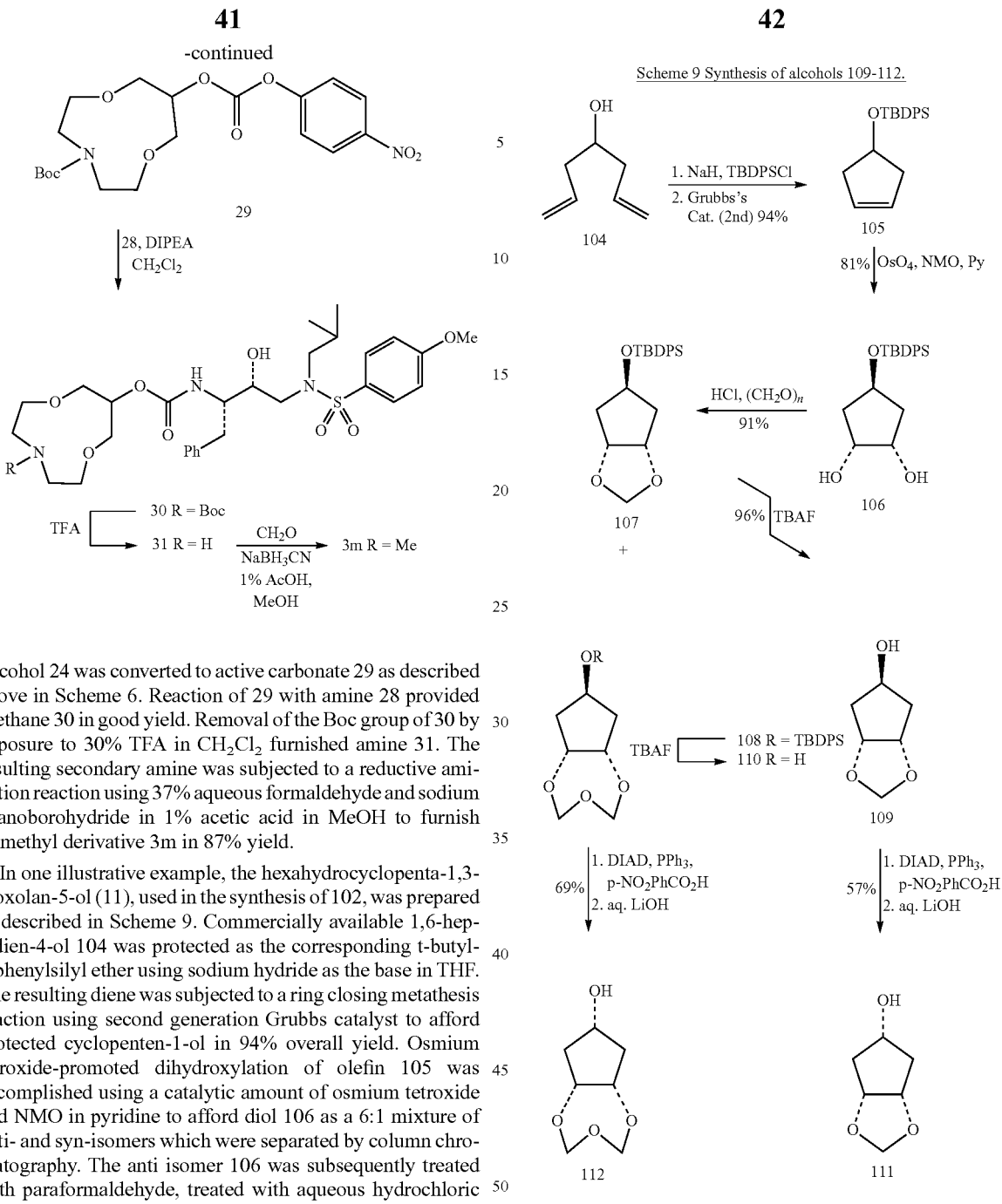

Alcohol 24 was converted to active carbonate 29 as described above in Scheme 6. Reaction of 29 with amine 28 provided urethane 30 in good yield. Removal of the Boc group of 30 by exposure to 30% TFA in CH$_2$Cl$_2$ furnished amine 31. The resulting secondary amine was subjected to a reductive amination reaction using 37% aqueous formaldehyde and sodium cyanoborohydride in 1% acetic acid in MeOH to furnish N-methyl derivative 3m in 87% yield.

In one illustrative example, the hexahydrocyclopenta-1,3-dioxolan-5-ol (11), used in the synthesis of 102, was prepared as described in Scheme 9. Commercially available 1,6-heptadien-4-ol 104 was protected as the corresponding t-butyldiphenylsilyl ether using sodium hydride as the base in THF. The resulting diene was subjected to a ring closing metathesis reaction using second generation Grubbs catalyst to afford protected cyclopenten-1-ol in 94% overall yield. Osmium tetroxide-promoted dihydroxylation of olefin 105 was accomplished using a catalytic amount of osmium tetroxide and NMO in pyridine to afford diol 106 as a 6:1 mixture of anti- and syn-isomers which were separated by column chromatography. The anti isomer 106 was subsequently treated with paraformaldehyde, treated with aqueous hydrochloric acid in chloroform under reflux (Ashkenazi, P; et al., Tetrahedron, 1978, 2161), affording the cyclic acetal 107 in good yield. Along with the desired compound 107, the trioxepane 108 was also isolated from the reaction mixture in a 1:1 ratio. In another embodiment of the compounds described herein, the tetrahydro-5aH-cyclopenta[f][1,3,5]trioxepan-7-yl-moiety of 108 was incorporated as the P2-ligand (resulting in inhibitors 27-28, Table 3) because, without being bound by theory, it is believed that the higher flexibility of the trioxepane ring allows an improved adaptability to enzyme amino acid mutations, resulting in better activity against resistant HIV strains. Accordingly, both intermediates 107 and 108 were deprotected using tetrabutylammonium fluoride in THF to provide the anti-alcohols 109 and 110. Compounds 109 and 110 were subsequently subjected to Mitsunobu inversion to afford the corresponding syn-alcohols 111 and 112.

For the preparation of inhibitors 103 and 129, alcohols 115 and 116 were synthesized as described in Scheme 10. Diol 106 was heated under reflux in toluene in the presence of dibutyltin oxide with azeotropical removal of water. The resulting stannylene acetal intermediate was treated with chloroethanol to obtain the monoalkylated derivative 113 in 68% overall yield. Subsequently, the primary alcohol was selectively tosylated with p-toluenesulfonyl chloride in the presence of pyridine. Exposure of the resulting compound to sodium hydride resulted in an intramolecular substitution reaction leading to the corresponding cyclization compound 114. n-Bu4N+F-mediated deprotection furnished the target antialcohol 115 in good overall yield. The syn-alcohol 16 was then obtained after Mitsunobu inversion of 115 as described above.

Scheme 10

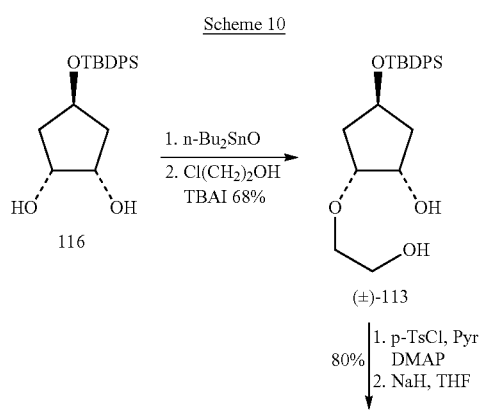

The synthesis of active carbonates required for various inhibitors is shown in Scheme 11. Alcohol 109 was converted to the succinimidyl-derivative 117 by treatment with N,N'-disuccinimidylcarbonate in the presence of Et3N as described previously (Ghosh, A. K.; et al., Tetrahedron Lett., 1992, 33, 2781). Alcohols 110-112 and 115, 116 were activated by conversion to the corresponding p-nitrophenylcarbamates 118-122 (81-95% yield) by using p-nitrophenylchloroformate and N-methylmorpholine in THF.

Scheme 11

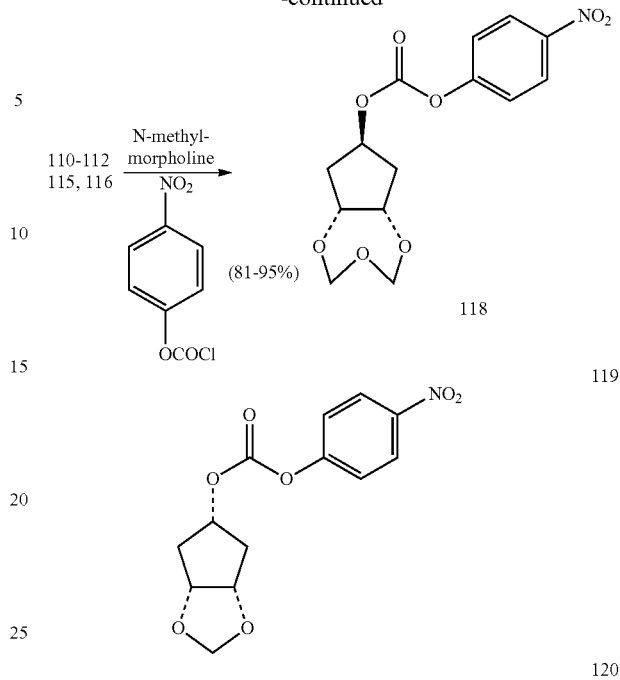

The general procedure for the synthesis of inhibitors 102, 103, 126-130 is outlined in Scheme 12. Epoxide 123 (Ghosh, A. K.; Fidanze, S.; J. Org. Chem. 1998, 63, 6146) was converted into intermediate 124 following a previously reported procedure (see, for example, Ghosh, 2006). Deprotection of 124 by using trifluoroacetic acid followed by reaction with activated alcohols 117-122 furnished inhibitors 102-103, 126-129 in 43-85% yields.

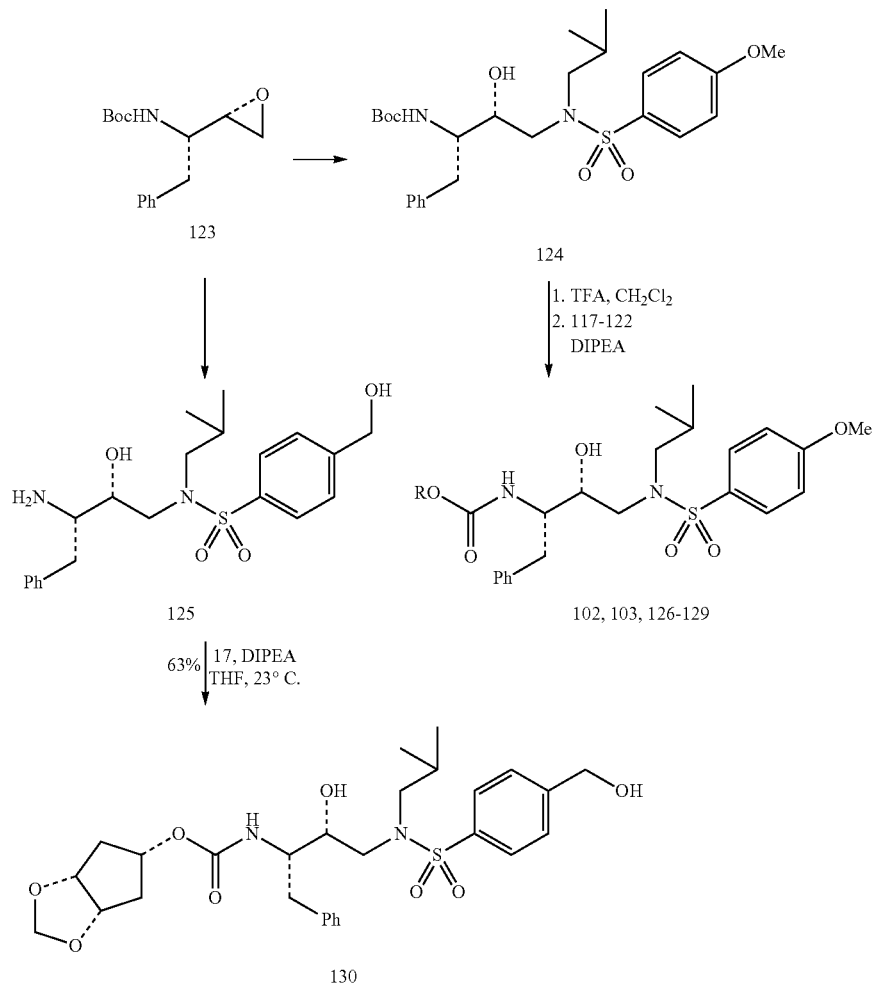

Scheme 12

In one illustrative example, compound 130 was synthesized from the known amine 125 (see, for example, Ghosh, 2006) and activated carbonate 117 in the presence of diisopropylethylamine in THF at 23° C. Inhibitor 130 was obtained in 63% yield. The foregoing examples are presented for the purpose of illustration only and are not intended to limit the scope of the invention. While certain embodiments of the present invention have been described and/or exemplified above, it is contemplated that considerable variation and modification thereof are possible. Accordingly, the present invention is not limited to the particular embodiments described and/or exemplified herein.

It is to be understood that though each of the foregoing illustrative embodiments of processes are shown for a particular compound or subgenus of compounds, in each case, the processes may be adapted to the preparation of other compounds described herein using routine methods and the selection of the corresponding starting compounds.

It is also appreciated that in the foregoing embodiments, certain aspects of the compounds are presented in the alternative, such as selections for any one or more of A, B, $R^a$, $R^b$, $R^c$, $R^d$, $W^1$, $W^2$, $W^3$, $W^4$, $W^5$, V, X, Y, and Z. It is therefore to be understood that various alternate embodiments of the invention include individual members of those lists, as well as the various subsets of those lists. Each of those combinations are to be understood to be described herein by way of the lists. For example, in one such alternative embodiments, compounds are described wherein A is an alkyl, Y is $SO_2$, B is an arylalkyl, $W^1$ is methylene and $W^2$ is a polyether.

It is also to be understood that in each of the foregoing embodiments the isotopic distribution in any one or more atom locations may be that corresponding to the natural abundance, or in the alternative various isotopically enriched variations thereof. Illustratively, deuterated variations of any of the foregoing embodiments are also described herein. It is appreciated that deuteration at one or more locations may lead to positively altered bioavailability, metabolism, or potency profiles.

METHODS AND EXAMPLES

GENERAL. All moisture sensitive reactions were carried out under nitrogen or argon atmosphere. Anhydrous solvents were obtained as follows: THF, diethyl ether, and benzene, distilled from sodium and benzophenone; dichloromethane, pyridine, triethylamine, and diisopropylethylamine, distilled from $CaH_2$. All other solvents were HPLC grade. Column chromatography was performed with Whatman 240-400 mesh silica gel under low pressure (5-10 psi). TLC was carried out with E. Merck silica gel 60-F-254 plates. 1H and 13C NMR spectra were recorded on Varian Mercury 300 and Bruker Avance 400 and 500 spectrometers. Optical rotations were measured using a Perkin-Elmer 341 polarimeter.

Example 1

(S)-2-(tert-Butyldiphenylsilyloxy)pentanedioic acid dimethyl ester (5). A mixture of (2S)-hydroxypentadienoic acid dimethyl ester 4 (Winitz, M.; et al., 1956) (0.39 g, 2.2 mmol), imidazole (0.45 g, 6.6 mmol) and tert-butyldiphenylsilyl chloride (1.2 mL, 4.4 mmol) in dry DMF (4 mL) was stirred at 23° C. for 4 h. Subsequently, the reaction mixture was poured into water and the aqueous phase was extracted with $Et_2O$, the organic extracts were washed with 1 N HCl and brine, dried ($Na_2SO_4$) and the solvent was removed. The residue was purified by flash-chromatography (1:10 EtOAc/Hex) to furnish 0.89 g (90%) of 5 as a colourless oil: $[\alpha]_D^{20}=-21.1$ (c 9.0, $CHCl_3$); $^1H$ NMR ($CDCl_3$) δ 7.69-7.62 (m, 4H), 7.46-7.33 (m, 6H), 4.31 (t, J=5.4 Hz, 1H), 3.64 (s, 3H), 3.45 (s, 3H), 2.57-2.34 (m, 2H), 2.14-2.04 (m, 2H), 1.11 (s, 9H); $^{13}C$ NMR ($CDCl_3$) δ 173.4, 172.9, 135.9, 135.7, 133.0, 132.9, 129.9, 129.8, 127.7, 127.5, 71.4, 51.6, 51.5, 29.9, 28.9, 26.9, 19.4.

Example 2

(S)-2-(tert-Butyldiphenylsilyloxy)pentan-1,5-diol (6a). Compound 5 (0.8 g, 1.8 mmol) was dissolved in dry $Et_2O$ (8.5 mL) and the solution was cooled to 0° C., afterward lithium borohydride (0.12 g, 5.4 mmol) and dry methanol (0.22 mL, 5.4 mmol) were sequentially added. The resulting suspension was stirred at 23° C. for 24 h, then a few drops of 6 N HCl were added and the salts were filtered off. The filtrate was concentrated under reduced pressure and the residue was purified by flash-chromatography (1:1 EtOAc/Hex) to furnish 0.61 g (93%) of 6a as a colourless oil: $[\alpha]_D^{20}=-15.6$ (c 3.1, $CHCl_3$); $^1H$ NMR ($CDCl_3$) δ 7.70-7.65 (m, 4H), 7.44-7.32 (m, 6H), 3.82-3.77 (m, 1H), 3.53-3.48 (m, 2H), 3.45-3.41 (m, 2H), 1.65-1.47 (m, 4H), 1.05 (s, 9H); $^{13}C$ NMR ($CDCl_3$) δ 135.9, 135.7, 133.8, 133.7, 130.1, 129.8, 127.7, 127.6, 73.6, 65.7, 62.7, 29.7, 28.0, 27.0, 19.3.

Example 3

(S)-1-(tert-Butyldiphenylsilyloxy)-3,5-dioxacyclooctane (7a). To a mixture of 6a (0.55 g, 1.5 mmol) and paraformaldehyde (46 mg, 1.5 mmol) in EtOAc (30 mL), boron trifluoride etherate (195 μL, 1.5 mmol) was added and the resulting mixture was stirred at 23° C. for 4 h. The organic phase was washed with a saturated solution of $NaHCO_3$, dried ($Na_2SO_4$) and the solvent was removed. The residue was purified by flash-chromatography (1:4 EtOAc/Hex) to afford 0.29 g (51%) of 7a as a colourless oil: $[\alpha]_D^{20}=-8.7$ (c 1.9, $CHCl_3$); $^1H$ NMR ($CDCl_3$) δ 7.67-7.63 (m, 4H), 7.45-7.34 (m, 6H), 4.69 (d, J=6.2 Hz, 1H), 4.45 (d, J=6.2 Hz, 1H), 4.03-3.95 (m, 1H), 3.70-3.61 (m, 1H), 3.59-3.48 (m, 3H), 1.93-1.80 (m, 1H), 1.77-1.61 (m, 2H), 1.47-1.34 (m, 1H), 1.12 (s, 9H); $^{13}C$ NMR ($CDCl_3$) δ 135.7, 134.2, 129.5, 127.5, 95.6, 72.2, 71.9, 69.0, 33.2, 27.0, 26.7, 19.2.

Example 4

(S)-O-Benzyl-3,5-dioxacyclohept-1-ol (7b). Compound 6b (Gmeiner, P.; et al., 1995) (50 mg, 0.26 mmol) was reacted as described for compound 6a to afford 44 mg (82%) of 7b after chromatographic purification (1:9 EtOAc/Hex): $[\alpha]_D^{20}=+64.6$ (c 1.2, $CHCl_3$); $^1H$ NMR ($CDCl_3$) δ 7.35-7.26 (m, 5H), 4.81-4.77 (m, 2H), 4.58 (s, 2H), 3.95-3.73 (m, 3H), 3.73-3.62 (m, 2H), 1.98-1.91 (m, 2H); $^{13}C$ NMR ($CDCl_3$) δ 138.3, 128.3, 127.5, 126.2, 94.9, 75.8, 70.7, 68.8, 62.6, 35.0.

Example 5

(S)-3,5-Dioxacyclooctan-1-ol (8a). Compound 7a (0.27 g, 0.74 mmol) was dissolved in dry THF (5 mL) and TBAF (1.0 M solution in THF, 0.81 mL, 0.81 mmol) was added. The resulting mixture was stirred at 23° C. overnight, afterward a saturated solution of $NaHCO_3$ was added, the solvent was removed and the aqueous phase was extracted with EtOAc. The organic extracts were dried and evaporated and the residue was purified by flash-chromatography (EtOAc) to afford 76 mg (77%) of 8a as a colourless oil: $[\alpha]_D^{20}$, −12.6 (c 1.6, $CHCl_3$); $^1H$ NMR ($CDCl_3$) δ 4.65 (d, J=6.0 Hz, 1H), 4.57 (d, J=6.0 Hz, 1H), 4.92-3.81 (m, 2H), 3.75-3.60 (m, 2H), 3.55 (dd, J=3.4, 12.1 Hz, 1H), 2.96 (bs, 1H), 1.95-1.69 (m, 3H), 1.65-1.53 (m, 1H); $^{13}C$ NMR ($CDCl_3$) δ 94.9, 73.7, 69.3, 68.2, 30.2, 24.7.

Example 6

(S)-3,5-Dioxacyclohept-1-ol (8b). To a solution of 7b (38 mg, 0.18 mmol) in EtOAc (3 mL), 10% Pd/C was added and the resulting suspension was stirred at 23° C. under a hydrogen atmosphere. After 12 h, the catalyst was filtered off, the filtrate was evaporated in vacuo and the residue (19 mg, 91%) was used in the next step without further purification: $[\alpha]_D^{20}=+12.9$ (c 0.9, $CHCl_3$); $^1H$ NMR ($CDCl_3$) δ 4.78-4.74 (m 2H), 3.93-3.91 (m, 1H), 3.81-3.75 (m, 4H), 2.51 (bs, 1H), 1.93-1.83 (m, 2H); $^{13}C$ NMR ($CDCl_3$) δ 94.4, 69.5, 68.4, 62.3, 37.8.

Example 7

(R)-3,5-Dioxacyclooctan-1-ol (8c). To a mixture of (S)-8a (46 mg, 0.35 mmol), p-nitrobenzoic acid (86 mg, 0.52 mmol), and triphenylphosphine (181 mg, 0.69 mmol), diisopropylazodicarboxylate (135 μL, 0.69 mmol) was added dropwise and the resulting mixture was stirred at 23° C. overnight. The solvent was removed under reduced pressure and the residue was purified by flash-chromatography (1:3 EtOAc/Hex). The resulting ester was dissolved in a 3:2:1 mixture of THF, methanol and water (4 mL) and $LiOH·H_2O$ (72 mg, 1.7 mmol) was added. The yellow mixture was stirred at 23° C. overnight and then the solvent was removed in vacuo, the residue was diluted with water and the aqueous phase was extracted with ether. The organic extracts were dried ($Na_2SO_4$) and the solvent evaporated. Purification of the residue by flash-chromatography (EtOAc) afforded 20 mg (44%) of (R)-8c as a colourless liquid. $[\alpha]_D^{20}=+12.1$ (c 1.4, $CHCl_3$). $^1H$ and $^{13}C$ NMR are consistent with those reported for the (S)-enantiomer 8a Example 8

(R)-3,5-Dioxacyclohept-1-ol (8d). The title compound was obtained from 8b as described for (S)-8c in 73% yield. Flash-chromatography was performed using a 1:1 mixture of EtOAc and $CHCl_3$ as the eluant: $[\alpha]_D^{20}=-12.6$ (c 1.3, $CHCl_3$). $^1H$ and $^{13}C$ NMR are consistent with those reported for the (S)-enantiomer 8b

Example 9

(R)-1-(tert-Butyldimethylsilyloxy)-2-[(2-methoxyethoxy)methoxy]pent-4-ene (10). To a mixture of 9 (350 mg, 1.6 mmol) and diisopropylethylamine (1.2 mL, 7.2 mmol) in $CH_2Cl_2$ (8 mL), cooled to 0° C., MEM-Cl (550 µL, 4.8 mmol) was added and the resulting mixture was stirred at 23° C. for 56 h. The organic phase was washed with 0.1 N HCl, brine and dried ($Na_2SO_4$). The solvent was removed and the residue was purified by flash-chromatography (1:10 EtOAc/Hex) to afford 440 mg (90%) of 10 as a colourless oil: $[\alpha]_D^{20}=+12.0$ (c 1.1, $CHCl_3$); $^1$H NMR ($CDCl_3$) δ 5.88-5.74 (m, 1H), 5.11-5.01 (m, 2H), 4.82 (d, J=6.9 Hz, 1H), 4.74 (d, J=6.9 Hz, 1H), 3.76-3.63 (m, 3H), 3.60-3.51 (m, 4H), 3.37 (s, 3H), 2.38-2.19 (m, 2H), 0.86 (s, 9H), 0.02 (s, 6H); $^{13}$C NMR ($CDCl_3$) δ 134.6, 117.0, 94.8, 77.4, 71.6, 66.7, 65.0, 58.9, 36.0, 25.7, 18.2, −5.5.

Example 10

(R)-1-Allyloxy-2-[(2-methoxyethoxy)methoxy]pent-4-ene (11). A mixture of 10 (440 mg, 1.4 mmol) and TBAF (1.0 M solution in THF, 4.7 mL, 4.7 mmol) in THF (3 mL) was stirred at 23° C. for 3 h, afterward a saturated solution of $NaHCO_3$ was added, the solvent was removed and the aqueous phase was extracted with $CHCl_3$. The organic extracts were dried ($Na_2SO_4$) and the solvent was removed. The residue was purified by flash-chromatography to afford 237 mg (87%) of (R)-2-[(2-methoxyethoxy)methoxy]pent-4-en-1-ol as a colourless oil: $[c]_D^{20}=−55.0$ (c 1.3, $CHCl_3$); $^1$H NMR ($CDCl_3$) δ 5.85-5.71 (m, 1H), 5.11-5.02 (m, 2H), 4.81 (d, J=7.5 Hz, 1H), 4.75 (d, J=7.5 Hz, 1H), 3.87-3.80 (m, 1H), 3.71-3.61 (m, 3H), 3.59-3.46 (m, 3H), 3.37 (s, 3H), 3.22 (bs, 1H), 2.36-2.19 (m, 2H); $^{13}$C NMR ($CDCl_3$) δ 134.1, 117.3, 95.4, 81.0, 71.5, 67.3, 64.8, 58.9, 36.2. To a mixture of the above compound (240 mg, 1.25 mmol), allyl bromide (225 µL, 1.9 mmol) and a catalytic amount of TBAI in THF (12 mL), at 0° C., sodium hydride (60% dispersion in oil, 102 mg, 2.5 mmol) was added in small portions. After 30 min, the reaction mixture was allowed to warm to 23° C. and was stirred at the same temperature for 18 h. Subsequently, the reaction was quenched with a saturated solution of $NH_4Cl$, the organic solvent was removed and the aqueous phase was extracted with $CHCl_3$. The organic extracts were dried ($Na_2SO_4$) and the solvent was evaporated. The residue was purified by flash-chromatography (10:1 $CHCl_3$/EtOAc) to afford 229 mg (80%) of 11 as a colourless oil. $[\alpha]_D^{20}$, −5.2 (c 3.1, $CHCl_3$); $^1$H NMR ($CDCl_3$) δ 5.87-5.79 (m, 2H), 5.34 (dd, J=1.3, 19.1 Hz, 1H), 5.16-5.03 (m, 3H), 4.81 (d, J=7.0 Hz, 1H), 4.77 (d, J=7.0 Hz, 1H), 3.98-3.97 (m, 2H), 3.84-3.81 (m, 1H), 3.72 (t, J=5.0 Hz, 2H), 3.54 (t, J=5.0 Hz, 2H), 3.46-3.44 (m, 2H), 3.38 (s, 3H), 2.35-2.31 (m, 2H); $^{13}$C NMR ($CDCl_3$) δ 134.6, 134.3, 117.3, 116.7, 94.6, 75.3, 72.1, 71.9, 71.6, 66.7, 58.9, 36.3.

Example 11

(R,Z)-3-[(2-Methoxyethoxy)methoxy]-2,3,4,7-tetrahydrooxepine (12). A mixture of 11 (100 mg, 0.43 mmol) and 2nd generation Grubbs catalyst (18 mg, 0.02 mmol) in $CH_2Cl_2$ (10 mL) was heated to 45° C. for 1 h. After this time, the solvent was removed and the residue was purified by flash-chromatography (5:1 $CHCl_3$/EtOAc) to afford 83 mg (94%) of 12 as a colourless oil: $^1$H NMR ($CDCl_3$) δ 5.87-5.66 (m, 2H), 4.77-4.18 (m, 2H), 4.18-4.14 (m, 2H), 4.01-3.89 (m, 2H), 3.75-3.68 (m, 3H), 3.56-3.53 (m, 2H), 3.38 (s, 3H), 2.54-2.51 (m, 2H); $^{13}$C NMR ($CDCl_3$) δ 130.6, 125.9, 94.3, 75.6, 75.1, 71.6, 70.3, 66.8, 58.9, 31.8.

Example 12

(R)-Oxepan-3-ol (8e). A mixture of 12 (90 mg, 0.44 mmol) and a catalytic amount of 10% Pd/C in EtOAc (3 mL) was stirred at 23° C. under a hydrogen atmosphere for 3 h. After this time, the catalyst was filtered off through a pad of Celite and the filtrate was concentrated under reduced pressure to afford (R)-3-[(2-methoxyethoxy)methoxy]oxepane (83 mg, 92%) as a colourless oil: $^1$H NMR ($CDCl_3$) δ 4.70 (d, J=7.2 Hz, 1H), 4.67 (d, J=7.2 Hz, 1H), 3.83-3.58 (m, 7H), 3.50 (t, J=4.6 Hz, 2H), 3.34 (s, 3H), 1.72-1.67 (m, 1H), 1.46-1.44 (m, 4H), 1.22-1.19 (m, 1H); $^{13}$C NMR ($CDCl_3$) δ 93.9, 76.5, 73.7, 71.8, 71.6, 66.7, 58.8, 32.6, 30.7, 20.9. A mixture of the above compound (50 mg, 0.24 mmol) and 6 N HCl (0.5 mL) in THF (2 mL) was stirred at 23° C. for 16 h. The solvent was removed and the aqueous phase was extracted with $CHCl_3$. The organic extracts were washed with a saturated solution of $NaHCO_3$, dried ($Na_2SO_4$) and the solvent was removed. The residue was purified by flash-chromatography (1:4 EtOAc/$CHCl_3$) to afford 8e (24 mg, 84%) as a colourless oil: $[\alpha]_D^{20}=−4.2$ (c 0.8, $CHCl_3$); $^1$H NMR ($CDCl_3$) δ 3.87-3.85 (m, 1H), 3.76-3.62 (m, 4H), 2.37 (bs, 1H), 1.78-1.65 (m, 5H), 1.54-1.52 (m, 1H); $^{13}$C NMR ($CDCl_3$) δ 73.2, 70.7, 70.4, 36.4, 30.0, 20.2.

Example 13

(R)-3-(tert-Butyldimethylsilyloxy)-5-(allyloxy)pent-1-ene (14). A mixture of 13 (50 mg, 0.23 mmol), allyl bromide (30 µL, 0.35 mmol) and a catalytic amount of TBAI was cooled to 0° C. and sodium hydride (60% in mineral oil, 11 mg, 0.28 mmol) was added. The resulting mixture was allowed to warm to 23° C. and stirred for 18 h. The reaction was quenched by adding a saturated solution of $NH_4Cl$, the solvent was removed and the aqueous phase was extracted with $CHCl_3$. The organic extracts were dried ($Na_2SO_4$) and the solvent was removed. The residue was purified by flash-chromatography (1:20 EtOAc/Hex) to afford 57 mg (97%) of 14 as a colorless oil: $^1$H NMR ($CDCl_3$) δ 5.96-5.87 (m, 1H), 5.85-5.78 (m, 1H), 5.29-5.24 (m, 1H), 5.19-5.13 (m, 2H), 5.04-5.00 (m, 1H), 4.31-4.26 (m, 1H), 3.96-3.94 (m, 2H), 3.55-3.42 (m, 2H), 1.84-1.67 (m, 2H), 0.90 (s, 9H), 0.06 (s, 3H), 0.02 (s, 3H); $^{13}$C NMR ($CDCl_3$) δ 141.5, 134.9, 116.6, 113.6, 71.8, 70.6, 66.5, 38.0, 25.8, 18.1, −4.5, −5.1.

Example 14

(R,Z)-4-(tert-Butyldimethysilyloxy)-2,3,4,7-tetrahydrooxepine (15). The title compound was obtained from 14 as described for 12 in 80% yield. Flash-chromatography was performed using a 1:10 mixture of EtOAc and Hex as the eluant: $^1$H NMR ($CDCl_3$) δ 5.79-5.75 (m, 1H), 5.63-5.60 (m, 1H), 4.64-4.62 (m, 1H), 4.14-4.12 (m, 2H), 3.91-3.85 (m, 1H), 3.80-3.74 (m, 1H), 2.11-2.05 (m, 1H), 1.96-1.91 (m, 1H), 0.90 (s, 9H), 0.08 (s, 3H), 0.07 (s, 3H); $^{13}$C NMR ($CDCl_3$) δ 138.4, 127.8, 69.9, 68.2, 67.4, 38.8, 25.8, 18.3, −4.8.

Example 15

(S)-Oxepan-4-ol (8f). Hydrogenolysis of 15 was carried out as described for 8e to afford (S)-4-(tert-butyldimethylsilyloxy)oxepane in 95% yield as a colourless oil: $^1$H NMR ($CDCl_3$) δ 4.03-3.96 (m, 1H), 3.79-3.57 (m, 4H), 1.98-1.69

(m, 5H), 1.64-1.51 (m, 1H), 0.88 (s, 9H), 0.044 (s, 3H), 0.038 (s, 3H); $^{13}$C NMR (CDCl$_3$) δ 70.2, 69.4, 64.2, 40.1, 34.5, 25.7, 23.7, 18.0, −4.9. Deprotection of the above compound was performed as described for compound 11 and afforded the title compound in 75% yield as a colorless oil: $^1$H NMR (CDCl$_3$) δ 4.03-3.98 (m, 1H), 3.82-3.59 (m, 4H), 2.02-1.98 (m, 1H), 1.89-1.80 (m, 4H), 1.66-1.64 (m, 1H); $^{13}$C NMR (CDCl$_3$) δ 70.5, 69.6, 64.7, 38.9, 34.9, 24.3.

Example 16

2-(Benzyloxy)propane-1,3-diol (17). To a solution of 16 (2.5 g, 13.8 mmol) in dry THF (20 mL), cooled to 0° C., NaH (60% in mineral oil, 0.56 g, 14 mmol) was added portionwise. After 30 min, tetra-n-butylammonium iodide (51 mg, 0.14 mmol) and a solution of benzyl bromide (1.65 mL, 13.9 mmol) in THF (5 mL) were added. The reaction mixture was stirred at 23° C. for 3 h, afterward it was poured into ice. The organic solvent was removed in vacuo and the aqueous phase was extracted with CHCl$_3$. The organic extracts were dried (Na$_2$SO$_4$) and the solvent was removed. The crude 5-(benzyloxy)-2-phenyl-1,3-dioxane thus obtained was dissolved in a 1:1 mixture of THF and H$_2$O (60 mL) and to the resulting solution, 6 N HCl was slowly added to the resulting solution. After stirring at 23° C., the reaction mixture was brought to pH 8 by addition of a saturated solution of NaHCO$_3$, the solvent was removed and the aqueous phase was extracted with diethyl ether. The organic extracts were dried and evaporated and the residue was purified by flash-column chromatography (EtOAc 2: Hex 1) to afford the title compound as a colourless oil in quantitative yield. Physical and spectroscopic data are consistent with those reported in the literature (Hronowski, L. J. J.; et al., Synthesis and characterization of 1-O-_-lactosyl-(R,S)-glycerols and 1,3-di-O-_-lactosylglycerol. *Carbohydrate Res.* 1989, 190, 203-218).

Example 17

1,3-Dioxan-5-ol (8h). To a mixture of 17 (100 mg, 0.55 mmol) and paraformaldehyde (17 mg, 0.55 mmol) in EtOAc (10 mL), boron trifluoride etherate (70 μL, 0.55 mmol) was added and the reaction mixture was stirred at 23° C. for 4 h. The organic phase was washed with a saturated solution of NaHCO$_3$, dried and the solvent was removed. The residue was purified by flash-chromatography eluting with a 1:4 mixture of EtOAc and hexanes to afford 84 mg (78%) of O-benzyl-1,3-dioxan-5-ol as a colourless oil. The above compound was dissolved in EtOAc (3 mL), Pd/C was added and the resulting suspension was stirred at rt under a hydrogen atmosphere. After 12 h, the catalyst was filtered off, the filtrate was evaporated in vacuo and the residue (39 mg, 100%) was used in the next step without further purification: $^1$H NMR (CDCl$_3$) δ 4.93 (d, J=6.3 Hz, 1H), 4.76 (d, J=6.3 Hz, 1H), 3.94-3.84 (m, 4H), 3.64-3.61 (m, 1H), 2.78 (bs, 1H). $^{13}$C NMR (CDCl$_3$) δ 94.0, 71.7, 64.1.

Example 18

O-Benzyl-3,6,9-trioxacyclodecan-1-ol (18). To a refluxing suspension of sodium hydride (60% in mineral oil, prewashed with hexane, 84 mg, 2.1 mmol) in dry THF (5 mL), a solution of 17 (182 mg, 1.0 mmol) and di(ethyleneglycol) dimethanesulfonate (260 mg, 1.0 mmol) in dry THF (5 mL) was added dropwise. The resulting mixture was heated under reflux for 20 h, afterward was cooled to 23° C. and H$_2$O (2 mL) was added. The solvent was removed and the aqueous phase was extracted with CHCl$_3$. The organic extracts were washed several times with water, dried (Na$_2$SO$_4$) and evaporated. The residue was purified by flash-chromatography (2:3 CH$_2$Cl$_2$/EtOAc) to afford 49 mg (19%) of 18 as a colourless oil: $^1$H NMR (CDCl$_3$) δ 7.36-7.26 (m, 5H), 4.66 (s, 2H), 3.75-3.57 (m, 13H); MS (ESI) m/z 275 [M+Na]$^+$.

Example 19

O-Benzyl-3,6,9,12-tetraoxacyclotridecan-1-ol (19). Compound 19 was obtained as described for 18 starting from 17 and tri(ethyleneglycol)dimethanesulfonate in 29% yield. $^1$H NMR (CDCl$_3$) δ 7.39-7.26 (m, 5H), 4.72 (s, 2H), 3.83-3.58 (m, 17H); MS (ESI) m/z 319 [M+Na]$^+$.

Example 20

3,6,9-Trioxacyclodecan-1-ol (8i). A mixture of 18 (34 mg, 0.13 mmol) and a catalytic amount of 10% Pd/C in methanol (2 mL) was stirred at 23° C. under a hydrogen atmosphere. After 18 h the catalyst was filtered off and the filtrate was evaporated to afford 22 mg (99%) of 81 as a colourless oil: $^1$H NMR (CDCl$_3$) δ 3.74-3.53 (m, 13H), 2.73 (bs, 1H).

Example 21

3,6,9,12-Tetraoxacyclotridecan-1-ol (8j). Starting from 19, compound 8j was obtained as described for 81 in quantitative yield: $^1$H NMR (CDCl$_3$) δ 3.81-3.60 (m, 17H), 2.95 (bs, 1H).

Example 22

3,6,8,11-Tetraoxa-1-cyclododecanol (8k). To a mixture of 20 (Kasireddy, K.; et al., 2004) (78 mg, 0.29 mmol) and paraformaldehyde (8.7 mg, 0.29 mmol) in EtOAc (4 mL), boron trifluoride etherate (37 μL, 0.29 mmol) was added and the resulting mixture was stirred at 23° C. for 2 h. Subsequently, a saturated solution of NaHCO$_3$ was added and the aqueous phase was extracted with EtOAc. The combined organic extracts were dried (Na$_2$SO$_4$) and the solvent was removed in vacuo. The residue was purified by flash-chromatography to afford 31 mg (37%) of O-benzyl-3,6,8,11-tetraoxacyclododecan-1-ol as a colourless oil: $^1$H NMR (CDCl$_3$) δ 7.35-7.27 (m, 5H), 4.67 (s, 2H), 3.88 (s, 2H), 3.86-3.81 (m, 2H), 3.77-3.61 (m, 11H); $^{13}$C NMR (CDCl$_3$) δ 133.6, 128.3, 127.7, 126.2, 94.6, 75.8, 71.5, 69.6, 65.3, 64.6; MS (ESI) m/z 305 [M+Na]$^+$. A mixture of the above compound and a catalytic amount of 10% Pd/C in EtOAc (2 mL) was stirred at 23° C. under a hydrogen atmosphere. After 18 h the catalyst was filtered off and the filtrate was evaporated to afford 21 mg (99%) of 8k as a colorless oil: $^1$H NMR (CDCl$_3$) δ 4.67 (s, 2H), 3.85-3.63 (m, 11H), 3.54 (dd, J=6.4, 8.2 Hz, 2H), 2.22 (d, J=8.7 Hz, 1H).

Example 23

O-Benzyl-3,9-dioxa-6-thiacyclodecan-1-ol 6,6-dioxide (22). A solution of lithium sulfide (11 mg, 0.23 mmol) in water (0.3 mL) was added dropwise within 30 min to a solution of 21 (Kasireddy, K.; 2004) (60 mg, 0.15 mmol) in refluxing ethanol (15 mL). The resulting mixture was heated under reflux for 3 h and then was cooled to 23° C. The solvent was removed and the aqueous phase was extracted with CHCl$_3$. The organic extracts were dried (Na$_2$SO$_4$) and the solvent was removed. Flash-chromatography of the residue (1:4 EtOAc/hexanes) afforded 16 mg (38%) of O-benzyl-3, 9-dioxa-6-thiacyclodecan-1-ol as a colorless oil: $^1$H NMR (CDCl$_3$) δ 7.36-7.27 (m, 5H), 4.59 (s, 2H), 3.90-3.85 (m, 2H), 3.82-3.48 (m, 7H), 2.91-2.74 (m, 4H); $^{13}$C NMR (CDCl$_3$) δ 133.5, 128.3, 127.7, 126.0, 75.9, 71.9, 71.6, 68.0, 33.4. MS (ESI) m/z 291 [M+Na]$^+$, 286 [M+H+NH$_3$]$^+$, 269 [M+H]$^+$. To a solution of the above compound (11 mg, 0.040 mmol) in CH$_2$Cl$_2$ (2 mL), cooled to 0° C., m-chloroperbenzoic acid (77%, 22 mg, 0.09 mmol) was added in small portions. After 18 h, a 1% solution of sodium bisulfite was added, the layers were separated and the organic phase was washed with a saturated solution of NaHCO$_3$. The organic extracts were dried (Na$_2$SO$_4$) and evaporated. The residue was purified by flash-chromatography (1:4 EtOAc/CHCl$_3$) to afford 11 mg (93%) of 22 as a brown oil: $^1$H NMR (CDCl$_3$) δ 7.37-7.29 (m, 5H), 4.57 (s, 2H), 4.01-3.96 (m, 4H), 3.77-3.72 (m, 1H), 3.66-3.60 (m, 4H), 3.40-3.38 (m, 2H), 3.34-3.23 (m, 2H); $^{13}$C NMR (CDCl$_3$) δ 133.4, 128.4, 127.9, 127.7, 74.7, 71.8, 66.4, 64.6, 52.4.

Example 24

3,9-Dioxa-6-thiacyclodecan-1-ol 6,6-dioxide (81). A mixture of 22 (25 mg, 0.083 mmol) and a catalytic amount of 10% Pd/C in EtOAc (3 mL) was stirred at 23° C. under a hydrogen atmosphere. After 48 h the catalyst was filtered off and the filtrate was evaporated to afford 16 mg (92%) of 81 as a colorless oil: $^1$H NMR (CDCl$_3$) δ 4.08-3.95 (m, 4H), 3.67 (dd, J=4.2, 9.9 Hz, 2H), 3.61-3.59 (m, 1H), 3.51 (dd, J=5.7, 9.9 Hz, 2H), 3.38-3.23 (m, 4H); $^{13}$C NMR (CDCl$_3$) δ 69.0, 68.3, 64.5, 52.6.

Example 25

O,6-Dibenzyl-3,9-dioxa-6-azocyclodecan-1-ol (23). A mixture of 21 (Kasireddy, K.; et al., 2004) (150 mg, 0.37 mmol), benzylamine (41 μL, 0.37 mmol), lithium perchlorate (340 mg, 3.7 mmol) and sodium carbonate (200 mg, 1.9 mmol) in acetonitrile (7.5 mL) was heated under reflux for 48 h. After cooling to 23° C., the solvent was removed, the residue was suspended in CHCl$_3$ and the organic phase was washed with water and dried (Na$_2$SO$_4$). Flash-chromatography of the residue (2:1 EtOAc/CHCl$_3$) afforded 31 mg (24%) of 23 as a colourless oil: $^1$H NMR (CDCl$_3$) δ 7.36-7.20 (m, 10H), 4.59 (s, 2H), 3.87-3.78 (m, 4H), 3.69 (s, 2H), 3.67-3.49 (m, 5H), 2.91-2.72 (m, 4H); MS (ESI) m/z 342 [M+1]$^+$.

Example 26

N-(tert-Butoxycarbonyl)-3,9-dioxa-6-azocyclodecan-1-ol (24). A mixture of 23 (40 mg, 0.12 mmol), Boc$_2$O (26 mg, 0.12 mmol) and a catalytic amount of 10% Pd/C in EtOAc (3 mL) was stirred at 23° C. under a hydrogen atmosphere. After 18 h the catalyst was filtered off and the filtrate was evaporated to afford 26 mg (95%) of 24 as a colorless oil: $^1$H NMR (CDCl$_3$) δ 3.83-3.70 (m, 7H), 3.65-3.59 (m, 2H), 3.49-3.29 (m, 4H), 1.75 (bs, 1H), 1.46 (s, 9H); $^{13}$C NMR (CDCl$_3$) δ 155.7, 79.8, 71.4, 71.0, 70.3, 69.9, 50.5, 50.2, 28.5.

Example 28

(S)-1-(4-Nitrophenoxycarbonyloxy)-3,5-dioxacyclooctane (25a). To a solution of 8a (15 mg, 0.11 mmol) and N-methylmorpholine (38 μL, 0.34 mmol) in dry THF (3 mL), p-nitrophenylchloroformate (70 mg, 0.28 mmol) was added and the resulting mixture was stirred at 23° C. for 1 h. To the reaction mixture was added water, the solvent was removed under reduced pressure and the aqueous phase was extracted with CHCl$_3$. The organic extracts were dried (Na$_2$SO$_4$) and the solvent was removed. The residue was purified by flash-chromatography (1:4 EtOAc CHCl$_3$) to afford 28 mg (81%) of 25a as a pale yellow solid. $^1$H NMR (CDCl$_3$) δ 8.27 (d, J=9.3 Hz, 2H), 7.38 (d, J=9.3 Hz, 2H), 5.09-5.01 (m, 1H), 4.72-4.66 (m, 2H), 3.94-3.82 (m, 3H), 3.64-3.56 (m, 1H), 2.18-2.04 (m, 1H), 2.03-1.93 (m, 2H), 1.90-1.71 (m, 1H).

Example 29

(S)-1-(4-Nitrophenoxycarbonyloxy)-3,5-dioxacycloheptane (25b). The title compound was obtained from (S)-8b as described for 25a in 72% yield. Flash-chromatography was performed using a 1:5 mixture of EtOAc and CHCl$_3$ as the eluant. $^1$H NMR (CDCl$_3$) δ 8.28 (d, J=9.3 Hz, 2H), 7.40 (d, J=9.3 Hz, 2H), 5.00-4.98 (m, 1H), 4.84 (d, J=4.5 Hz, 1H), 4.79 (d, J=4.5 Hz, 1H), 4.11 (dd, J=4.7, 13.1 Hz, 1H), 3.99-3.90 (m, 2H), 3.85-3.78 (m, 1H), 2.19-2.04 (m, 2H).

Example 30

(R)-1-(4-Nitrophenoxycarbonyloxy)-3,5-dioxacyclooctane (25c). The title compound was obtained from (R)-8c as described for 25a in 87% yield after flash-chromatography (1:4 EtOAc/CHCl$_3$). $^1$H NMR data are consistent with those reported for the (S)-enantiomer 25a Example 31

(R)-1-(4-Nitrophenoxycarbonyloxy)-3,5-dioxacycloheptane (25d). The title compound was obtained from (R)-8d as described for 25a in 70% yield after flash-chromatography (1:5 EtOAc/CHCl$_3$). $^1$H data are consistent with those reported for the (S)-enantiomer 25b.

Example 32

(R)-3-(4-Nitrophenoxycarbonyloxy)oxepane (25e). The title compound was obtained from 8e as described for 25a in 86% yield. Flash-chromatography was performed using a 1:20 mixture of EtOAc and CHCl$_3$ as the eluant; $^1$H NMR (CDCl$_3$) δ 8.26 (d, J=9.3 Hz, 2H), 7.38 (d, J=9.3 Hz, 2H), 5.02-4.95 (m, 1H), 3.98-3.83 (m, 3H), 3.71-3.63 (m, 1H), 2.15-1.74 (m, 5H), 1.65-1.53 (m, 1H).

Example 33

(S)-4-(4-Nitrophenoxycarbonyloxy)oxepane (25f). The title compound was obtained from 8f as described for 25a in 77% yield. Flash-chromatography was performed using a 1:20 mixture of EtOAc and CHCl$_3$ as the eluant; $^1$H NMR (CDCl$_3$) δ 8.27 (d, J=8.8 Hz, 2H), 7.36 (d, J=8.8 Hz, 2H), 5.05-5.01 (m, 1H), 3.84-3.62 (m, 4H), 2.18-1.86 (m, 5H), 1.78-1.63 (m, 1H).

Example 34

1-(4-Nitrophenoxycarbonyloxy)cycloheptane (25g). The title compound was obtained from commercially available cycloheptanol as described for 25a in 89% yield. Flash-chromatography was performed using a 1:10 mixture of EtOAc and CHCl$_3$ as the eluant. $^1$H NMR (CDCl$_3$) δ 8.26 (d, J=8.7 Hz, 2H), 7.37 (d, J=8.7 Hz, 2H), 4.96-4.89 (m, 1H), 2.08-2.02 (m, 2H), 1.86-1.78 (m, 2H), 1.71 (m, 2H), 1.59 (m, 4H), 1.40-1.36 (m, 2H).

Example 35

5-(4-Nitrophenoxycarbonyloxy)-1,3-dioxane (25h). The title compound was obtained from 8h as described for 25a in 72% yield. Flash-chromatography was performed using a 1:4 mixture of EtOAc and CHCl$_3$ as the eluant: $^1$H NMR (CDCl$_3$) δ 8.30 (d, J=8.7 Hz, 2H), 7.42 (d, J=8.7 Hz, 2H), 5.03 (d, J=6.3 Hz, 1H), 4.87 (d, J=6.3 Hz, 1H), 4.71 (t, J=2.8 Hz, 1H), 4.19-4.06 (m, 4H).

Example 36

3,6,9-Trioxa-1-cyclodecanol succinimidylcarbonate (25i). To a solution of 8i (18 mg, 0.11 mmol) in dry acetonitrile (1 mL), N,N'-disuccimidyl carbonate (43 mg, 0.17 mmol) and triethylamine (32 μL, 0.23 mmol) were added and the resulting mixture was stirred at 23° C. After 8 h the solvent was removed, the residue was taken-up in a saturated solution of NaHCO$_3$ and the aqueous phase was extracted with EtOAc. The organic extracts were dried (Na$_2$SO$_4$) and the solvent was removed in vacuo. Purification of the residue (10:1 EtOAc/MeOH) afforded 17b (13 mg) in 37% yield: $^1$H NMR (CDCl$_3$) δ 5.12-5.03 (m, 1H), 3.96-3.65 (m, 12H), 2.81 (s, 4H).

Example 37

12-(4-Nitrophenoxycarbonyloxy)-1,4,7,10-tetraoxacyclotridecane (25j). The title compound was obtained from 8j as described for 25a in 70% yield after flash-chromatography (EtOAc): $^1$H NMR (CDCl$_3$) δ 8.27 (d, J=9.3 Hz, 2H), 7.39 (d, J=9.3 Hz, 2H), 5.15-5.08 (m, 1H), 3.92 (dd, J=6.3, 10.2 Hz, 2H), 3.82 (dd, J=4.5, 10.2 Hz, 2H), 3.74-3.60 (m, 12H).

Example 38

9-(4-Nitrophenoxycarbonyloxy)-1,7-dioxa-4-thiacyclodecane 4,4-dioxide (25k). The title compound was obtained from 8k as described for 25a in 73% yield after flash-chromatography (1:4 EtOAc/CHCl$_3$): $^1$H NMR (CDCl$_3$) δ 8.28 (d, J=9.0 Hz, 2H), 7.37 (d, J=9.0 Hz, 2H), 5.10-5.03 (m, 1H), 4.13-4.06 (m, 4H), 3.83-3.73 (m, 4H), 3.43-3.22 (m, 4H).

Example 39

11-(4-Nitrophenoxycarbonyloxy)-1,4,6,9-tetraoxacyclododecane (25l). The title compound was obtained from 8l as described for 25a in 67% yield after flash-chromatography (EtOAc): $^1$H NMR (CDCl$_3$) δ 8.27 (d, J=8.7 Hz, 2H), 7.38 (d, J=8.7 Hz, 2H), 5.01-4.95 (m, 1H), 4.70 (s, 2H), 3.91-3.76 (m, 12H).

Example 40

(1S,2R)-{1-Benzyl-2-hydroxy-3-[isobutyl(4-methoxybenzenesulfonyl)amino]propyl}carbamic acid (1S)-3,5-dioxacyclooctan-1-yl ester (3a). A solution of 27 (25 mg, 0.05 mmol) in a mixture of 30% trifluoroacetic acid in CH$_2$Cl$_2$ (5 mL) was stirred at 23° C. for 40 min and then the solvent was removed under reduced pressure. Compound 28 thus obtained was dissolved in CH$_2$Cl$_2$ (4 mL) and a solution of 25a (16 mg, 0.05 mmol) in THF (2 mL) were added followed by diisopropylethylamine. After 48 h the organic phase was washed with water, dried (Na$_2$SO$_4$) and evaporated. The residue was purified by flash-chromatography eluting with a 1:4 mixture of EtOAc and hexane to afford 3a in 63% yield after flash-chromatography (1:4 EtOAc/CHCl$_3$) as a foam: $[α]_D^{20}$=+8.6 (c 1.1, CHCl$_3$); $^1$H NMR (CDCl$_3$) δ 7.70 (d, J=9.0 Hz, 2H), 7.31-7.21 (m, 5H), 6.97 (d, J=9.0 Hz, 2H), 4.83-4.78 (m, 2H), 4.65-4.59 (m, 2H), 3.87 (s, 3H), 3.83-3.81 (m, 3H), 3.68 (dd, J=4.9, 12.1 Hz, 1H), 3.55-3.48 (m, 2H), 3.14-2.90 (m, 5H), 2.78 (dd, J=6.8, 12.6 Hz, 1H), 1.85-1.80 (m, 5H), 0.90 (d, J=6.3 Hz, 3H), 0.85 (d, J=6.3 Hz, 3H); $^{13}$C NMR (CDCl$_3$) δ 163.0, 153.4, 137.6, 129.8, 129.6, 129.5, 128.4, 126.5, 114.3, 95.7, 73.9, 72.6, 69.2, 68.6, 58.7, 55.6, 55.0, 53.7, 35.4, 29.2, 27.2, 26.1, 20.1, 29.8. HRMS-ESI (m/z): (M+Na)$^+$ calcd for C$_{28}$H$_{40}$N$_2$NaO$_8$S, 587.2403. found, 587.2380.

Example 41

(1S,2R)-{1-Benzyl-2-hydroxy-3-[isobutyl(4-methoxybenzenesulfonyl)amino]propyl}carbamic acid (1S)-3,5-Dioxacycloheptan-1-yl ester (3b). The title compound was obtained from 27 and 25b as described for 3a in 69% yield after flash-chromatography (1:4 EtOAc/CHCl$_3$) as an amorphous solid: $[α]_D^{20}$=+10.5 (c 1.2, CHCl$_3$); $^1$H NMR (CDCl$_3$) δ 7.70 (d, J=8.7 Hz, 2H), 7.31-7.19 (m, 5H), 6.97 (d, J=8.7 Hz, 2H), 4.93 (d, J=8.4 Hz, 1H), 4.77-4.71 (m, 3H), 3.87 (s, 3H), 3.81-3.69 (m, 6H), 3.09-2.90 (m, 5H), 2.77 (dd, J=6.9, 13.2 Hz, 1H), 1.98-1.95 (m, 1H), 1.85-1.76 (m, 2H), 0.90 (d, J=6.9 Hz, 3H), 0.85 (d, J=6.3 Hz, 3H); $^{13}$C NMR (CDCl$_3$) δ 162.9, 155.5, 137.5, 129.7, 129.5, 129.4, 128.4, 126.5, 114.3, 94.9, 72.5, 71.9, 68.8, 62.3, 58.9, 55.6, 55.2, 53.7, 35.3, 27.3, 20.2, 19.9. HRMS-ESI (m/z): (M+Na)$^+$ calcd for C$_{27}$H$_{38}$N$_2$NaO$_8$S, 573.2247. found, 573.2260.

Example 42

(1S,2R)-{1-Benzyl-2-hydroxy-3-[isobutyl(4-methoxybenzenesulfonyl)amino]propyl}carbamic acid (1R)-3,5-dioxacyclooctan-1-yl ester (3c). The title compound was obtained from 27 and 25c as described for 3a in 50% yield after flash-chromatography (1:4 EtOAc/CHCl$_3$) as an amorphous solid $[α]_D^{20}$=+9.8 (c 1.1, CHCl$_3$); $^1$H NMR (CDCl$_3$) δ 7.70 (d, J=8.7 Hz, 2H), 7.31-7.21 (m, 5H), 6.97 (d, J=8.7 Hz, 2H), 4.80-4.79 (m, 2H), 4.65-4.61 (m, 2H), 3.87 (s, 3H), 3.82-3.80 (m, 2H), 3.71-3.62 (m, 2H), 3.56-3.48 (m, 2H), 3.12-2.85 (m, 5H), 2.77 (dd, J=6.3, 13.2 Hz, 1H), 1.83-1.74 (m, 4H), 1.71-1.66 (m, 1H), 0.91 (d, J=6.6 Hz, 3H), 0.86 (d, J=6.6 Hz, 3H). HRMS-ESI (m/z): (M+Na)$^+$ calcd for C$_{28}$H$_{40}$N$_2$NaO$_8$S, 587.2403. found, 587.2405.

Example 43

(1S,2R)-{1-Benzyl-2-hydroxy-3-[isobutyl(4-methoxybenzenesulfonyl)amino]propyl}carbamic acid (1R)-3,5-dioxacycloheptan-1-yl ester (3d). The title compound was obtained from 27 and 25d as described for 3a in 59% yield after flash-chromatography (1:4 EtOAc/CHCl$_3$) as a foam: $[α]_D^{20}$=+15.9 (c 0.6, CHCl$_3$); $^1$H NMR (CDCl$_3$) δ 7.71 (d, J=9.0 Hz, 2H), 7.30-7.18 (m, 5H), 6.98 (d, J=9.0 Hz, 2H), 4.88 (d, J=8.7 Hz, 1H), 4.77-4.71 (m, 3H), 3.87 (s, 3H), 3.81-3.61 (m, 6H), 3.18-3.07 (m, 2H), 3.04-2.92 (m, 2H), 2.86-2.74 (m, 2H), 1.90-1.77 (m, 3H), 0.92 (d, J=6.3 Hz, 3H), 0.86 (d, J=6.3 Hz, 3H); $^{13}$C NMR (CDCl$_3$) δ 162.8, 155.5, 137.6, 129.7, 129.5, 129.4, 128.4, 126.4, 114.3, 94.8, 72.6, 71.9, 68.6, 62.3, 58.8, 55.6, 55.1, 53.8, 35.8, 35.2, 27.3, 20.2, 19.9. HRMS-ESI (m/z): (M+Na)$^+$ calcd for C$_{27}$H$_{38}$N$_2$NaO$_8$S, 573.2247. found, 573.2254.

Example 44

(1S,2R)-{1-Benzyl-2-hydroxy-3-[isobutyl(4-methoxybenzenesulfonyl)amino]propyl}carbamic acid (R)-oxepan-3-yl ester (3e). The title compound was obtained from 27 and 25e as described for 3a in 72% yield after flash-chromatography (1:2 EtOAc/Hex) as an amorphous solid: $^1$H NMR (CDCl$_3$) δ 7.70 (d, 8.8 Hz, 2H), 7.30-7.19 (m, 5H), 6.97 (d, J=8.8 Hz, 2H), 4.81 (d, J=8.2 Hz, 1H), 4.77-4.74 (m, 1H), 3.87 (s, 3H), 3.81 (m, 3H), 3.70-3.69 (m, 2H), 3.61-3.57 (m, 1H), 3.12 (dd, J=8.2, 14.7 Hz, 1H), 3.05-3.84 (m, 4H), 2.77 (dd, J=6.6, 13.2 Hz, 1H), 1.86-1.60 (m, 6H), 1.49-1.41 (m, 1H), 0.91 (d, J=6.7 Hz, 3H), 0.86 (d, J=6.7 Hz, 3H); $^{13}$C NMR (CDCl$_3$) δ 162.9, 155.8, 137.5, 129.6, 129.5, 129.4, 128.4, 126.4, 114.2, 74.5, 73.6, 72.5, 72.4, 58.7, 55.5, 54.8, 53.7, 35.6, 31.9, 30.9, 27.1, 21.0, 20.0, 19.8. HRMS-ESI (m/z): (M+Na)$^+$ calcd for C$_{28}$H$_{40}$N$_2$NaO$_7$S, 571.2454. found, 571.2458.

Example 45

(1S,2R)-{1-Benzyl-2-hydroxy-3-[isobutyl(4-methoxybenzenesulfonyl)amino]propyl}carbamic acid (S)-oxepan-4-yl ester (3f). The title compound was obtained from 27 and 25f as described for 3a in 68% yield after flash-chromatography (1:2 EtOAc/Hex) as an amorphous solid: $^1$H NMR (CDCl$_3$) δ 7.71 (d, J=8.8 Hz, 2H), 7.29-7.21 (m, 5H), 6.98 (d, J=8.8 Hz, 2H), 4.78-4.76 (m, 2H), 3.94-3.81 (m, 5H), 3.71-3.60 (m, 3H), 3.56-3.50 (m, 1H), 3.12 (dd, J=8.0, 15.2 Hz, 1H), 3.04-2.86 (m, 4H), 2.79 (dd, J=6.4, 13.1 Hz, 1H), 1.94-1.64 (m, 7H), 0.91 (d, J=6.5 Hz, 3H), 0.86 (d, J=6.5 Hz, 3H). HRMS-ESI (m/z): (M+Na)$^+$ calcd for C$_{28}$H$_{40}$N$_2$NaO$_7$S, 571.2454. found, 571.2452.

Example 46

(1S,2R)-{1-Benzyl-2-hydroxy-3-[isobutyl(4-methoxybenzenesulfonyl)amino]propyl}carbamic acid Cycloheptanyl ester (3g). The title compound was obtained from 27 and 25g as described for 3a in 84% yield after flash-chromatography (1:6 EtOAc/CHCl$_3$) as an amorphous solid: $[α]_D^{20}$=+16.0 (c 0.9, CHCl$_3$); $^1$H NMR (CDCl$_3$) δ 7.70 (d, J=8.7 Hz, 2H), 7.31-7.22 (m, 5H), 6.97 (d, J=8.7 Hz, 2H), 4.69-4.68 (m, 2H), 3.87 (s, 3H), 3.82-3.78 (m, 2H), 3.05-2.77 (m, 6H), 1.83-1.73 (m, 4H), 1.60-1.45 (m, 8H), 1.22-1.20 (m, 1H), 0.90 (d, J=6.3 Hz, 3H), 0.86 (d, J=6.3 Hz, 3H). HRMS-ESI (m/z): (M+Na)$^+$ calcd for C$_{29}$H$_{42}$N$_2$NaO$_6$S, 569.2661. found, 569.2663.

Example 47

(1S,2R)-{1-Benzyl-2-hydroxy-3-[isobutyl(4-methoxybenzenesulfonyl)amino]propyl}carbamic acid 1,3-dioxan-5-yl ester (3h). The title compound was obtained from 25h and 27 as described for 3a in 67% yield after flash-chromatography (1:6 EtOAc/CHCl$_3$): $[α]_D^{20}$=+7.9 (12.3 mg/mL CH$_2$Cl$_2$); $^1$H NMR (CDCl$_3$) δ 7.71 (d, J=9.3 Hz, 2H), 7.32-7.22 (m, 5H), 6.98 (d, J=9.3 Hz, 2H), 5.06 (d, J=8.4 Hz, 1H), 4.92 (d, J=6.2 Hz, 1H), 4.75 (d, J=6.2 Hz, 1H), 4.51-4.49 (m, 1H), 3.95-3.74 (m, 9H), 3.14 (dd, J=8.1, 15.0 Hz, 1H), 3.06-2.84 (m, 4H), 2.77 (dd, J=6.7, 13.3 Hz, 1H), 1.86-1.77 (m, 1H), 0.92 (d, J=6.6 Hz, 3H), 0.87 (d, J=6.6 Hz, 3H); $^{13}$C NMR (CDCl$_3$) δ 162.9, 155.4, 137.3, 129.7, 129.6, 129.5, 128.5, 126.5, 114.3, 93.6, 72.3, 68.7, 66.3, 58.8, 55.6, 55.2, 53.8, 35.7, 27.3, 20.2, 19.9. HRMS-ESI (m/z): (M+Na)$^+$ calcd for C$_{26}$H$_{36}$N$_2$NaO$_8$S, 559.2090. found, 559.2094.

Example 48

(1S,2R)-{1-Benzyl-2-hydroxy-3-[isobutyl(4-methoxybenzenesulfonyl)amino]propyl}carbamic acid 3,6,9-trioxacyclodecan-1-yl ester (3i). The title compound was obtained from 25i and 27 as described for 3a in 37% yield after flash-chromatography (1:1 EtOAc/CHCl$_3$) as a white solid: mp 60-62° C.; $[α]_D^{20}$=+6.2 (c 0.3, CHCl$_3$); $^1$H NMR (CDCl$_3$) δ 7.69 (d, J=8.7 Hz, 2H), 7.33-7.18 (m, 5H), 6.96 (d, J=8.7 Hz, 2H), 5.33 (d, J=8.1 Hz, 1H), 4.84-4.82 (m, 1H), 3.86 (s, 3H), 3.79-3.75 (m, 2H), 3.68-3.55 (m, 12H), 3.07-2.78 (m, 6H), 1.84-1.81 (m, 1H), 0.89 (d, J=7.2 Hz, 3H), 0.85 (d, J=7.2 Hz, 3H). HRMS-ESI (m/z): (M+Na)$^+$ calcd for C$_{29}$H$_{42}$N$_2$NaO$_9$S, 617.2509. found, 617.2501.

Example 49

(1S,2R)-{1-Benzyl-2-hydroxy-3-[isobutyl(4-methoxybenzenesulfonyl)amino]propyl}carbamic acid 3,6,9,12-tetraoxacyclotridecan-1-yl ester (3j). The title compound was obtained from 27 and 25j as described for 3a in 30% yield after flash-chromatography (EtOAc) as a foam: $[α]_D^{20}$=+17.0 (c 0.9, CHCl$_3$); $^1$H NMR (CDCl$_3$) δ 7.70 (d, J=9.0 Hz, 2H), 7.29-7.19 (m, 5H), 6.97 (d, J=9.0 Hz, 2H), 4.96 (d, J=8.0 Hz, 1H), 4.85-4.83 (m, 1H), 3.87 (s, 3H), 3.83-3.81 (m, 2H), 3.80-3.60 (m, 15H), 3.52 (dd, J=3.5, 9.5 Hz, 1H), 3.13 (dd, J=9.0, 15.5 Hz, 1H), 3.02-2.86 (m, 4H), 2.77 (dd, J=6.5, 13.5 Hz, 1H), 1.83-1.76 (m, 1H), 0.90 (d, J=6.5 Hz, 3H), 0.85 (d, J=6.5 Hz, 3H); $^{13}$C NMR (CDCl$_3$) (500 MHz) δ 163.0, 155.4, 137.6, 129.7, 129.6, 129.5, 128.5, 126.5, 114.4, 72.4, 71.7, 70.2, 70.1, 69.9, 67.8, 58.7, 55.6, 55.1, 53.7, 35.5, 27.3, 20.2, 19.9. HRMS-ESI (m/z): (M+Na)$^+$ calcd for C$_{31}$H$_{46}$N$_2$NaO$_{10}$S, 661.2771. found, 661.2788.

Example 50

(1S,2R)-{1-Benzyl-2-hydroxy-3-[isobutyl(4-methoxybenzenesulfonyl)amino]propyl}carbamic acid 3,6,8,11-tetraoxacyclododecan-1-yl ester (3k). The title compound was obtained from 27 and 25k as described for 3a in 47% yield after flash-chromatography (EtOAc) as a foam: $[α]_D^{20}$=+6.5 (c 0.5, CHCl$_3$); $^1$H NMR (CDCl$_3$) 7.70 (d, J=8.7 Hz, 2H), 7.30-7.18 (m, 5H), 6.97 (d, J=8.7 Hz, 2H), 4.92 (d, J=8.1 Hz, 1H), 4.81-4.76 (m, 1H), 4.66 (s, 2H), 3.87 (s, 3H), 3.78-344 (m, 14H), 3.13 (dd, J=8.4, 15.3 Hz, 1H), 3.06-2.82 (m, 4H), 2.75 (dd, J=6.9, 13.5 Hz, 1H), 1.83-1.74 (m, 1H), 0.90 (d, J=6.6 Hz, 3H), 0.85 (d, J=6.3 Hz, 3H); $^{13}$C NMR (CDCl$_3$) δ 163.0, 155.6, 137.5, 129.8, 129.6, 129.5, 128.5, 126.5, 114.4, 94.7, 72.4, 71.5, 69.7, 64.9, 64.5, 58.8, 55.7, 55.1, 53.8, 35.6, 27.3, 20.2, 19.9. HRMS-ESI (m/z): (M+Na)$^+$ calcd for C$_{30}$H$_{44}$N$_2$NaO$_{10}$S, 647.2615. found, 647.2590.

Example 51

(1S,2R)-{1-Benzyl-2-hydroxy-3-[isobutyl(4-methoxybenzenesulfonyl)amino]propyl}carbamic acid 3,9-dioxa-6-thiacyclodecan-1-yl 6,6-dioxide ester (3l). The title compound was obtained from 27 and 25l as described for 3a in 36% yield after flash-chromatography (1:1 EtOAc/CHCl$_3$) as an amorphous solid: $[α]_D^{20}$=+5.5 (c, 0.7, CHCl$_3$); $^1$H NMR (CDCl$_3$) δ 7.70 (d, J=9.0 Hz, 2H), 7.31-7.20 (m, 5H), 6.98 (d, J=9.0 Hz, 2H), 4.97 (d, J=8.4 Hz, 1H), 4.85 (t, J=4.5 Hz, 1H), 4.01-3.96 (m, 4H), 3.88 (s, 3H), 3.85-3.83 (m, 2H), 3.71-3.69 (m, 1H), 3.61 (dd, J=3.9, 9.3 Hz, 1H), 3.54-3.47 (m, 2H), 3.61-3.27 (m, 4H), 3.13 (dd, J=8.4, 15.0 Hz, 1H), 3.00-2.82 (m, 4H), 2.75 (dd, J=6.6, 13.5 Hz, 1H), 1.83-1.75 (m, 1H), 0.91 (d, J=6.6 Hz, 3H), 0.86 (d, J=6.3 Hz, 3H); $^{13}$C NMR (CDCl$_3$) δ 163.0, 155.1, 137.4, 131.1, 129.6, 129.4, 128.4, 126.5, 114.3, 72.4, 70.2, 66.0, 64.6, 58.8, 55.7, 55.1, 53.7, 52.2, 35.4, 27.3, 20.2, 19.9. HRMS-ESI (m/z): (M+Na)$^+$ calcd for C$_{29}$H$_{42}$N$_2$NaO$_{10}$S$_2$, 665.2179. found, 665.2191.

Example 52

N-(tert-Butoxycarbonyl)-9-(4-nitrophenoxycarbonyloxy)-1,7-dioxa-4-azocyclodecane (29). The title compound was obtained from 24 as described for 25a in 73% yield after flash-chromatography (1:4 EtOAc/CHCl$_3$): $^1$H MR (CDCl$_3$) δ 8.27 (d, J=9.0 Hz, 2H), 7.37 (d, J=9.0 Hz, 2H), 5.02-4.96 (m, 1H), 3.98-3.76 (m, 8H), 4.52-3.23 (m, 4H), 1.47 (s, 9H).

Example 53

(1S,2R)-{1-Benzyl-2-hydroxy-3-[isobutyl(4-methoxybenzenesulfonyl)amino]propyl}carbamic acid N-(tert-butoxycarbonyl)-1,7-dioxa-4-azocyclodecan-9-yl ester (30). The title compound was obtained from 27 and 29 as described for 3a in 74% yield after flash-chromatography (1:1 EtOAc/CHCl$_3$) as a white solid: mp 71-73° C.; $[α]_D^{20}$=+4.7 (c 1.7, CHCl$_3$); $^1$H NMR (CDCl$_3$) 7.70 (d, J=9.0 Hz, 2H), 7.30-7.20 (m, 5H), 7.0 (d, J=9.0 Hz, 2H), 4.92-4.90 (m, 1H), 4.81 (t, J=4.0 Hz, 1H), 3.86 (s, 3H), 3.79-3.66 (m, 6H), 3.62-3.57 (m, 2H), 3.49-3.42 (m, 2H), 3.40-3.28 (m, 4H), 3.12 (dd, J=7.8, 15.3 Hz, 1H), 3.01-2.82 (m, 4H), 2.75 (dd, J=6.3, 13.2 Hz, 1H), 1.83-1.74 (m, 1H), 1.44 (s, 9H), 0.90 (d, J=6.6 Hz, 3H), 0.85 (d, J=6.6 Hz, 3H); $^{13}$C NMR (CDCl$_3$) 163.0, 155.6, 155.4, 137.4, 129.7, 129.5, 129.4, 128.4, 126.5, 114.3, 79.9, 72.4, 71.9, 71.0, 68.6, 68.1, 58.7, 55.6, 55.0, 53.7, 50.3, 35.6, 28.5, 27.3, 20.2, 19.9.

Example 54

(1S,2R)-{1-Benzyl-2-hydroxy-3-[isobutyl(4-methoxybenzenesulfonyl)amino]propyl}carbamic acid 1,7-dioxa-4-azocyclodecan-9-yl ester (31). A solution of 30 (13 mg, 0.02 mmol) in a mixture of 30% trifluoracetic acid in CH$_2$Cl$_2$ (1 mL) was stirred at 23° C. for 30 min and then the solvent was removed under reduced pressure. The residue was dissolved in CH$_2$Cl$_2$ and the organic phase was washed with a saturated solution of NaHCO$_3$, dried (Na$_2$SO$_4$) and evaporated to afford 11 mg (100%) of 31 as a white solid: mp 65-66° C.; $[α]_D^{20}$=+13.8 (c 0.7, CHCl$_3$); $^1$H NMR (CDCl$_3$) δ 7.70 (d, J=8.7 Hz, 2H), 7.30-7.18 (m, 5H), 6.97 (d, J=8.7 Hz, 2H), 5.20 (d, J=8.4 Hz, 1H), 4.82-4.79 (m, 1H), 3.87 (s, 3H), 3.84-3.80 (m, 2H), 3.75-3.64 (m, 7H), 3.54 (dd, J=5.4, 10.2 Hz, 1H), 3.13 (dd, J=8.4, 15.3 Hz, 1H), 3.04-2.84 (m, 8H), 2.77 (dd, J=6.9, 13.5 Hz, 1H), 2.38 (bs, 1H), 1.85-1.76 (m, 1H), 0.90 (d, J=6.3 Hz, 3H), 0.85 (d, J=6.6 Hz, 3H); $^{13}$C NMR (CDCl$_3$) δ 162.9, 155.3, 137.5, 129.8, 129.5, 129.4, 128.4, 126.4, 114.3, 72.4, 71.8, 68.6, 58.7, 55.6, 55.1, 53.6, 53.4, 48.2, 35.6, 27.2, 20.2, 19.9.

Example 55

(1S,2R)-{1-Benzyl-2-hydroxy-3-[isobutyl(4-methoxybenzenesulfonyl)amino]propyl}carbamic acid N-methyl-1,7-dioxa-4-azocyclodecan-9-yl ester (3m). To a solution of 31 (9.0 mg, 0.015 mmol) in a mixture of 1% acetic acid in methanol (0.5 mL), formaldehyde (37% solution in H$_2$O, 12 µL, 0.15 mmol) and sodium cyanoborohydride (2.0 mg, 0.03 mmol) were added. After 18 h a saturated solution of NaHCO$_3$ was added, the solvent was removed and the aqueous phase was extracted with CH$_2$Cl$_2$. The organic extracts were dried (Na$_2$SO$_4$), evaporated and the residue was purified by flash-chromatography eluting with a 10:1 mixture of CHCl$_3$ and MeOH to afford 8.0 mg (87%) of 3m as an amorphous solid: $[α]_D^{20}$=+8.1 (c 0.6, CHCl$_3$); $^1$H NMR (CDCl$_3$) δ 7.70 (d, J=8.7 Hz, 2H), 7.3-7.18 (m, 5H), 6.98 (d, J=8.7 Hz, 2H), 4.99 (d, J=8.1 Hz, 1H), 4.80-4.77 (m, 1H), 3.87 (s, 3H), 3.83-3.74 (m, 4H), 3.70-3.56 (m, 6H) 3.14 (dd, J=8.1, 14.7 Hz, 1H), 3.02-2.69 (m, 9H), 2.40 (s, 3H), 1.83-1.74 (m, 1H), 0.90 (d, J=6.3 Hz, 3H), 0.85 (d, J=6.6 Hz, 3H); $^{13}$C NMR (CDCl$_3$) δ 162.9, 155.5, 137.4, 129.9, 129.4 (×2C), 128.4, 126.4, 114.3, 77.2, 72.3, 69.6, 67.6, 59.0, 55.6, 55.1, 53.6, 44.0, 35.6, 29.7, 27.2, 20.2, 19.9. HRMS-ESI (m/z): (M+Na)$^+$ calcd for C$_{30}$H$_{46}$N$_3$O$_8$S, 608.3006. found, 608.3009.

Example 56

Determination of X-ray structure of 3d-bound HIV protease. The HIV-1 protease construct with the substitutions Q7K, L33I, L63I, C67A and C95A to optimize protein stability was expressed and purified as described (Louis, J. M.; et al., Autoprocessing of HIV-1 protease is tightly coupled to protein folding. *Nat. Struct. Biol.* 1999, 6, 868-875; Mahalingam, B.; et al., Structural implications of drug resistant mutants of HIV-1 protease: High resolution crystal structures of the mutant protease/substrate analog complexes. *Proteins* 2001, 43, 455-464). Crystals were grown by the hanging drop vapor diffusion method using 1:15 molar ratio of protease at 2.0 mg/mL and inhibitor dissolved in dimethylsulfoxide. The reservoir contained 0.1 M sodium acetate buffer (pH=4.2) and 1.5 M NaCl. Crystals were transferred into a cryoprotectant solution containing the reservoir solution and 20-30% (v/v) glycerol, mounted on a nylon loop and flash-frozen in liquid nitrogen. X-ray diffraction data were collected on the SER-CAT beamline of the Advanced Photon Source, Argonne National Laboratory. Diffraction data were processed using HKL2000 (Otwinowski, Z.; Minor, W. Processing of X-ray diffraction data in oscillation mode. *Methods in Enzymology* 1997, 276, 307-326) resulting in an R$_{merge}$ value of 8.0% (41.1%) for 110,362 unique reflections between 50 and 1.00 Å resolution with a completeness of 88.4% (52.6%), where the values in parentheses are for the final highest resolution shell. Data were reduced in space group P2$_1$2$_1$2 with unit cell dimensions of a=57.96 Å, b=86.41 Å, c=46.03 Å with one dimer in the asymmetric unit. The structure was solved by molecular replacement using the CPP4i suite of programs, with the structure of the D30N mutant of HIV protease in complex with GRL-98065 (2QCI) as the starting model (Mahalingam, B.; et al., 2001; Collaborative Computational Project, Number 4 The CCP4 Suite: Programs for Protein Crystallography. *Acta Cryst.* 1994, D50, 760-763; Potterton, E.; et al., A graphical user interface to the CCP4 program suite. Acta. Cryst. 2003, D59, 1131-1137). The structure was refined using SHELX97 and refitted manually using the molecular graphics programs O and COOT (Sheldrick, G. M.; Schneider, T. R. SHELXL: High resolution refinement. *Methods in Enzymology* 1997, 277, 319-343; Jones, T. A.; et al., Improved methods for building protein models in electron density maps and the location of errors in these models. *Acta Cryst.* 1991, A47, 110-119; Emsley, P.; Cowtan, K. Coot: Model-Building Tools for Molecular Graphics. *Acta Cryst.* 2004, D60, 2126-2132). Alternate conformations were modeled for the protease residues when observed in the electron density maps. Anisotropic atomic displacement parameters (B-factors) were refined for all atoms including solvent molecules. Hydrogen atoms were added at the final stages of the refinement. The identity of ions and other solvent molecules from the crystallization conditions was deduced from the shape and peak height of the 2F$_o$-F$_c$ and F$_o$-F$_c$ electron density, the hydrogen bond interactions and interatomic distances. The solvent structure was refined with two sodium ions, three chloride ions, and 216 water molecules including partial occupancy sites. The final R$_{work}$ was 14.9% and R$_{free}$ was 17.5% for all data between 10 and 1.00 Å resolution. The rmsd values from ideal bonds and angle distances were 0.017 Å and 0.034 Å, respectively. The average B-factor was 11.4 and 16.5 Å$^2$ for protease main chain and side chain atoms, respectively, 12.9 Å² for inhibitor atoms and 22.6 Å² for solvent atoms. The X-ray crystal structure of the GRL-0255A complex with HIV protease will be deposited in the Protein Databank (PDB) with accession code 3DJK (Berman, H. M.; et al., The Protein Data Bank. *Nucleic Acids Res.* 2000, 28, 235-242).

Example 57

4-(tert-Butyldiphenylsilyloxy)-4H-cyclopentene (105). To a suspension of sodium hydride (60% in mineral oil, 0.92 g, 23 mmol) in THF (10 mL), cooled to 0° C., 1,6-heptadien-4-ol 104 (1 mL, 7.7 mmol) was added dropwise in 10 sec. The resulting suspension was stirred at 0° C. for 30 min and then tert-butyldiphenylchlorosilane (2 mL, 7.9 mmol) was added. The reaction mixture was stirred at 23° C. for 4 h and then quenched with a saturated solution of ammonium chloride. The solvent was removed in vacuo and the aqueous phase was extracted with $CH_2Cl_2$. The organic extracts were dried ($Na_2SO_4$), the solvent was removed and the residue was purified by flash-chromatography (1:10 EtOAc/Hex) to afford 30 4-(tert-butyldiphenylsilyloxy)hepta-1,6-diene (2.6 g, 96%) as a colorless oil: δH (300 MHz, $CDCl_3$) 7.70 (4H, dd, J1.6, 7.6 Hz, ArH), 7.47-7.38 (6H, m, ArH), 5.83-5.69 (2H, m, 2 CH=$CH_2$), 5.02-4.91 (4H, m, 2.CH=$CH_2$), 3.87-3.80 (1H, m, CHOSi), 2.31-2.12 (4H, m, 3-H2, 5-H2) and 1.08 [9H, s, 35 $C(CH_3)_3$]. To a solution of the above compound (2.0 g, 5.7 mmol) in dry $CH_2Cl_2$ (20 mL), second generation Grubbs catalyst (4.8 mg, 5.6 μmol) was added and the resulting mixture was heated under reflux for 2 h. Subsequently, the reaction mixture was cooled to 23° C., the solvent was 40 removed under reduced pressure and the residue was purified by flash-chromatography (1:10 EtOAc/Hex) to afford 105 (1.8 g, 98%) as a colorless oil: δH (300 MHz, $CDCl_3$) 7.67 (4H, dd, J1.8, 7.8, ArH), 7.45-7.34 (6H, m, ArH), 5.61 (2 H, s, 1-H, 2-H), 4.57-4.51 (1H, m, 4-H), 2.47-2.33 (4H, m, 3-$H_2$, 5-$H_2$) 45 and 1.05 [9H, s, $C(CH_3)_3$].

Example 58

(1α,2α,4β)-4-(tert-Butyldiphenylsilyloxy)-1,2-cyclopentanediol (106). A mixture of 105 (2.2 g, 6.7 mmol), osmium tetroxide (2.5 wt. % solution in tert-butanol, 2 mL), N-methylmorpholine-N50 oxide (1.1 g, 9.4 mmol), and pyridine (0.54 mL, 6.7 mmol) in a 3:2:1 mixture of tert-butanol, THF, and water (36 mL) was heated under reflux for 4 h. The reaction mixture was cooled to 23° C. and treated with a 20% aqueous solution of sodium bisulfite (10 mL). The organic solvents were removed under reduced pressure and the aqueous phase was extracted with EtOAc. The organic extracts were washed with 1 N hydrochloric acid, water, brine, and dried ($Na_2SO_4$). The solvent was removed in vacuo and the residue was purified by flash-chromatography (1:1 EtOAc/Hex) to yield diol 106 (2g, 81%) as a colorless oil: δH (300 MHz, $CDCl_3$) 7.62 (4H, dd, J1.8, 7.5, ArH), 7.45-7.33 (6H, m, ArH), 4.84-4.42 (1H, m, 4-H), 4.30-4.29 (2 H, m, 1-H, 2-H), 2.22 (2H, br. s, 2.OH), 1.99-1.80 (4H, m, 3-H2, 5-H2) and 1.04 [9H, s, $C(CH_3)_3$].

Example 59

(1β,2β,4α)-4-(tert-Butyldiphenylsilyloxy)-1,2-(methylenedioxy)cyclopentane (107) and (5aα,7β,8aα)-7-(tertbutyldiphenylsilyloxy) tetrahydrocyclopenta[f]-1,3,5-trioxepane (108). A mixture of paraformaldehyde (0.77 g, 25.7 mmol) and concentrated hydrochloric acid (2 mL) in $CHCl_3$ (2 mL) was stirred at 23° C. until a clear solution was formed (6 h) and then a solution of 106 (0.2 g, 0.54 mmol) in $CHCl_3$ (2 mL) was added. The resulting mixture was heated under reflux overnight and the aqueous phase was extracted with $CHCl_3$. The organic extracts were dried ($Na_2SO_4$) and evaporated under reduced pressure to yield 107 (0.18 g, 86%) after flash-chromatography (1:10 EtOAc/Hex 10): δH (300 MHz, $CDCl_3$) 7.64 (4H, d, J 6.3, ArH), 7.45-7.35 (6H, m, ArH), 4.78 (1H, s, OCHHO), 4.60 (1H, s, OCHHO), 4.51 (2H, d, J 5.4, 1-H, 2-H), 4.47-4.39 (1H, m, 4-H), 1.99 (2H, dd, J 6.0, 13.8, 3-H', 5-H'), 1.77-1.68 (2H, m, 3-H", 5-H") and 1.04 [9H, s, $C(CH_3)_3$]; δC (75 MHz, $CDCl_3$) 135.6, 134.0, 129.7, 127.6, 94.0, 78.8, 72.7, 41.0, 26.9 and 19.1. After further elution of the column 108 (0.5 g, 5%) was obtained: δH (300 MHz, $CDCl_3$) 7.66-7.62 (4H, m, ArH), 7.46-7.35 (6H, m, ArH), 5.17 (2H, d, J 7.8, 2-H', 4-H'), 4.70 (2H, d, J 7.8, 2-H", 4-H"), 4.52-4.43 (3H, m, 5a-H, 7H, 8a-H), 2.15-2.08 (2H, m, 6-H', 8-H'), 1.93-1.85 (2H, m, 6-H", 8-H") and 1.06 [9H, s, $C(CH_3)_3$]; δC (75 MHz, $CDCl_3$) 135.6, 133.8, 129.7, 127.7, 96.1, 82.5, 71.7, 41.1, 26.9 and 19.1.

Example 60

(4α,1β,2β)-4-Hydroxy-1,2-(methylenedioxy)cyclopentane (109). A mixture of 107 (0.47 g, 1.3 mmol) and n-$Bu_4N^+$ $F^-$ (1.0 M solution in THF, 1.4 mL, 1.4 mmol) in dry THF (10 mL) was stirred at 23° C. for 16 h. To the reaction mixture was added to a saturated solution of $NaHCO_3$, the solvent was removed in vacuo and the aqueous phase was extracted with $Et_2O$. The organic extracts were dried ($Na_2SO_4$) and evaporated and the residue was purified by flash-chromatography (1:1 EtOAc/Hex) to yield 109 (0.16 g, 96%) as a colorless oil: δH (300 MHz, $CDCl_3$) 4.89 (1H, s, OCHHO), 4.59 (1H, s, OCHHO), 4.50 (2H, d, J 6.0, 1-H, 2-H), 4.41-4.32 (1H, m, 4-H), 3.13 (1H, br. s, OH), 2.09 (2H, dd, J 5.6, 14.0, 3-H', 5-H') and 1.61-1.51 (2H, m, 3-H", 5-H"); δC (75 MHz, $CDCl_3$) δ4.1, 78.9, 70.8 and 40.6.

Example 61

(5aα,7β,8aα)-7-Hydroxytetrahydrocyclopenta[f]-1,3,5-trioxepane (110). The title compound was obtained as described for 109 in 83% yield. Flash-chromatography was performed using EtOAc: δH (300 MHz, $CDCl_3$) 5.15 (2H, d, J 7.2, 2-H', 4-H'), 4.67 (2H, d, J 7.2, 2-H", 4-H"), 4.47-4.40 (3H, m, 5a-H, 7-H, 8a-H), 2.07-2.02 (4H, m, 6-H2,8-H2) and 1.86 (1H, br. s, OH); δC (75 MHz, $CDCl_3$) δ6.1, 82.3, 70.0 and 40.8.

Example 62

(1β,2β,4β)-4-Hydroxy-1,2-(methylenedioxy)cyclopentane (111). To a mixture of 109 (100 mg, 0.77 mmol), p-nitrobenzoic acid (250 mg, 1.5 mmol), and triphenylphosphine (450 mg, 1.5 mmol), was added diisopropylazodicarboxylate (300 μL, 1.5 mmol) dropwise and the resulting mixture was stirred at 23° C. After 16 h, the solvent was removed under reduced pressure and the residue was purified by flashchromatography (1:2 EtOAc/Hex). The resulting ester was dissolved in a 3:2:1 mixture of THF, methanol, and water (10 mL) and LiOH.$H_2O$ (162 mg, 3.8 mmol) was added. The yellow mixture was stirred at 23° C. for 5 h and then the solvent was removed in vacuo. The residue was diluted with water and the aqueous phase was extracted with $Et_2O$. The organic extracts were dried ($Na_2SO_4$) and the solvent evaporated. Purification of the residue by flashchromatography (1:1 EtOAc/Hex) afforded 111 (57 mg, 57%) as a colorless oil: δH (300 MHz, $CDCl_3$) 5.17 (1H, s, OCHHO), 4.68 (1H, s, OCHHO), 4.61 (2H, d, J 4.8, 1-H, 2-H), 4.27 (1H, t, J 4.7, 4-H), 2.33 (1H, br. s, OH), 2.21 (2H, d, J 15.3, 3-H', 5-H') and 1.85-1.77 (2H, m, 3-H", 5-H"); $\delta$C (75 MHz, CDCl$_3$) $\delta$4.7, 81.5, 74.0 and 41.0.

Example 63

(5a$\alpha$,7$\alpha$,8a$\alpha$)-7-Hydroxytetrahydrocyclopenta[f]-1,3,5-trioxepane (112). The title compound 12 was obtained as described for 111 in 69% yield. Flash-chromatography was performed using EtOAc: $\delta$H (300 MHz, CDCl$_3$) 5.18 (2H, d, J 7.2, 2-H', 4-H'), 4.67 (2H, d, J 7.2, 2-H", 4-H"), 4.31-4.25 (2H, m, 5a-H, 8a-H), 4.18-4.13 (1 H, m, 7-H), 2.40 (1H, br. s, OH), 2.17-2.08 (2H, m, 6-H', 8-H') and 2.03-1.96 (2H, m, 6-H", 8-H"); $\delta$C (75 MHz, CDCl$_3$) $\delta$5.3, 82.8, 71.0 and 41.1.

Example 64

(±)-(1$\beta$,2$\beta$,4$\alpha$)-2-(2'-Hydroxyethoxy)-4-(tertbutyldiphenylsilyloxy)cyclopentane-1-ol (113). A mixture of 106 (100 mg, 0.29 mmol) and dibutyltin oxide (73 mg, 0.29 mmol) in dry toluene (10 mL) was heated under reflux with azeotropic removal of water. After 5 h, the reaction mixture was concentrated to half the initial volume and chloroethanol (195 μL, 2.9 mmol) and n-Bu$_4$N$_+$I$_-$ (109 mg, 0.29 mmol) were added. The resulting mixture was heated under reflux for 19 h, afterward the solvent was evaporated and the residue was purified by flash-chromatography (10:1 EtOAc/MeOH) to afford 113 (80 mg, 68%) as a colorless oil: $\delta$H (300 MHz, CDCl$_3$) 7.62 (4H, d, J 8.7, ArH), 7.44-7.33 (6H, m, ArH), 4.45-4.40 (1H, m, 4-H), 4.33-4.28 (1H, m, 2-H), 4.04-3.98 (1H, m, 1-H), 3.76-3.71 (2H, m, CH$_2$O), 3.66-3.55 (2H, m, CH$_2$O), 3.01 (2H, br. s, 2.OH), 1.97-1.80 (4H, m, 3-H2, 5-H2) and 1.04 (s, 9H]); $\delta$C (75 MHz, CDCl$_3$) 135.6, 134.1, 129.6, 127.6, 80.7, 71.1, 71.0, 70.8, 61.7, 42.3, 39.0, 26.9 and 14.2.

Example 65

(1$\beta$,2$\beta$,4$\alpha$)-4-(tert-butyldiphenylsilyloxy)-1,2-(ethylenedioxy)cyclopentane (114). A mixture of 113 (239 mg, 0.60 mmol), p-toluenesulfonyl chloride (250 mg, 1.3 mmol), pyridine (240 μL, 3.0 mmol) and a catalytic amount of N,N-dimethylaminopyridine in CH$_2$Cl$_2$ (8 mL) was stirred at 23° C. for 24 h. The reaction mixture was treated with 1N HCl and the aqueous phase was extracted with CH$_2$Cl$_2$. The organic extracts were dried (Na$_2$SO$_4$) and the solvent was removed. Purification of the residue by flash-chromatography (1:1 EtOAc/Hex) afforded the tosylated alcohol (182 mg, 55%) as a colorless oil: $\delta$H (300 MHz, CDCl$_3$) 7.76 (2H, d, J 8.4, ArH), 7.61 (4H, d, J 7.8, ArH), 7.42-7.26 (8H, m, ArH), 4.53-4.25 (1H, m, CHO), 4.15-4.09 (3H, m, CHO, CH$_2$O), 3.96-3.91 (1H, m, CHO), 3.68-3.62 (2H, m, CH$_2$O), 2.41 (3H, s, CH$_3$), 1.89-1.75 (4H, m, 3-H2, 5-H2) and 1.03 [9H, s, C(CH$_3$)$_3$]. To a solution of the above product (150 mg, 0.27 mmol) in dry THF (12 mL), NaH (60% in mineral oil, 22 mg, 0.54 mmol) was added and the resulting suspension was heated under reflux for 30 sec. After cooling to 23° C., the reaction mixture was quenched with a saturated solution of NH$_4$Cl, the solvent was removed and the aqueous phase was extracted with EtOAc. The organic extracts were dried (Na$_2$SO$_4$) and the solvent was removed in vacuo. The residue was purified by flash-chromatography (1:3 EtOAc/Hex) to afford 114 (82 mg, 80%) as a colorless oil: $\delta$H (300 MHz, CDCl$_3$) 7.65 (4H, d, J 7.8, ArH), 7.46-7.36 (6H, m, ArH), 4.55-4.48 (1H, m, 4-H), 4.18 (2H, t, J 5.1, 1-H, 2-H), 3.70-3.62 (2H, m, CH$_2$O), 3.53-3.46 (2H, m, CH$_2$O), 2.16-2.07 (2H, m, 3-H', 5-H'), 1.82-1.74 (2H, m, 3-H", 5-H") and 1.06 [9H, s, C(CH$_3$)$_3$]; $\delta$C (75 MHz, CDCl$_3$) 135.6, 134.1, 129.5, 127.6, 75.2, 71.1, 62.2, 37.5, 27.0 and 19.1.

Example 66

(1$\beta$,2$\beta$,4$\alpha$)-4-Hydroxy-1,2-(ethylendioxy)cyclopentane (115). The above compound was deprotected as described for 109 to afford 15 in 90% yield as a colorless oil: $\delta$H (300 MHz, CDCl$_3$) 4.58-4.51 (1H, m, 4-H), 4.17 (2H, t, J 4.8, 1-H, 2-H), 3.78-3.71 (2H, m, CH$_2$O), 3.58-3.51 (2H, m, CH$_2$O), 2.34-2.25 (2H, m, 3-H', 5-H') and 1.72-1.66 (3H, m, 3-H", 5-H", OH); $\delta$C (75 MHz, CDCl$_3$) 75.1, 69.6, 62.3 and 37.2.

Example 67

(1$\beta$,2$\beta$,4$\beta$)-4-Hydroxy-1,2-(ethylendioxy)cyclopentane (116). Starting from 15 the title compound 116 was obtained as described for 111 in 83% yield as a colorless oil. Flash-chromatography was performed using EtOAc: $\delta$H (300 MHz, CDCl$_3$) 4.22-4.16 (1H, m, 4-H), 4.01 (2H, t, J 4.2, 1-H, 2-H), 3.88-3.80 (2H, m, CH$_2$O), 3.63-3.55 (2H, m, CH$_2$O), 2.57 (1H, br. s, OH) and 2.10-1.93 (4H, m, 3-H2, 5-H2); $\delta$C (75 MHz, CDCl$_3$) 76.0, 71.4, 62.3 and 37.5.

Example 68

(1$\beta$,2$\beta$,4$\beta$)-1,2-(Methylenedioxy)cyclopent-4-yl succinimidylcarbonate (117). To a solution of 109 (67 mg, 0.52 mmol) in dry acetonitrile (2 mL), N,N'-disuccimidyl carbonate (198 mg, 0.77 mmol) and triethylamine (145 μL, 1.0 mmol) were added and the resulting mixture was stirred at 23° C. After 8 h the solvent was removed, the residue was taken-up in a saturated solution of NaHCO$_3$ and the aqueous phase was extracted with EtOAc. The organic extracts were dried (Na$_2$SO$_4$) and the solvent was removed in vacuo. Purification of the residue by flashchromatography (10:1 CHCl$_3$/MeOH) yielded 117 (58 mg, 55%): $\delta$H (300 MHz, CDCl$_3$) 5.27 (1H, t, J 7.2, 4-H), 4.97 (1H, s, OCHHO), 4.69 (1H, s, OCHHO), 4.61-4.59 (2H, m, 1-H, 2-H), 2.82 (4 H, s, CH$_2$CH$_2$), 2.38 (2H, dd, J 6.2, 14.2, 3-H', 5-H') and 1.99-1.89 (2H, m, 3-H", 5-H").

Example 69

(5a$\alpha$,7$\beta$,8a$\alpha$)-7-(4-nitrophenoxycarbonyloxy)tetrahydrocyclopenta[f]-1,3,5-trioxepane (118). To a solution of 110 (15 mg, 0.094 mmol) and N-methylmorpholine (31 μL, 0.28 mmol) in dry THF (3 mL), nitrophenylchloroformate (57 mg, 0.28 mmol) was added and the resulting mixture was stirred at 23° C. After 1 h, water was added, the solvent was removed under reduced pressure and the aqueous phase was extracted with CHCl$_3$. The organic extracts were dried (Na$_2$SO$_4$) and the solvent was evaporated. The residue was purified by flash-chromatography (1:4 EtOAc/CHCl$_3$) to afford 118 (31 mg, 95%) as a pale yellow viscous oil: $\delta$H (300 MHz, CDCl$_3$) 8.27 (2H, d, J 8.7, ArH), 7.38 (2H, d, J 8.7, ArH), 5.34-5.31 (1H, m, 7-H), 5.19 (2H, d, J 6.9, 2-H', 4-H'), 4.77 (2H, d, J 6.9, 2-H", 4-H"), 4.51-4.47 (2H, m, 5a-H, 8a-H) and 2.38-2.26 (4 H, m, 6-H2,8-H2); $\delta$C (75 MHz, CDCl$_3$) 155.3, 126.2, 125.3, 121.7, 115.6, 95.5, 81.2, 78.5 and 37.6.

Example 70

(1$\beta$,2$\beta$,4$\beta$)-4-(4-Nitrophenoxycarbonyloxy)-1,2-(methylenedioxy)cyclopentane (119). The title compound 119 was obtained from 111 as described for 118 in 81% yield. Flash-chromatography was performed using 1:1 EtOAc/Hex: $\delta$H (300 MHz, CDCl$_3$) 8.27 (2H, d, J 5.1, ArH), 7.38 (2H, d, J 5.1, ArH), 5.20-5.16 (2H, m, OCH$_2$O), 4.83-4.81 (1H, m, 4-H), 4.68 (2H, d, J 5.7, 1-H, 2-H), 2.38 (2H, d, J 14.7, 3-H', 5-H') and 2.11-2.02 (2H, m, 3-H", 5-H").

Example 71

(5aα,7a,8aα)-7-(4-Nitrophenoxycarbonyloxy)tetrahydrocyclopenta[f]-1,3,5-trioxepane (120). The title compound was obtained from 112 as described for 118 in 94% yield. Flash-chromatography was performed using 1:6 EtOAc/CHCl$_3$: δH (300 MHz, CDCl$_3$) 8.25 (2H, d, J 8.0, ArH), 7.39 (2H, d, J 8.0, ArH), 5.20 (2H, d, J 7.5, 2-H', 4-H'), 5.10-5.02 (1H, m, 7-H), 4.75 (2H, d, J 7.5, 2-H", 4-H"), 4.29-4.24 (2H, m, 5a-H, 8a-H), 2.51-2.41 (2H, m, 6-H', 8-H') and 2.25-2.17 (2H, m, 6-H", 8-H"); δC (75 MHz, CDCl$_3$) 155.2, 126.2, 125.2, 121.7, 115.6, 94.6, 80.8, 76.6 and 36.9.

Example 72

(1β,2β,4α)-4-(4-Nitrophenoxycarbonyloxy)-1,2-(ethylenedioxy)cyclopentane (121). The title compound was obtained from 115 as described for 118 in 81% yield. Flash-chromatography was performed using 1:4 EtOAc/CHCl$_3$. 6H (300 MHz, CDCl$_3$) 8.29 (2H, d, J 7.3, ArH), 7.36 (2H, d, J 7.3, ArH), 5.22-5.18 (1H, m, 4-H), 3.86-384 (2H, m, 1-H, 2-H), 3.78-3.63 (4H, m, 2×CH$_2$O), 2.38-2.24 (4H, m, 3-H$_2$, 5-H$_2$).

Example 73

(1β,2β,4β)-4-(4-Nitrophenoxycarbonyloxy)-1,2-(ethylenedioxy)cyclopentane (122). The title compound was obtained from 116 as described for 118 in 95% yield. Flash-chromatography was performed using 1:4 EtOAc/CHCl$_3$: 6H (400 MHz, CDCl$_3$) 8.27 (2H, d, J 7.0, ArH), 7.38 (2H, d, J 7.0, ArH), 5.14-5.10 (1H, m, 4-H), 3.99 (2H, t, J 4.6, 1-H, 2-H), 3.91-3.86 (2H, m, CH$_2$O), 3.64-3.59 (2H, m, CH$_2$O) and 2.31-2.18 (4H, m, 3-H$_2$, 5-H$_2$).

Example 74

(1'S,2'R)-{1'-Benzyl-2'-hydroxy-3'-[isobutyl(4-methoxybenzenesulfonyl)amino]propyl} carbamic acid (1β,2β,4β)-1,2-(methylenedioxy)cyclopent-4-yl ester (102). A solution of 124 (25 mg, 0.05 mmol) in 30% trifluoracetic acid in CH$_2$Cl$_2$ (4 mL) was stirred at 23° C. for 40 min and then the solvent was removed under reduced pressure. The residue was dissolved in THF (3 mL) and a solution of 119 (18 mg, 0.059 mmol) in THF (1 mL) was added. After 24 h the organic phase was diluted with CHCl$_3$, washed with water, dried (Na$_2$SO$_4$), and evaporated. The residue was purified by flash-chromatography eluting with a 1:1 mixture of EtOAc and hexanes to afford 2 (20 mg, 74%) as a white solid (found: M++H, 563.2406. C$_{28}$H$_{39}$N$_2$O$_8$S requires M, 563.2427): [α]D 20=+4.5 (c 1.2 in CH$_2$Cl$_2$) mp 68° C. (from EtOAc/Hex); δH (300 MHz, CDCl$_3$) 7.71 (2H, d, J 8.8, ArH), 7.32-7.19 (5H, m, ArH), 6.98 (2H, d, J 8.8, ArH), 5.01 (1H, s, OCHHO), 4.92 (1H, br. s, NH), 4.80 (2 H, m, 4-H, OCHHO), 4.57 (2H, d, J 5.4, 1-H, 2-H), 3.87 (3H, s, OCH3), 3.79 (2H, m, CHN, CHOH), 3.10-2.76 (6H, m, 2 CH$_2$N, CH$_2$Ph), 2.11-1.80 [5 H, m, 3-H2, 5-H2, CH(CH$_3$)$_2$], 0.90 (3H, d, J 6.6, CHCH$_3$) and 0.86 (3H, d, J 6.6, CHCH$_3$); δC (75 MHz, CDCl$_3$) 162.9, 155.3, 137.5, 129.9, 129.6, 129.3, 128.5, 126.4, 114.3, 94.7, 80.5, 74.2, 72.3, 58.8, 55.6, 54.9, 53.8, 38.5, 35.4, 27.3, 20.2 and 19.9; m/z (ES) 563 (M+1, 100)

Example 75

(1'S,2'R)-{1'-Benzyl-2'-hydroxy-3'-[isobutyl(4-methoxybenzenesulfonyl)amino]propyl} carbamic acid (1β,2β,4α)-1,2-(methylenedioxy)cyclopent-4-yl ester (126). A solution of 124 (40 mg, 0.079 mmol) in 30% trifluoracetic acid in CH$_2$Cl$_2$ (6 mL) was stirred at 23° C. for 40 min and then the solvent was removed under reduced pressure. The residue was dissolved in CH$_2$Cl$_2$ (4 mL) and a solution of 117 (23 mg, 0.1 mmol) in CH$_2$Cl$_2$ (2 mL) was added. After 2 h the organic phase was washed with water, dried (Na$_2$SO$_4$) and evaporated. The residue was purified by flashchromatography (1:1 EtOAc/Hex) to afford 126 (34 mg, 76%) as a white foam (found: M++Na, 585.2228. C$_{28}$H$_{38}$N$_2$NaO$_8$S requires M, 585.2247): [α]D 20=+3.6 (c 1.3 in CH$_2$Cl$_2$); δH (300 MHz, CDCl$_3$) 7.70 (2H, d, J 8.7, ArH), 7.32-7.21 (5H, m, ArH), 7.00 (2H, d, J 8.7, ArH), 5.06 (1H, t, J 7.0, 4-H), 4.93 (1H, s, OCHHO), 4.76 (1 H, d, J 8.4, NH), 4.71 (1H, s, OCHHO), 4.52 (2H, m, 1-H, 2-H), 3.87 (3H, s, OCH$_3$), 3.84 (2H, m, CHN, CHOH), 3.11 (1H, dd, J 8.0, 14.8, CHHN), 3.04-2.91 (4H, m, CHHN, CH$_2$N, CHHPh), 2.78 (1H, dd, J 6.7, 13.1, CHHPh), 2.17-2.10 (2H, m, 3-H', 5-H'), 1.86-1.58 [3 H, m, 3-H", 5-H", CH(CH$_3$)$_3$], 0.91 (3H, d, J 6.6, CHCH$_3$) and 0.87 (3 H, d, J 6.9, CHCH$_3$); δC (75 MHz, CDCl$_3$) 162.9, 155.8, 137.6, 129.9, 129.7, 129.4, 128.4, 126.5, 114.3, 94.3, 78.5, 74.5, 72.6, 58.8, 55.6, 54.9, 53.7, 37.8, 35.3, 27.3, 20.2 and 19.9; m/z (ES) 585 (M+Na, 100).

Example 76

(1S,2R)-{1'-Benzyl-2'-hydroxy-3'-[isobutyl(4-methoxybenzenesulfonyl)amino]propyl} carbamic acid (5aα,7β,8aα)-tetrahydrocyclopenta[f]-1,3,5-trioxaepan-7-yl ester (127). The title compound was obtained from 124 and 118 as described for 102 in 43% yield. Flash-chromatography was performed with 1:4 EtOAc/CHCl$_3$ (found: M++Na, 615.2361. C$_{29}$H$_{40}$N$_2$NaO$_9$S requires M, 615.2353): [α]$^D_{20}$=+5.2 (c 1.7 in CH$_2$Cl$_2$); δH (300 MHz, CDCl$_3$) 7.70 (2H, d, J 9.0, ArH), 7.32-7.21 (5H, m, ArH), 6.98 (2H, d, J 9.0, ArH), 5.15 (2H, d, J 7.2, 2-H', 4-H'), 5.05 (1H, br. s, NH), 4.76 (1H, d, J 8.4, 7-H), 4.68 (2H, d, J 7.2, 2-H", 4-H"), 4.32-4.23 (2H, m, 5a-H, 8a-H), 3.87 (3H, s, OCH$_3$), 3.83-3.80 (2H, m, CHN, CHOH), 3.10 (1H, dd, J 8.4, 15.3, CHHN Hz), 3.04-2.88 (4H, m, CHHN, CH$_2$N, CHHPh), 2.78 (1H, dd, J 6.9, 13.5, CHHPh), 2.09-1.94 (4H, m, 6-H$_2$, 8-H$_2$), 1.86-1.77 [1H, m, CH(CH$_3$)$_3$], 0.91 (3H, d, J 6.9, CHCH$_3$) and 0.87 (3H, d, J 6.3, CHCH$_3$); δC (75 MHz, CDCl$_3$) 163.0, 155.7, 137.6, 129.8, 129.7, 129.4, 128.4, 126.5, 114.3, 95.4, 81.5, 73.6, 72.7, 58.8, 55.7, 54.9, 53.7, 37.8, 35.4, 27.3, 20.2 and 19.9; m/z (ES) 615 (M+Na, 100).

Example 77

(1'S,2'R)-{1'-Benzyl-2'-hydroxy-3'-[isobutyl(4-methoxybenzenesulfonyl)amino]propyl} carbamic acid (5aα,7a, 8aα)-tetrahydrocyclopenta[f]-1,3,5-trioxaepan-7-yl ester (128). The title compound was obtained from 124 and 120 as described for 102 in 42% yield. Flash-chromatography was performed with 1:1 EtOAc/Hex (found: M++Na, 615.2349. C$_{29}$H$_{40}$N$_2$NaO9S requires M, 615.2353): [α]$^D_{20}$=+7.3 (c 1.7 in CH$_2$Cl$_2$); δH (300 MHz, CDCl$_3$) 7.70 (2H, d, J 8.7, ArH), 7.31-7.21 (5H, m, ArH), 6.97 (2H, d, J 8.7, ArH), 5.14 (2H, d, J 6.9, 2-H', 4-H'), 4.91 (1H, d, J 7.8, NH), 4.83-4.78 (1H, m, 7-H), 4.68 (2H, d, J 6.9, 2-H", 4-H"), 4.15-4.10 (2H, m, 5a-H, 8a-H), 3.87 (3H, s, OCH$_3$), 3.81-3.83 (2H, m, CHN, CHOH), 3.12-2.85 (5H, m, 2.CH$_2$N, CHHPh), 2.77 (1H, dd, J 6.9, 13.5, CHHPh), 2.34-2.21 (2H, m, 6-H', 8-H'), 1.94-1.76 [3 H, m, 6-H", 8-H", CH(CH$_3$)$_3$], 0.90 (3H, d, J 6.6, CHCH$_3$) and 0.86 (3 H, d, J 6.6, CHCH$_3$); m/z (ES) 615 (M+Na, 100).

Example 78

(1'S,2'R)-{1'-Benzyl-2'-hydroxy-3'-[isobutyl(4-methoxybenzenesulfonyl)amino]propyl} carbamic acid (1β,2β,4β)-1, 2-(ethylenedioxy)cyclopent-4-yl ester (103). The title compound was obtained from 124 and 122 as described for 102 in 40% yield. Flash-chromatography was performed with 1:1 EtOAc/Hex (found: M++Na, 599.2394. $C_{29}H_{40}N_2NaO_8S$ requires M, 599.2403): $[\alpha]^D{}_{20}$=+6.9 (c 0.7 in $CH_2Cl_2$); δH (500 MHz, $CDCl_3$) 7.70 (2H, d, J 9.0, ArH), 7.31-7.22 (5H, m, ArH), 6.97 (2H, d, J 9.0, ArH), 4.90-4.86 (2H, m, NH, 4-H), 3.87 (3H, s, $OCH_3$), 3.85-3.79 (7H, m, 2.$CH_2O$, 1-H, 2-H, OH), 3.57-3.54 (2H, m, CHN, CHOH), 3.11 (1H, dd, J 8.2, 14.7, CHHN), 3.03-2.88 (4H, m, CHHN, $CH_2N$, CHHPh), 2.78 (1H, dd, J 6.7, 13.2, CHHPh), 2.17-2.08 (2H, m, 3-H', 5-H'), 1.98-1.95 (2H, m, 3-H", 5-H"), 1.90 [1 H, dt, J 5.2, 15.0, $CH(CH_3)_3$], 0.91 (3H, d, J 6.5, $CHCH_3$) and 0.86 (3H, d, J 6.5, $CHCH_3$); δC (75 MHz, $CDCl_3$) 163.0, 156.2, 137.6, 129.8, 129.6, 129.5, 128.5, 126.5, 114.3, 74.5, 73.2, 72.5, 71.8, 62.5, 62.3, 58.8, 55.6, 55.0, 53.8, 35.5, 33.8, 33.5, 27.3, 20.2 and 19.9; m/z (ES) 599 (M+Na, 100).

Example 79

(1'S,2'R)-{1'-Benzyl-2'-hydroxy-3'-[isobutyl(4-methoxybenzenesulfonyl)amino]propyl} carbamic acid (1β,2β,4α)-1,2-(ethylenedioxy)cyclopent-4-yl ester (129). The title compound was obtained from 124 and 121 as described for 102 in 40% yield. Flash-chromatography was performed with 1:1 EtOAc/Hex (found: M++Na, 599.2421. $C_{29}H_{40}N_2NaO_8S$ requires M, 599.2403): $[\alpha]_{D20}$=+8.2 (c 1.0 in $CH_2Cl_2$); δH (500 MHz, $CDCl_3$) 7.70 (2H, d, J 8.7, ArH), 7.31-7.28 (2H, m, ArH), 7.24-7.22 (3H, m, ArH), 6.98 (2H, d, J 8.7, ArH), 5.09 (1H, br. s, NH), 4.74 (1H, d, J 8.0, 4-H), 4.06-4.01 (2H, m, 1-H, 2-H), 3.87 (3H, s, $OCH_3$), 3.82-3.81 (2H, m, $CH_2O$), 3.75-3.71 (2H, m, $CH_2O$), 3.55-3.51 (2H, m, CHN, CHOH), 3.10 (1H, dd, J 15.0, 8.5, CHHN), 3.03-2.86 88 (4H, m, CHHN, $CH_2N$, CHHPh), 2.78 (1H, dd, J 13.5, 6.5, CHHPh), 2.32-2.23 (2H, m, 3-H', 5-H'), 1.81 (1H, q, J=6.5, 3-H"), 1.79-1.68 (1H, m, 5-H"), 1.62-1.53 [1H, m, $CH(CH_3)_3$], 0.91 (3H, d, J 6.6, $CHCH_3$) and 0.86 (3H, d, J 6.6, $CHCH_3$); δC (75 MHz, $CDCl_3$) 163.1, 156.1, 137.6, 129.8, 129.6, 129.5, 128.5, 126.6, 114.4, 74.6, 73.2, 72.7, 62.2, 58.8, 55.7, 54.9, 53.8, 35.4, 34.3, 34.2, 27.3, 20.2 and 19.9; m/z (ES) 599 (M+Na, 100).

Example 80

(1'S,2'R)-{1'-Benzyl-2'-hydroxy-3'-[isobutyl(4-(hydroxymethyl)benzenesulfonyl)amino]propyl} carbamic acid (1β,2β,4β)-1,2-(methylenedioxy)cyclopent-4-yl ester (130). To a solution of 125 (ref. 8; Ghosh, et al., 2006) (40 mg, 0.1 mmol) and diisopropylethylamine (150 μL, 0.9 mmol) in THF (3 mL), a solution of 117 (30 mg, 0.11 mmol) was added and the resulting mixture was stirred at 23° C. After 48 h, the organic phase was diluted with $CHCl_3$, washed with water, dried ($Na_2SO_4$), and evaporated. The residue was purified by flash chromatography (2:1 EtOAc/Hex) to afford 130 (35 mg, 63%) as an amorphous solid (found: M++Na, 585.2246. $C_{28}H_{38}N_2NaO_8S$ requires M, 585.2247): $[\alpha]^D{}_{20}$=+7.8 (c 1.3 in $CHCl_3$); δH (400 MHz, $CDCl_3$) 7.77 (2H, d, J 8.1, ArH), 7.52 (2H, d, J 8.1, ArH), 7.32-7.21 (5H, m, ArH), 5.00 (1H, s, NH), 4.92 (1H, m, 4-H), 4.82-4.80 (4H, m, $OCH_2O$, $CH_2OH$), 4.58-4.57 (2H, m, 1-H, 2-H), 3.81-3.79 (2H, m, CHN, CHOH), 3.11-2.83 (6H, m, 2.$CH_2N$, CH2Ph), 6H), 2.10-1.82 [5 H, m, 3-H2, 5-H2, $CH(CH_3)_3$], 0.91 (3H, d, J 6.6, $CHCH_3$) and 0.83 (3H, d, J 6.6, $CHCH_3$). m/z (ES) 585 (M+Na, 100).

Example 81

X-Ray Crystallography. The HIV-1 protease construct with the substitutions Q7K, L33I, L63I, C67A, and C95A to optimize protein stability was expressed and purified according to published procedures (see, for example, Mahalingam, B.; 2001). Crystals were grown by the hanging drop vapor diffusion method using 1:15 molar ratio of protease at 2.0 mg/mL and inhibitor dissolved in dimethylsulfoxide. The reservoir contained 0.1 M sodium acetate buffer (pH=4.2) and 1.5 M NaCl. Crystals were transferred into a cryoprotectant solution containing the reservoir solution and 20-30% (v/v) glycerol, mounted on a nylon loop and flash35 frozen in liquid nitrogen. X-ray diffraction data were collected on the SER-CAT beamline of the Advanced Photon Source, Argonne National Laboratory. Diffraction data were processed using HKL2000 resulting in a Rmerge value of 7.0% (41.8%) for 90,315 unique reflections between 50 and 1.07 Å resolution with a completeness of 88.1% (51.3%), where the values in parentheses are for the final highest resolution shell. Data were reduced in space group P21212 with unit cell dimensions of a=58.00 Å, b=86.34 Å, c=45.83 Å with one dimer in the asymmetric unit. The structure was solved by molecular replacement using the CPP4i suite of programs, with the structure of the D30N mutant of HIV protease in complex with GRL-98065 (2QCI) as the starting model. The structure was refined using SHELX97 and refitted manually using the molecular graphics programs O and COOT. Alternate conformations were modeled for the protease residues when observed in the electron density maps. Anisotropic atomic displacement parameters (B-factors) were refined for all atoms including solvent molecules. Hydrogen atoms were added at the final stages of the refinement. The identity of ions and other solvent molecules from the crystallization conditions was deduced from the shape and peak height of the 2Fo-Fc and Fo-Fc electron density, the hydrogen bond interactions and interatomic distances. The solvent structure was refined with one sodium ion, three chloride ions, and 203 water molecules including partial occupancy sites. The final Rwork was 15.2% and Rfree 17.7% for all data between 10 and 1.07 Å resolution. rmsd values from ideal bonds and angle distances were 0.015 Å and 0.034 Å, respectively. The average B-factor was 13.1 and 18.2 Å² for protease main chain and side chain atoms, respectively, 12.5 Å² for inhibitor atoms and 24.0 Å² solvent atoms. The X-ray crystal structure of the inhibitor complex with HIV protease has been deposited in the Protein Databank (PDB) (see, for example, Berman, H. M.; 2000).

What is claimed is:

1. A compound of the formula

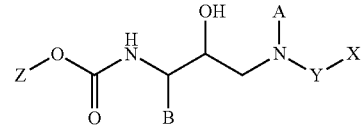

or a pharmaceutically acceptable salt thereof;
wherein
A is alkyl which is optionally substituted;
B is arylalkyl, which is optionally substituted;
X is optionally substituted aryl;
Y is $SO_2$;
Z is a radical of the formula

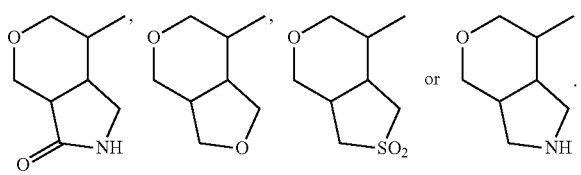 or

2. The compound of claim 1 wherein Z is a radical of the formula

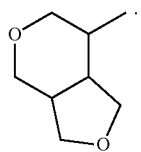

3. The compound of claim 1 wherein A is haloalkyl.
4. The compound of claim 1 wherein A is branched alkyl.
5. The compound of claim 1 wherein B is arylalkyl.
6. A pharmaceutical composition comprising one or more compounds of claim 1, and one or more carriers, diluents, or excipients, or a combination thereof.
7. A method of treating a patient in need of relief from an HIV infection; the method comprising the step of administering to the patient a therapeutically effective amount of a composition comprising one or more compounds of claim 1.
8. The method of claim 7 wherein the composition further comprises one or more carriers, diluents, or excipients, or a combination thereof.
9. The compound of claim 1 of the formula

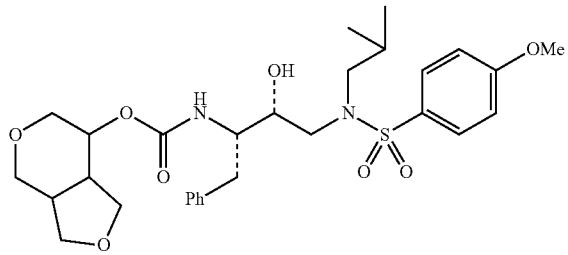 [SMILES: COc1ccc(S(=O)(=O)N(CC(C)C)C[C@@H](O)[C@H](Cc2ccccc2)NC(=O)OC2COCC3COCC32)cc1]

or a pharmaceutically acceptable salt thereof.
10. A pharmaceutical composition comprising the compound of claim 9, and one or more carriers, diluents, or excipients, or a combination thereof.
11. A method of treating a patient in need of relief from an HIV infection; the method comprising the step of administering to the patient a therapeutically effective amount of a composition comprising a compound of claim 9.
12. The method of claim 11 wherein the composition further comprises one or more carriers, diluents, or excipients, or a combination thereof.

* * * * *